US012788811B2

(12) United States Patent
Geiger et al.

(10) Patent No.: US 12,788,811 B2
(45) Date of Patent: Nov. 10, 2026

(54) METHOD OF TREATING AGE-RELATED DEPRESSION AND SARCOPENIA

(71) Applicants: Children's Hospital Medical Center, Cincinnati, OH (US); UNIVERSITAET ULM, Ulm (DE)

(72) Inventors: Hartmut Geiger, Cincinnati, OH (US); Yi Zheng, Cincinnati, OH (US); Maria Carolina Florian, Lonsee (DE)

(73) Assignees: CHILDREN'S HOSPITAL MEDICAL CENTER, Cincinnati, OH (US); UNIVERSITAET ULM, Ulm (DE)

( * ) Notice: Subject to any disclaimer, the term of this patent is extended or adjusted under 35 U.S.C. 154(b) by 953 days.

(21) Appl. No.: 17/635,655

(22) PCT Filed: Aug. 13, 2020

(86) PCT No.: PCT/US2020/046209

§ 371 (c)(1),
(2) Date: Feb. 15, 2022

(87) PCT Pub. No.: WO2021/034616

PCT Pub. Date: Feb. 25, 2021

(65) Prior Publication Data

US 2022/0288197 A1 Sep. 15, 2022

Related U.S. Application Data

(60) Provisional application No. 62/888,027, filed on Aug. 16, 2019.

(51) Int. Cl.

| | |
|---|---|
| ***A61K 39/39*** | (2006.01) |
| ***A61K 31/403*** | (2006.01) |
| ***A61K 31/404*** | (2006.01) |
| ***A61K 31/4985*** | (2006.01) |
| ***A61K 39/00*** | (2006.01) |
| ***A61P 21/00*** | (2006.01) |
| ***A61P 25/24*** | (2006.01) |
| ***A61P 37/04*** | (2006.01) |

(52) U.S. Cl.

CPC ............ *A61K 39/39* (2013.01); *A61K 31/403* (2013.01); *A61K 31/4985* (2013.01); *A61P 37/04* (2018.01); *A61K 2039/55511* (2013.01)

(58) Field of Classification Search

None

See application file for complete search history.

(56) References Cited

U.S. PATENT DOCUMENTS

| | | | | |
|---|---|---|---|---|
| 7,122,570 | B2 | 10/2006 | Koppitz et al. | |
| 7,417,026 | B2 | 8/2008 | Williams et al. | |
| 8,383,124 | B2 | 2/2013 | Zheng | |
| 9,433,663 | B2 | 9/2016 | Zheng | |
| 2006/0004032 | A1 | 1/2006 | Zheng et al. | |
| 2014/0194451 | A1 | 7/2014 | Qun et al. | |
| 2015/0297563 | A1* | 10/2015 | Geiger ................ | A61K 31/404 435/375 |
| 2022/0288020 | A1 | 9/2022 | Guo et al. | |

FOREIGN PATENT DOCUMENTS

| | | |
|---|---|---|
| EP | 2 014 651 | 1/2009 |
| WO | WO 05/017160 | 2/2005 |
| WO | WO 05/037791 | 4/2005 |
| WO | WO 09/114725 | 9/2009 |
| WO | WO 10/010027 | 1/2010 |
| WO | WO 13/166043 | 11/2013 |
| WO | WO 21/011800 | 1/2021 |

OTHER PUBLICATIONS

Han, Yang, et al. "Epigenetic age-predictor for mice based on three CpG sites." Elife 7 (2018): e37462. (Year: 2018).*
Buckinx, Fanny, et al. "Burden of frailty in the elderly population: perspectives for a public health challenge." Archives of public health 73.1 (2015): 19. (Year: 2015).*
Akunuru et al., Aug. 2016, Aging, clonality, and rejuvenation of hematopoietic stem cells, 22(8):701-712.
Cardama et al., 2017, Rho GTPases as therapeutic targets in cancer (review), International Journal of Oncology, 51(4):1026-1034.
Florian et al., Apr. 9, 2012, Cdc42 activity regulates hematopoietic stem cell aging and rejuvenation, Cell Stem Cell, 10(5):520-530.
Hong et al., 2013, Characterization of Cdc42 protein inhibitor and its use as a molecular probe, The Journal of Biological Chemistry, 288:8531-8534.
Langle et al., 2014, Small molecules targeting in vivo tissue regeneration, ACS Chemical Biology, 9:57-71.
Liu et al., 2008, Mobilization of Hematopoietic Stem/Progenitor Cells by a Cdc42 Activity-Specific Inhibitor, Blood, 112:Abstract 68.
Liu et al., 2019, Rational identification of a Cdc42 inhibitor presents a new regimen for long-term hematopoietic stem cell mobilization, Leukemia, 33:749-761.
Nur-E-Kamal et al., 1999, The CDC42-specific inhibitor derived from ACK-1 blocks v-Ha-Ras-induced transformation, Oncogene, 18:7787-7793.

(Continued)

*Primary Examiner* — Bethany P Barham
*Assistant Examiner* — Peter Anthopolos
(74) *Attorney, Agent, or Firm* — BakerHostetler

(57) ABSTRACT

Embodiments disclosed herein relate to methods for prolonging or regulating aspects of a subject's life or immunizing a subject. In particular, methods are provided for increasing or regulating longevity, survival time, life span, and health span comprising, administering to a subject in need of treatment an effective amount of at least one Cdc42-specific inhibitor. Additionally, methods are provided for immunizing a subject comprising, administering to a subject in need of immunization an effective amount of at least one Cdc42-specific inhibitor and administering to said subject one or more immunization dosages. Methods are described that further comprise identifying a subject as one that will benefit from increased longevity, increased survival time, increased life span, increased health span, or immunization. The subject is identified on the basis of the subject's age, the subject's present medical condition, the subject's present medical treatment, or the subject's Cdc42 activity.

14 Claims, 22 Drawing Sheets

(56) References Cited

OTHER PUBLICATIONS

Pelish et al., 2006, The Cdc42 inhibitor secramine B prevents cAMP-induced K+ conductance in intestinal epithelial cells Biochemical Pharmacology, 71:1720-1726.
Yang et al., Mar. 20, 2007, Rho GTPase Cdc42 coordinates hematopoietic stem cell quiescence and niche interaction in the bone marrow, PNAS, 104(12): 5091-5096.
Ye et al., Apr. 19, 2018, Identification of selective, cell active inhibitors of protein arginine methyltransferase 5 through structure-based virtual screening and biological assays, Journal of Chemical Information and Modeling, 58(5):1066-1073.
International Search Report and Written Opinion dated Nov. 25, 2020 in application No. PCT/US2020/046209.
Yang et al., Rational Targeting Cdc42 restrains Th2 cell differentiation and prevents allergic airway inflammation, Experimental Models of Allergic Disease, 2018, pp. 92-107, vol. 49(1), DOI:10.1111/cea.13293.

* cited by examiner

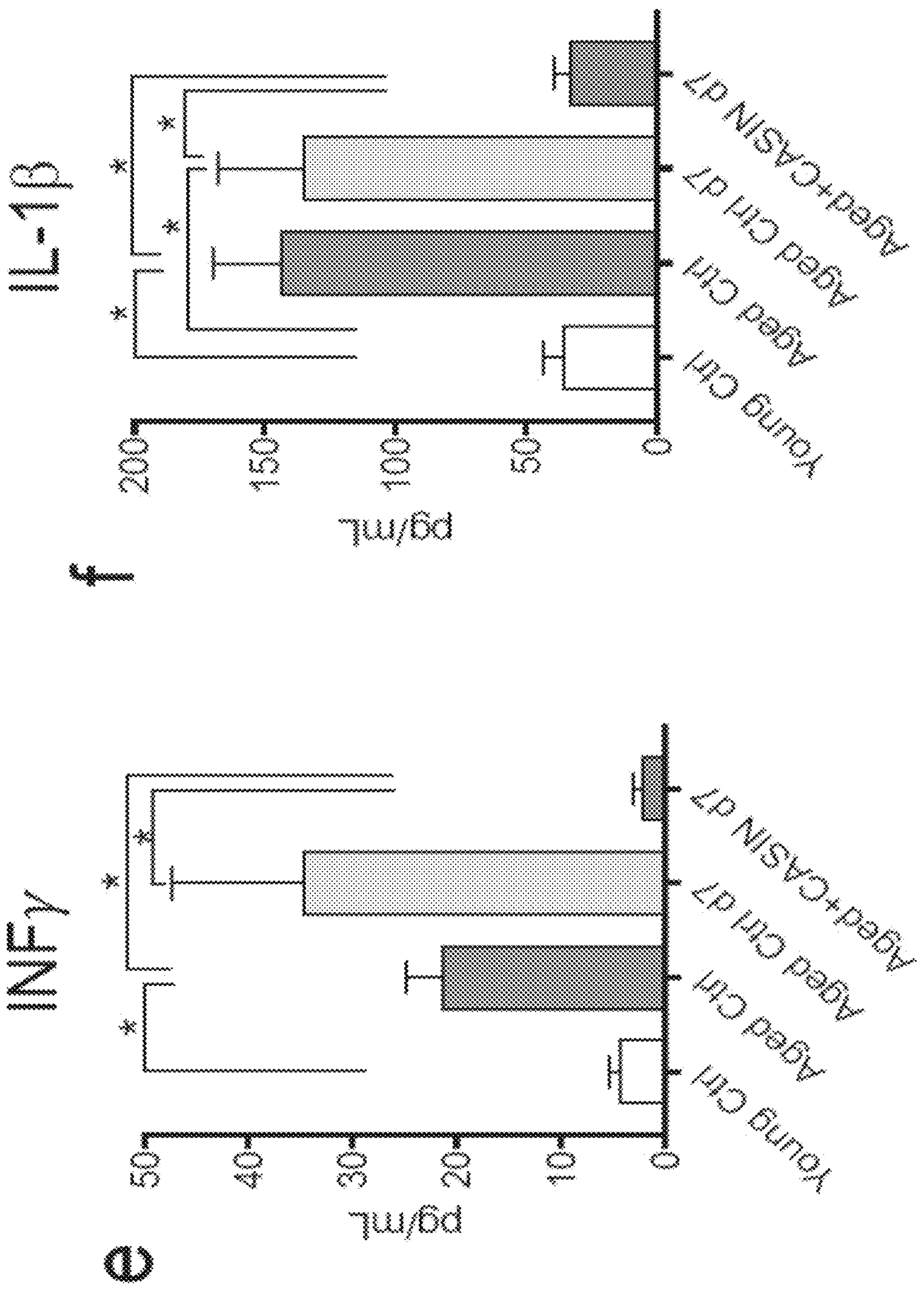
FIG. 1(e) & (f)

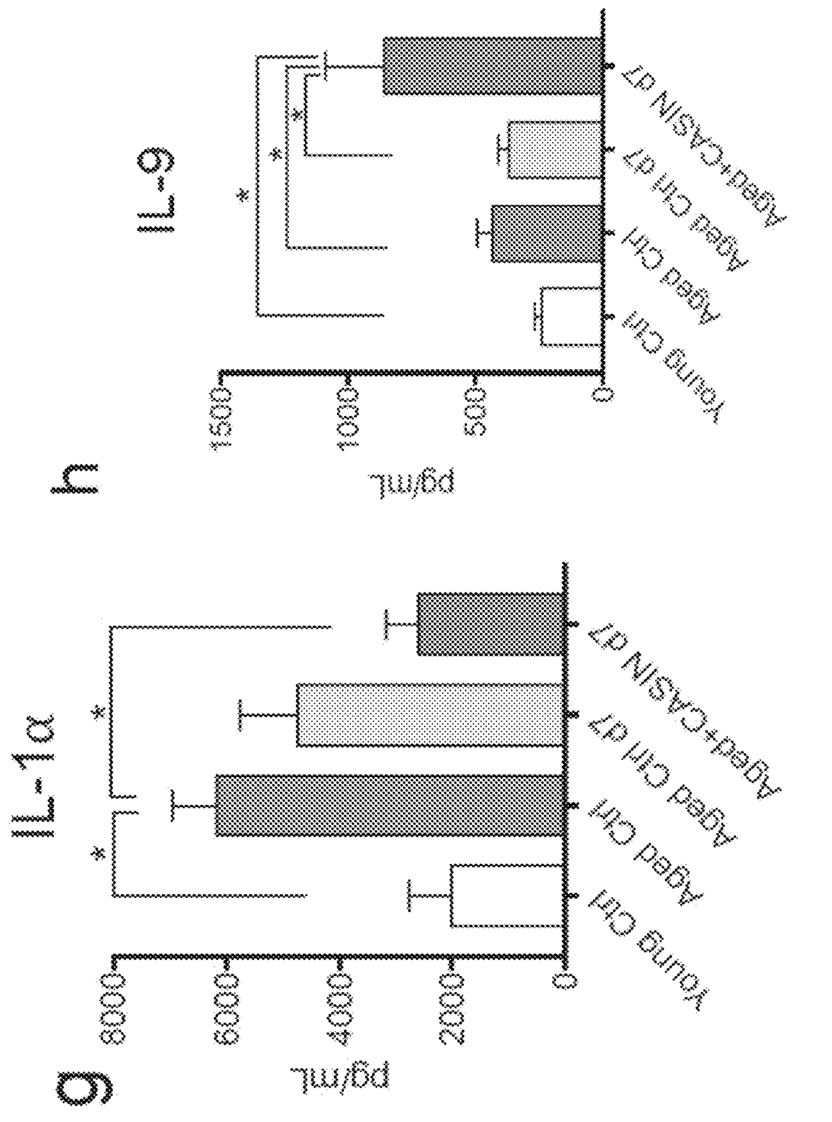
FIG. 1(g) & (h)

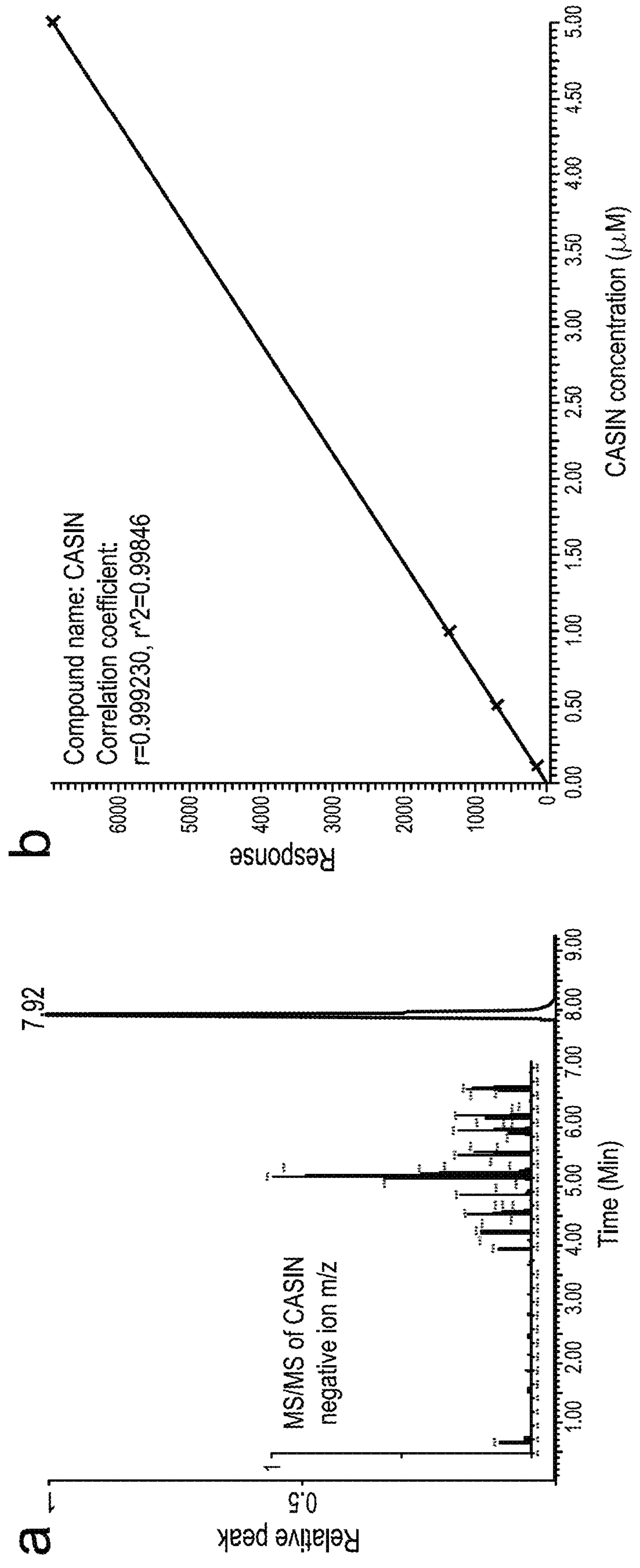
FIG. 2(a) & (b)

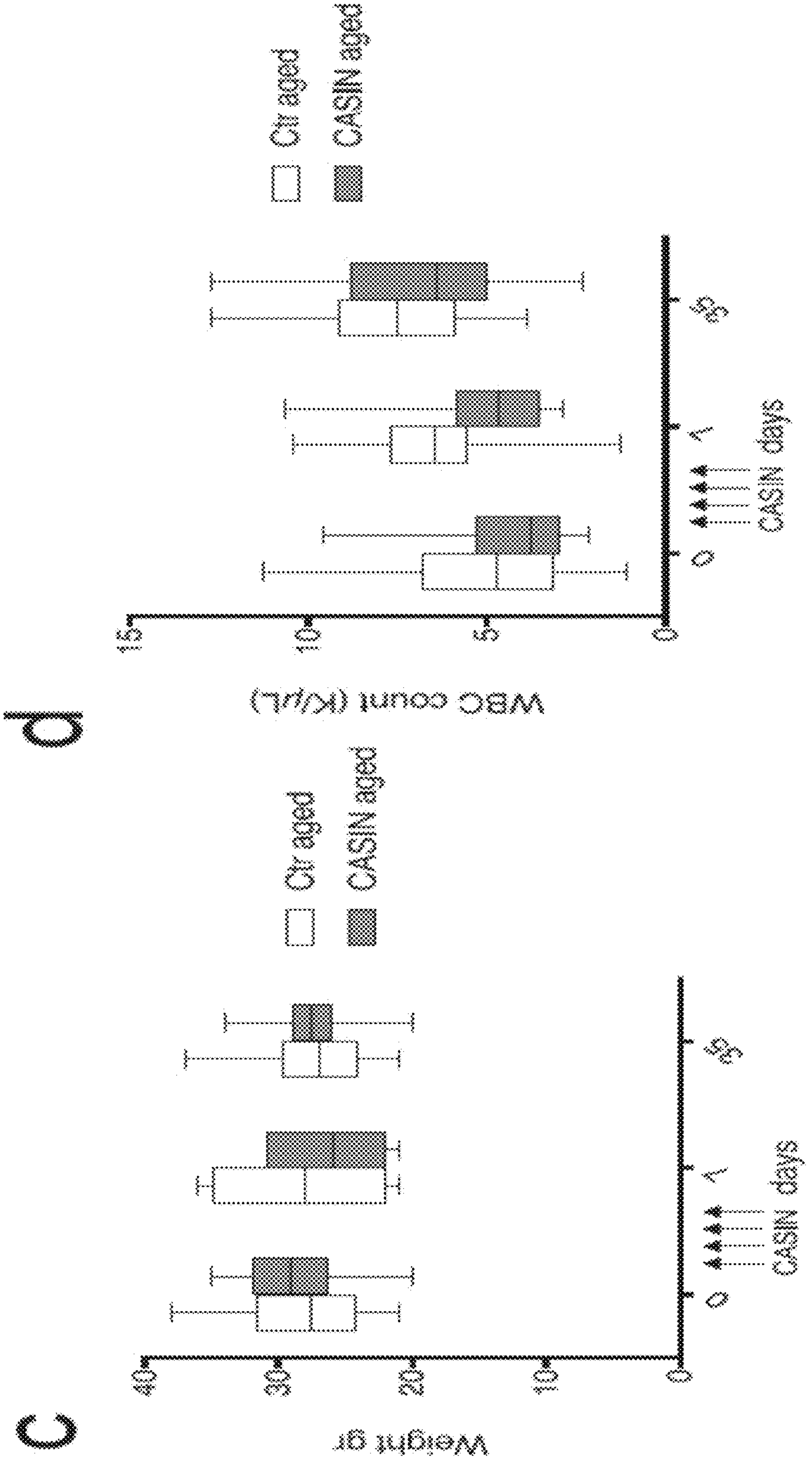
FIG. 2(c) & (d)

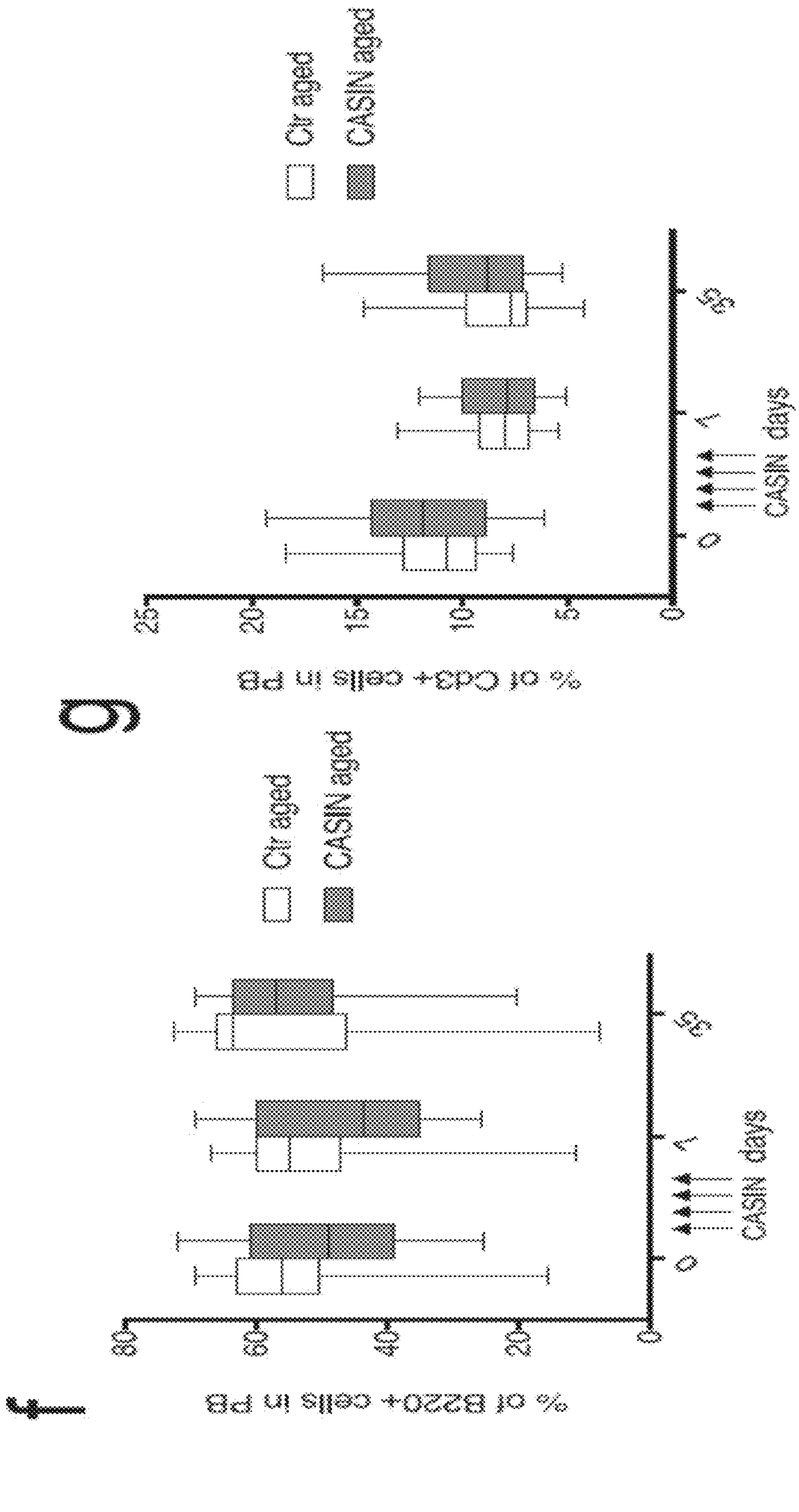
FIG. 2(f) & (g)

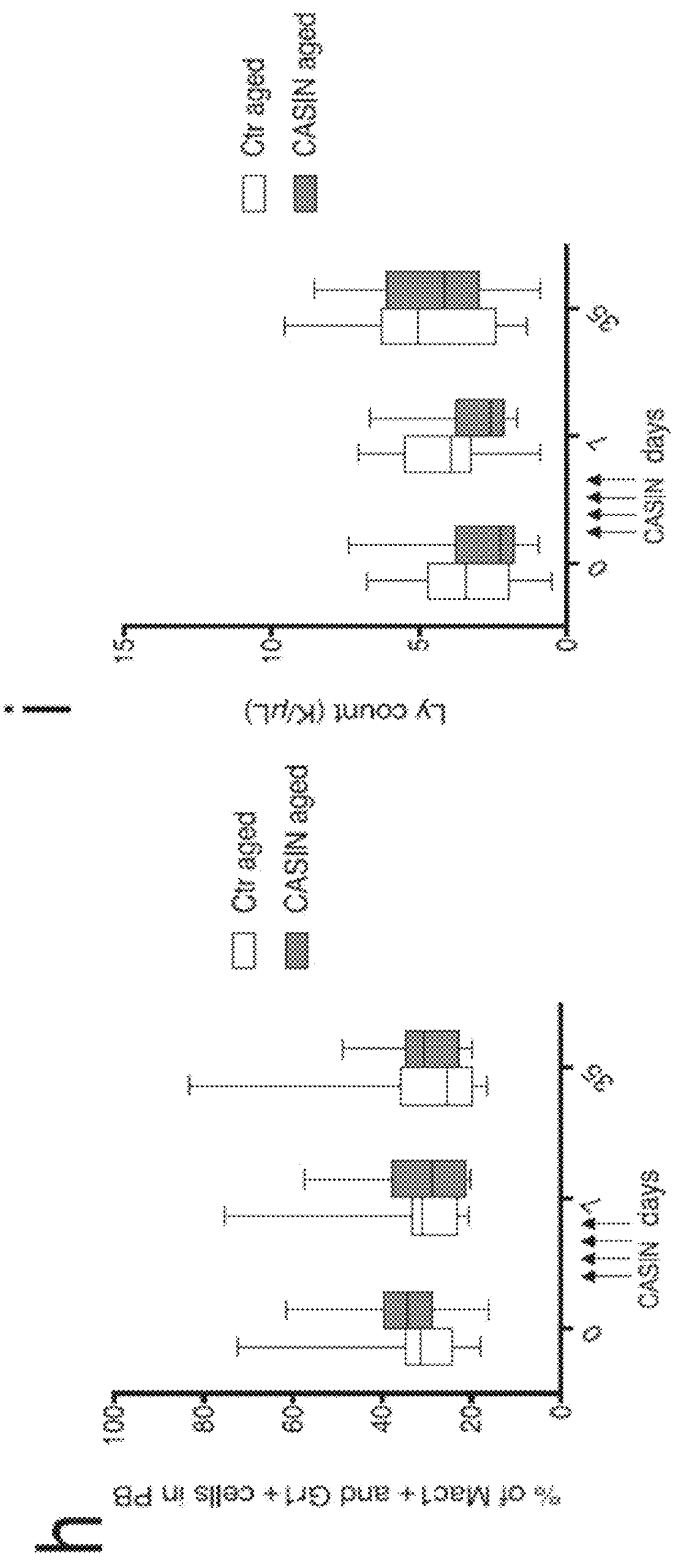
FIG. 2(h) & (i)

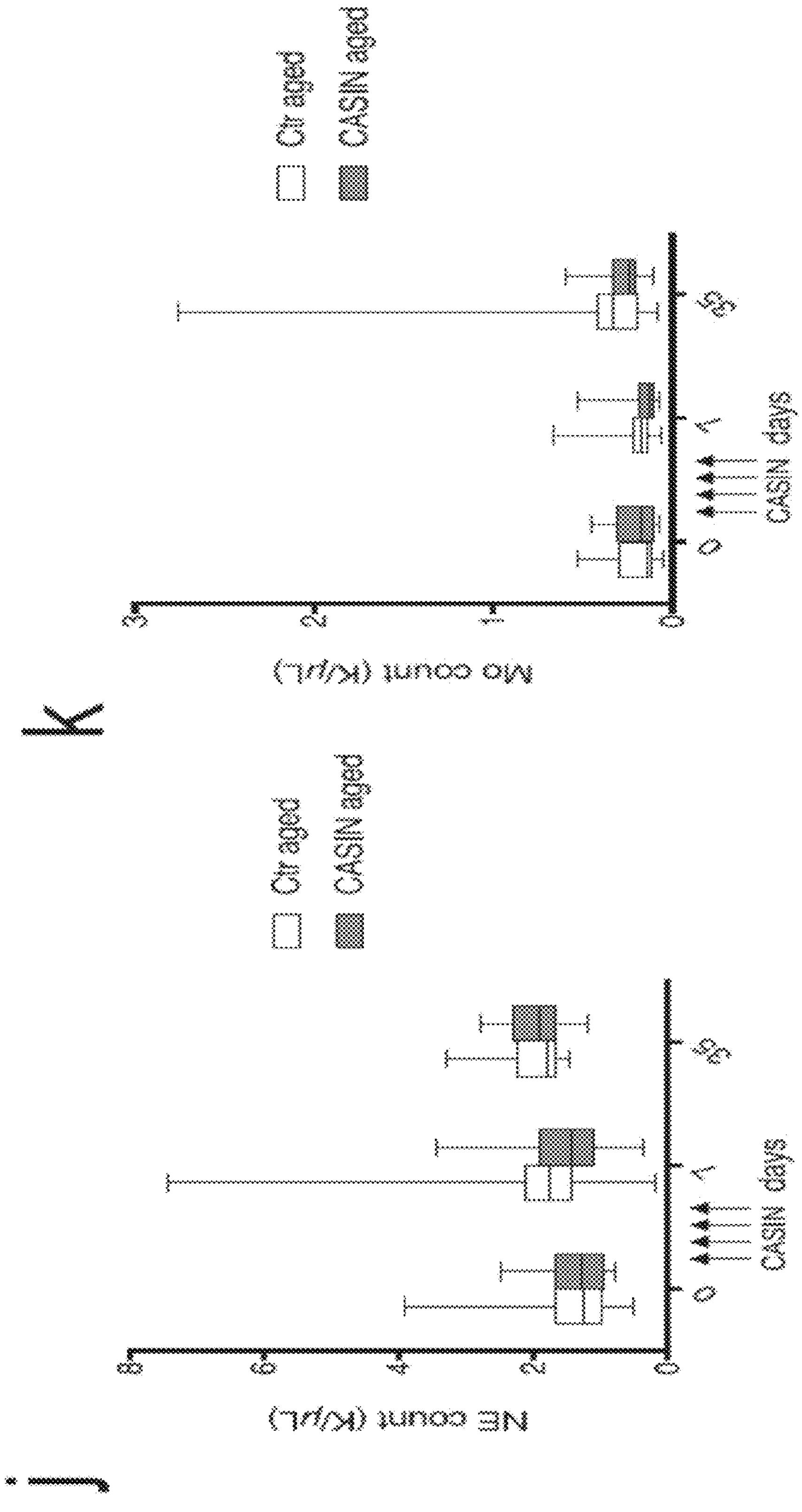
FIG. 2(j) & (k)

METHOD OF TREATING AGE-RELATED DEPRESSION AND SARCOPENIA

STATEMENT REGARDING FEDERALLY SPONSORED R&D

This invention was made with U.S. government support under grant Nos. HL076604 and DK077762 awarded by the National Institutes of Health. The U.S. government has certain rights in the invention.

BACKGROUND

Technical Field

Provided are methods for prolonging aspects of a subject's life, such as increasing longevity, survival time, life span, and health span by administration of at least one inhibitor of a GTPase, such as Cdc42 GTPase. Also provided are methods of immunizing a subject by administration of at least one inhibitor of a GTPase, such as Cdc42 GTPase, and one or more immunizations.

Description of the Related Art

Rho family GTPases are molecular switches that control signaling pathways regulating cytoskeleton reorganization, gene expression, cell cycle progression, cell survival, and other cellular processes (Etienne-Manneville, 2002), which is incorporated herein by reference in its entirety.

Rho family proteins constitute one of three major branches of the Ras superfamily. Development of inhibitors of Rho family GTPases may be a promising new avenue for new therapeutic compounds.

SUMMARY OF THE INVENTION

Embodiments disclosed herein relate to methods for prolonging aspects of a subject's life or immunizing a subject. In some embodiments, methods are provided for increasing longevity, survival time, life span, and health span comprising, administering to a subject in need of treatment an effective amount of at least one Cdc42-specific inhibitor. In some embodiments, methods are provided for immunizing a subject comprising, administering to a subject in need of immunization an effective amount of at least one Cdc42-specific inhibitor and administering to said subject one or more immunization dosages. In some embodiments, the methods further comprise identifying a subject as one that will benefit from increased longevity, increased survival time, increased life span, increased health span, or immunization. In some embodiments, the subject is identified on the basis of the subject's age, the subject's present medical condition, the subject's present medical treatment, the subject's Cdc42 activity, and/or the methylation status of CpG sites in the subject.

In some embodiments, the Cdc42-specific inhibitor is a small molecule. In some embodiments, the small molecule is Cdc42 Activity-Specific Inhibitor (CASIN). In the embodiments described herein, the chemical structure of CASIN is:

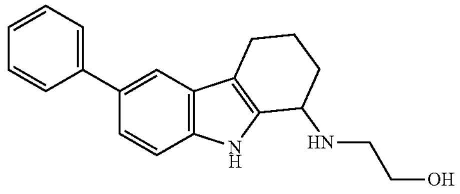 [SMILES: OCCNC1CCCc2c1[nH]c1ccc(-c3ccccc3)cc21]

In some embodiments the small molecule comprises a compound of formula (I):

(I)

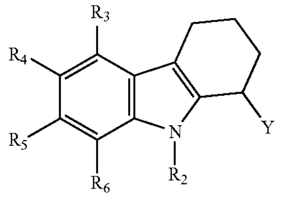

as a single enantiomer, a mixture of enantiomers, pharmaceutically acceptable salt, a solvate, or polymorph thereof, wherein:

Y is selected from the group consisting of —$OR_7$, —$NR_8R_9$, and —$NNR_8R_9$;

$R_7$ is selected from the group consisting of $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl are each optionally substituted with one or more substitutents each independently selected from the group consisting of halo, —CN, —OH, $C_{1-6}$ alkoxyl, heteroaryl, $R_{19}$, and —$OR_{20}$;

$R_8$ and $R_9$ are each separately a hydrogen or $R_{20}$; or $R_8$ and $R_9$ are optionally taken together with the nitrogen to which they are attached to form indolinyl, pyrrolidinyl, piperidinyl, piperazinyl, or morpholinyl, each optionally substituted with one or more substituents each independently selected from the group consisting of halo, cyano, nitro, hydroxy, $C_{1-6}$ alkyl, $(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro; or $R_8$ and $R_2$ come together to be $C_{1-3}$ alkyl linking together as a ring;

each $R_{20}$ separately selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of $R_{21}$ and $R_{22}$, each $R_{21}$ is separately selected from the group consisting of halo, cyano, nitro, and hydroxy, each $R_{22}$ is separately selected from the group consisting of $C_{1-6}$ alkyl, $C_{1-6}$ alkoxy —$(CH_2)_uC_{3-7}$cycloalkyl, $C_{2-6}$ alkenyl, hydroxy-$C_{1-6}$ alkyl, $R_{19}$, and —$OR_{20}$, each optionally substituted with one or more substituents each independently selected from the group consisting of halo, cyano, nitro, hydroxy, $C_{1-6}$ alkyl, and $C_{1-6}$ alkoxy;

each u is independently 0, 1, 2, 3, or 4;

$R_2$ is a hydrogen, or selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, $C_{1-6}$ alkoxy substituted with up to 5 fluoro, and —$O(CH_2)_u$phenyl optionally substituted with one or more substituents each independently selected from the group consisting of halo, cyano, nitro, hydroxy, $C_{1-6}$ alkyl, and $C_{1-6}$ alkoxy; or $R_8$ and $R_2$ come together to be $C_{1-3}$ alkyl linking together as a ring;

$R_3$, $R_4$, $R_5$ and $R_6$ are each independently selected from the group consisting of hydrogen, halo, cyano, nitro, hydroxy, $C_{1-6}$ alkyl, $(CH_2)_uC_{3-7}$cycloalkyl, —$O(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH_2)_uC_{3-7}$cycloalkyl, —$O(CH_2)_uC_{3-7}$cycloalkyl, $C_{2-6}$ alkenyl, $C_{1-6}$ alkoxy, hydroxy-$C_{1-6}$ alkyl, and phenyl, each optionally substituted with one or more $R_{23}$, each $R_{23}$ is independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

each $R_{19}$ is independently aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

each $R_{20}$ is independently hydrogen or aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro; and wherein when Y is $NR_8R_9$ then $R_8$ and $R_2$ optionally come together to be $C_{1-3}$ alkyl linking together as a ring, with the proviso when $R_8$ comes together with $R_2$ to be $C_{1-3}$ alkyl linking together as a ring then $R_4$ is not substituted with hydroxyl.

Also presented herein is a method of immunizing a subject, wherein the Cdc42-specific inhibitor is administered to the subject prior to said subject receiving one or more immunization dosages. In some embodiments, the Cdc42-specific inhibitor is administered to the subject after said subject receives one or more immunization dosages. In some embodiments, the Cdc42-specific inhibitor is administered to the subject both before and after said subject receives one or more immunization dosages. In some embodiments, the administering of the Cdc42-specific inhibitor to said subject occurs once or more than once. In some embodiments, the subject is administered one or more immunization dosages for the same disease or different diseases. In some embodiments, the subject's immune system is compromised. In some embodiments, the Cdc42 activity in the subject is determined prior to administering the Cdc42-specific inhibitor to said subject.

Also presented herein is a method for increasing longevity, survival time, life span, and health span comprising, administering to a subject in need of treatment an effective amount of at least one Cdc42-specific inhibitor, wherein the expected increase in longevity, survival time, life span, and/or health span is about 1%-100%, about 1%-90%, about 1%-80%, about 1%-70%, about 1%-60%, about 1%-50%, about 1%-40%, about 1%-30%, about 1%-20%, about 5%-15%, about 5%, about 6%, about 7%, about 8%, about 9%, about 10%, about 11%, about 12%, about 13%, about 14%, about 15%, or a range bounded by any of the aforementioned numbers, percentages being relative to the expected longevity, survival time, life span, or health span of the subject. In some embodiments, the expected longevity, survival time, life span, or health span of the subject is the median or mean expectation for similarly situated subjects. In some embodiments, the expected increase is statistically significant.

DETAILED DESCRIPTION

Figure 1A:
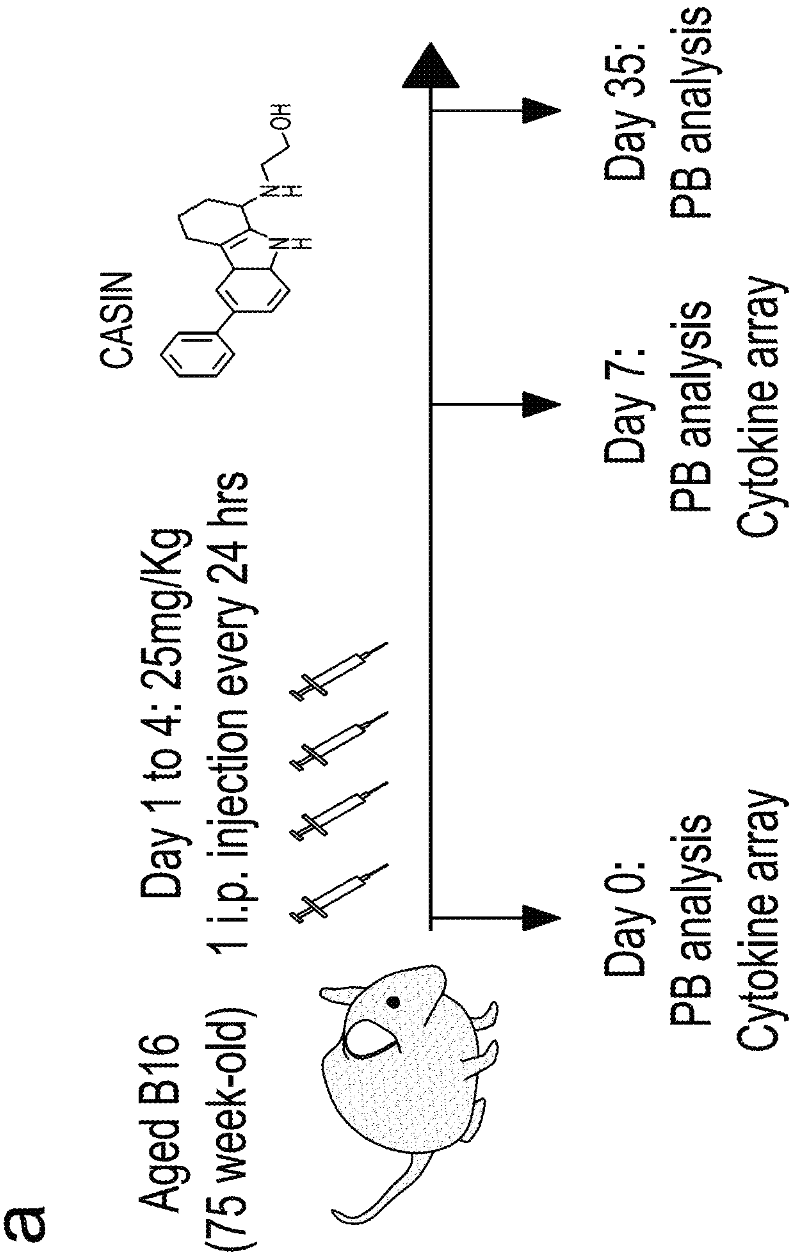
FIG. 1. (a) Scheme depicting the experimental set-up for an in vivo model determining the effect of a Cdc42-specific inhibitor (e.g., CASIN) on a mammal's lifespan; (b) Quantification by mass spectrometry of Cdc42-specific inhibitor concentration (e.g., CASIN) in serum over time in 75-week old C57BL/6 mice injected with a i.p. dose of 25 mg/Kg of CASIN for 4 consecutive days every 24 hours. The blood was harvested 3, 24 and 48 hours after the last injection on day 4. n=26 for the 3 hr time point, 12 for the 24 hr time point and 7 for the 48 hr time point. (c) Representative image and quantification of western blot/pulldown of Cdc42 total and active (Cdc42GTP) in bone marrow cells from young (10 week old, denoted "Ctrl young") and aged (75 week old, denoted "Ctrl Aged") control and CASIN treated (denoted "CASIN aged") C57BL/6 mice. n=4 mice per group; * $p<0.05$ vs aged control according to one-way ANOVA analysis and Tukey's multiple comparisons test; (d) Survival curve for aged control (denoted "Aged Ctr" and represented by the black line diverging at approximately week 75 and terminating on the X-axis between weeks 120 and 135) and CASIN (denoted "Aged CASIN" and represented by the gray line diverging at approximately week 75 and terminating on X-axis between weeks 150 and 165) treated mice. Treatment was done accordingly to the cartoon scheme depicted in panel a. n=18 for control and 17 for CASIN; $p<0.0004$ according to Mantel-Cox test and $p<0.0032$ according to Gehan-Breslow-Wilcoxon test. Median survival for control 123.5 weeks and 136 weeks for CASIN; (e)-(h) Results from the cytokine array. Serum was collected from the same mice at day 0 (aged control) and day 7 (aged control and aged CASIN, denoted in the graphs with the addition descriptor "d7") according to the scheme in panel a. 7 young (10-week old) C57BL/6 female mice were bled together with the old mice at day 0 and the serum was used for the cytokine array young control sample. The number of experimental mice included was n=7 for young control (denoted "Young Ctrl"), 27 for aged control day 0 (denoted "Aged Ctrl"), 9 for aged control day 7 (denoted "Aged Ctrl d7"), and 10 for aged CASIN day 7 (denoted "Aged+CASIN d7"). The serum samples were loaded simultaneously for all cytokines probed and all experimental arms. Some samples did not generate a signal above the background due to technical reasons and were excluded from the statistical analysis. Bars represent mean+/−SEM. *$p<0.05$; **$p<0.01$ according to one-way ANOVA analysis and Tukey's multiple comparisons test; (i) Biological age prediction as based on DNA methylation profile of blood cells from aged control and aged CASIN-treated mice 8-9 weeks after treatment. The experiment was repeated twice with a cohort of 5-6 animals per group (n=12 for control and 11 for CASIN). Bars represents mean+/−SEM. *$p<0.05$ according to unpaired t-test analysis. For each of the aged control ("Aged Ctrl") and "Aged CASIN" the bar graph for "Biological Age" is provided on the left and the bar graph for "Chronological Age" is provided on the right such that there was a difference of approximately 9 weeks between the biological age and the chronological age for the "Aged CASIN" group.
Figure 1B:
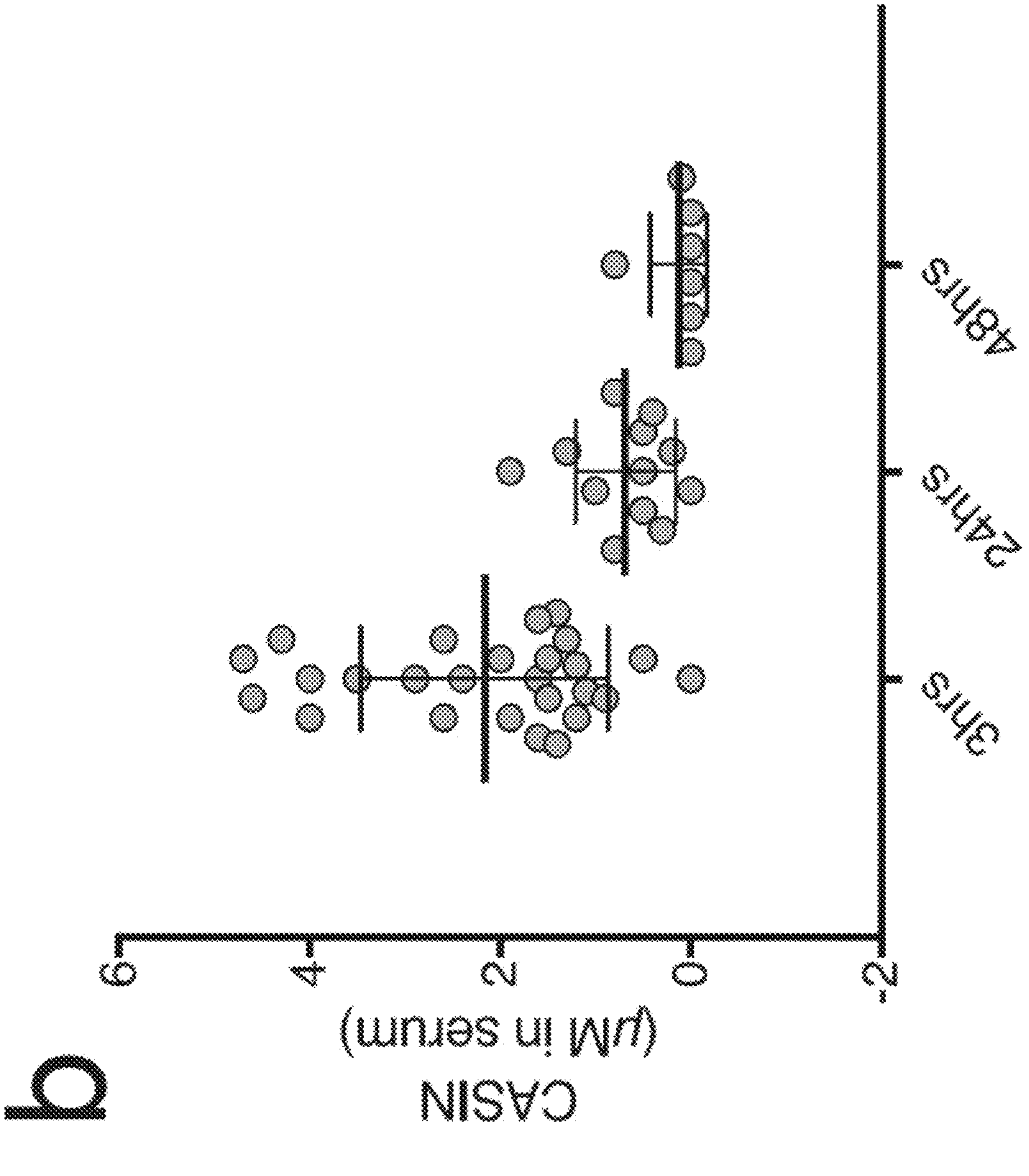

Aging-associated remodeling of the immune system impairs its functional integrity and contributes to increased morbidity and mortality in the elderly.

The phenotypic and functional changes in the immune system on aging are primarily a consequence of changes in the function of hematopoietic stem cells (HSCs) on aging. Aging of HSCs is, in part, driven by elevated activity of the small RhoGTPase CDC42. Until recently, there was broad consensus that the phenotype of aged HSCs is fixed and dominated by cell-intrinsic regulatory mechanisms that could not be reverted by therapeutic intervention. However, new research suggests a novel and critical mechanistic role for Cdc42 activity in HSC aging, identifying Cdc42 activity as a pharmacological target for ameliorating HSC aging. Accordingly, pharmacological inhibition of the elevated Cdc42 activity in aged HSCs may rejuvenate aged HSCs.

Cdc42 is involved in multiple and diverse functions of eukaryotic cells, including actin cytoskeleton reorganization, cell polarity and cell growth. Cdc42 cycles between an inactive, GDP-bound state, and an active, GTP-bound state. The cycling between the GDP-bound form and the GTP-bound form is tightly controlled by a number of different regulatory proteins, and its activity, and thus the level of Cdc42-GTP, is significantly elevated in the blood of elderly animals (e.g., humans) and in several tissues of aged C57BL/6 animals, including heart, brain, lung, liver, bone marrow, spleen, and kidney. Cdc42 GTPase-activating protein (Cdc42GAP; also known as p50RhoGAP or ARHGAP1) is a ubiquitously expressed negative regulator of Cdc42 that catalyzes hydrolysis of GTP bound to Cdc42. Genetic deletion of Cdc42GAP in mice (Cdc42GAP knock out) results in an elevated level of Cdc42-GTP in every tissue. This constitutive increase of Cdc42 activity in young mice leads to a premature aging-like phenotype that affects several tissues and results in a decrease in lifespan.

Presented herein is the surprising discovery that exposing a subject to a Cdc42-specific inhibitor can regulate or increase a subject's longevity, survival time, life span, and/or health span, as well as re-establish an immune system having the ability to mount a strong immune response to vaccination. These, and other novel aspects, are described in further detail below.

As described herein, it is intended that where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the embodiments, subject to any specifically excluded limit in the stated range. Where the stated range includes one or both of the limits, ranges excluding either both of those included limits are also included in the embodiments. It is further intended that when a series of whole integers are reported for any particular value, e.g., 1, 2, 3, 4, 5, 6, etc., a range may be enumerated from any of the aforementioned whole integers, e.g., 1-6, 2-6, 3-5, 1-4, etc.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described. All publications mentioned herein are expressly incorporated by reference in their entireties.

As used herein and in the appended claims, the singular forms “a,” “and,” and “the” include plural referents unless the context clearly dictates otherwise. Thus, for example, reference to “a method” includes a plurality of such methods and reference to “a dose” or “dosage” includes reference to one or more doses and equivalents thereof known to those skilled in the art, and so forth.

In some contexts, the terms “individual,” “host,” “subject,” and “patient” are used interchangeably to refer to an animal that is the object of treatment, observation and/or experiment. “Animal” includes vertebrates and invertebrates, such as fish, shellfish, reptiles, birds, and, in particular, mammals. “Mammal” includes, without limitation, mice, rats, rabbits, guinea pigs, dogs, cats, sheep, goats, cows, horses, primates, such as monkeys, chimpanzees, and apes, and, in particular, humans.

The term “about” or “approximately” means within an acceptable error range for the particular value as determined by one of ordinary skill in the art, which will depend in part on how the value is measured or determined, e.g., the limitations of the measurement system. For example, “about” can mean within 1 or more than 1 standard deviations, per the practice in the art. Alternatively, “about” can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term “about” meaning within an acceptable error range for the particular value should be assumed.

As used herein, the term “heterologous sequence or gene” means a nucleic acid (RNA or DNA) sequence, which is not naturally found in association with the nucleic acid sequences of the specified molecule. The sections below provides greater detail on some approaches that can be used to prepare inhibitors of Cdc42.

Increasing Methods

Embodiments disclosed herein relate to administering to a subject in need of treatment an effective amount of at least one Cdc42-specific inhibitor. Specific methods described herein relate to methods for increasing longevity, increasing survival time, increasing lifespan, or increasing health span in a subject comprising administering to a subject in need of treatment an effective amount of at least one Cdc42-specific inhibitor.

“Longevity” refers to the time a subject is expected to live, based on the year of its birth, and its current age. It may further include subject-specific demographics or determinants such as gender, genetics, lifestyle (such as smoking, physical exercise, activity in everyday life, alcohol consumption, diet, self-care practices, social contacts and workstyle), culture, politics, religion, and socioeconomics. See, e.g., “Men, Ageing and Health,” (2001), 01/WHO/NMH/NPH 01.2

“Survival time” refers to the expected duration of time until death of a subject. It may further include subject-specific demographics or determinants such as gender, genetics, lifestyle, culture, politics, religion, and socioeconomics.

“Lifespan” refers to the expected duration of life that a subject has remaining at a given age. It may further include subject-specific demographics or determinants such as gender, genetics, lifestyle, culture, politics, religion, and socioeconomics.

“Health span” refers to the expected length of time in a subject’s life during which a subject is in reasonably good health. In some embodiments, a subject’s health considers one or more of physical, mental, social-well-being, absence of disease, and absence of infirmity.

The “increase” referred to in the disclosed embodiments refers to an “expected increase” for the subject as opposed to the actual increase any particular subject experiences. Thus, one does not need to wait for a subject’s longevity, survival time, life span, or health span to expire in order to practice the disclosed embodiments. Expected increases may be statistically significant or insignificant, though in preferred embodiments any expected increase is statistically significant. There are many methods known for calculating statistical significance, e.g., calculating a “p-value.” In some embodiments, the threshold for statistical significance is a p-value≤0.2, ≤0.15, ≤0.1, ≤0.05, ≤0.01, ≤0.005, about ≤0.2, about ≤0.15, about ≤0.1, about ≤0.05, about ≤0.01, or about ≤0.005. Sometimes, a result may not be statistically significant but yet the result is still informative or suggestive of some conferred benefit. It is understood that the degree of significance one would ascribe to a particular result is within the ken of the ordinarily skilled physician.

In some embodiments, the expected longevity, survival time, life span, or health span of the subject is the median expectation for similarly situated subjects. In other embodiments, the expected longevity, survival time, life span, or health span of the subject is the mean expectation for similarly situated subjects. Subjects of similar situation may be determined based upon any one or more factors, including but not limited to, age, health, family history, or Cdc42 activity levels.

The expected increase may be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), relative to the expected longevity, survival time, life span, or health span of the subject.

In some embodiments, the expected increase is in years and is 1-20 years, 1-19 years, 1-18 years, 1-17 years, 1-16 years, 1-15 years, 1-14 years, 1-13 years, 1-12 years, 1-11 years, 1-10 years, 1-9 years, 1-8 years, 1-7 years, 1-6 years, 1-5 years, 1-4 years, 1-3 years, 1-2 years, 1 year, at least the aforementioned years (e.g., at least 1-10 years), or about the aforementioned years (e.g., about 1-2 years or at least about 1-2 years), relative to the expected longevity, survival time, life span, or health span of the subject.

In some embodiments the expected increase is in days to months, and is one day to one year, one day to 11 months, one day to 10 months, one day to 9 months, one day to 8 months, one day to 7 months, one day to 6 months, one day to 5 months, one day to 4 months, one day to 3 months, one day to 2 months, one day to one month, at least the aforementioned range of days to months (e.g., at least one day to 11 months), or about the aforementioned range of days to months (e.g., about one day to 6 months or at least about one day to 6 months), relative to the expected longevity, survival time, life span, or health span of the subject.

In some embodiments the expected increase is in weeks and is 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, about any of the aforementioned weeks (e.g., about 15 weeks), at least about any of the aforementioned weeks (e.g., at least about 15 weeks), or a range bounded by any two of the aforementioned weeks (e.g., 2-30 weeks or about 2-30 weeks, or at least about 2-30 weeks), 1-52 weeks, 2-50 weeks, 3-45 weeks, 4-40 weeks, 5-35 weeks, 6-30 weeks, 5-25 weeks, 6-20 weeks, 7-19 weeks, 8-18 weeks, 9-17 weeks, 10-16 weeks, 11-15 weeks, 12-14 weeks, at least the aforementioned range of weeks (e.g., at least 6-20 weeks), or about the aforementioned range of weeks (e.g., about 6-20 weeks or at least about 6-20 weeks), relative to the expected longevity, survival time, life span, or health span of the subject.

In some embodiments the expected increase is in days and is 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days about any of the aforementioned days (e.g., about 15 days), at least about any of the aforementioned weeks (e.g., at least about 15 days), or a range bounded by any two of the aforementioned weeks (e.g., 2-30 days or about 2-30 days, or at least about 2-30 days), relative to the expected longevity, survival time, life span, or health span of the subject.

The "decrease" or "reduction" referred to in the disclosed embodiments refers to the "actual" or "expected" decrease or reduction. Actual or expected decreases or reductions may be statistically significant or insignificant, though in preferred embodiments any decrease or reduction is statistically significant. There are many methods known for calculating statistical significance, e.g., calculating a "p-value." In some embodiments, the threshold for statistical significance is a p-value≤0.2, ≤0.15, ≤0.1, ≤0.05, ≤0.01, ≤0.005, about ≤0.2, about ≤0.15, about ≤0.1, about ≤0.05, about ≤0.01, or about ≤0.005. Sometimes, a result may not be statistically significant but yet the result is still informative or suggestive of some conferred benefit. It is understood that the degree of significance one would ascribe to a particular result is within the ken of the ordinarily skilled physician.

Immunization Methods

Embodiments disclosed herein relate to administering to a subject in need of immunization an effective amount of at least one Cdc42-specific inhibitor and administering to the subject one or more immunization dosages. Surprisingly, direct pharmacological intervention of a Cdc42-specific inhibitor in a subject allows for a strong immunization response upon challenge with an immunogen. Such direct administration obviates any need to obtain and purify HSCs from compatible donors, pre-treat the HSCs with a Cdc42-specific inhibitor, and transplant the treated, donor HSCs into a transplant recipient. Thus, under some of the embodiments disclosed herein, the Cdc42-specific inhibitor essentially acts as a type of adjuvant, enhancing the efficacy of an immunization by modifying a subject's immune system and immune response. In some embodiments, the Cdc42-specific inhibitor is combined with the immunization dosage prior to administering to a subject (e.g., the subject receives one or more immunization dosages that contain both an immunogen and a Cdc42-specific inhibitor). In some embodiments, the immunization dosage and Cdc42-specific inhibitor are administered in separate dosages to the subject.

In some embodiments, the Cdc42-specific inhibitor is administered to the subject prior to the subject receiving one or more immunization dosages. In other embodiments, the Cdc42-specific inhibitor is administered to the subject concurrent with the subject receiving one or more immunization dosages. Concurrent administration can be effected by multiple administrations within a limited period of time (e.g., a single office visit with a physician) or concurrent administration can be effected simultaneously or nearly simultaneously.

A subject in need of receiving a Cdc42-specific inhibitor to improve an immune response need not always be identified prior to receive a first immunization. For example, a subject might be identified by exhibiting a poor response to a first attempted immunization. According, in some embodiments, the Cdc42-specific inhibitor is administered to the subject after the subject receives one or more immunization dosages.

Often, a subject does not receive sufficient immunity from a single immunization dose and is required to receive multiple immunization dosages before sufficient immunity is conferred. One can readily and immediately envision a regimen wherein a subject is administered a first Cdc42-specific inhibitor, the subject receives a first immunization dosage after the administration of the first Cdc42-specific inhibitor, and the subject receives one or more subsequent immunization dosages after the subject receives the first immunization dosage. Such a regimen may continue such that the subject receives a third immunization dosage after the subject receives the second immunization dosage. Thus, a subject may receive 1-10, 1-9, 1-8, 1-7, 1-6, 1-5, 1-4, 1-3, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, or 2, 3, 4, 5, 6, 7, 8, 9, or 10 total immunization dosages for immunization against an individual disease. One or more Cdc42-specific inhibitors may be administered before the first immunization dosage, or before one or more subsequent immunization dosages.

Often, a subject requires immunization against more one or more diseases (e.g., a subject is immunized against multiple diseases throughout childhood or adulthood). This could be due to the subject's health, upcoming travel, or due to the omission of immunization during the subject's childhood. One or more Cdc42-specific inhibitors may be administered before the first immunization dosage, or before one or more subsequent immunization dosages when the subject is being immunized for one or more diseases, or even multiple diseases. Just as the first and subsequent immunization dosages may be the same or different (e.g., in either strength, concentration, or immunogen), the one or more Cdc42-specific inhibitors that are administered to the subject may be the same or different.

In some instances, a period of time passes between administering an immunization dosage to a subject. In some embodiments, the time period between immunization dosages is about 1 week, about 2 weeks, about 3 weeks, about 1 month, about 2 months, about 3 months, about 4 months, about 5 months, about 6 months, about 7 months, about 8 months, about 9 months, about 10 months, about 11 months, or about 1 year. In some embodiments, one or more Cdc42-specific inhibitors are administered to the subject during the period between the subject's administrations of an immunization dosage.

Subjects benefitting from administration of a Cdc42-specific inhibitor in the course of immunization may have a healthy immune system. Alternatively, in some embodiments the subject does not have a healthy immune system. The subject's immune system may be compromised, particularly an immune system compromised by the subject's age, by the subject's medical condition, or by treatment of the subject for the subject's medical condition.

Unless otherwise specified, the full breadth of the term "immunization" is intended for the methods disclosed herein. Immunization may be passive or active. Passive immunization is where pre-synthesized elements of the immune system are transferred to a person so that the body does not need to produce these elements itself. Antibodies can be used for passive immunization. Active immunization can occur naturally when a person is contacted with a microbe, attenuated or otherwise, or a person is contacted with a part of a microbe. However, the immunogen need not be a microbe and, for example, in some embodiments the immunogen is a small molecule (e.g., nicotine) or a large molecule (e.g. a protein, such as a cancer protein, or a hormone, such as ghrelin).

The immunization dosage may also be a vaccine, though as discussed above an immunization dosage is not necessarily so limited. Thus, in some embodiments, the immunization dosage is not a vaccine. Many vaccines are recommended by the World Health Organization or the Centers for Disease Control and Prevention. In some embodiments, the immunization dosage is a vaccine that is recommended by the medical community. In some embodiments, the vaccine is recommended by the Centers for Disease Control and Prevention. The vaccine may also be recommended by the World Health Organization, the Centers for Disease Control and Prevention, or the medical community for administration to adults. In some embodiments, the vaccine is for a disease that disproportionately affects adults as compared to children. In some embodiments, the vaccine is for a disease such as one or more of influenza, pertussis, tetanus, diphtheria, shingles, pneumococcal disease, human papillomavirus, meningococcal disease, hepatitis A, hepatitis B, chickenpox, measles, mumps, and rubella.

Subject Identification

Embodiments disclosed herein relate to administering to a subject in need of treatment an effective amount of at least one Cdc42-specific inhibitor, which includes modulators of Cdc42-specific activity. In some embodiments, not every subject is a candidate for such administration and identification of treatment subjects may be desirable. It is understood that patient selection depends upon a number of factors within the ken of the ordinarily skilled physician. Thus, some embodiments disclosed herein further comprise identifying a subject as one that will benefit from administering an effective amount of at least one Cdc42-specific inhibitor to increase longevity, increase survival time, increase life span, or improve upon immunization. Subjects may be identified on the basis of physiological factors specific to the subject according to the subject's age, present medical condition, present medical treatment, prescribed medical treatment, methylation status of CpG sites within any of the subjects Prima1, Hsf4, or Kcns1 genes, or any combination thereof, or in preferred embodiments, on the basis of the subject's Cdc42 activity. Assays for determining a subject's Cdc42 activity, particularly in measuring such activity in a subject's blood sample, are known in the art. See, e.g., Mizukawa et al., Blood (2017) 130:1336-46.

In some embodiments, a physician may rely on a combination of physiological factors for a given subject to identify a subject for treatment with an effective amount of at least one Cdc42-specific inhibitor. As noted above, the subject's age may be a factor in identifying a subject in need of treatment. For example, the subject may be elderly (e.g., an elderly human subject). An elderly human subject, in some embodiments described herein, is a subject having an age that is equal to or older than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 years old, or a range bounded by any of the aforementioned ages (e.g., an age that is equal to or older than 50-80, 50-70, 50-60, 55-75, 55-75, 55-70, 55-65, 60-70, 52-71, 60-79, or 73-78 years old).

In some embodiments, as discussed supra, the subject is a human. However, the methods are not limited to the treatment of humans and are equally applicable to the treatment of mammals. In such instances of treating non-human mammals, patient selection depends upon a number of factors within the ken of the ordinarily skilled veterinarian or research scientist Cdc42-Specific Inhibitors Embodiments disclosed herein relate to compounds, compositions, pharmaceutical compositions, methods, uses, and kits that comprise at least one Cdc42-specific inhibitor. In some embodiments, the Cdc42-specific inhibitor can be a chemical inhibitor such as a small molecule (e.g., CASIN). Small molecules include, for example, chemical molecules with a low molecular weight (e.g. a molecular weight below 2000 daltons). Additionally, the Cdc42-specific inhibitor can be an siRNA molecule, an antisense molecule, a small RNA (e.g., a micro RNA) or modified nucleic acid, a ribozyme, an antibody (such as a neutralizing antibody), or a polypeptide (e.g., a dominant negative peptide). Any type of inhibitor which is known to one of skill in the art may be used.

Another aspect of the embodiments relates to the regulation of biological pathways in which a GTPase is involved. Thus, some embodiments relate to all aspects of modulating an activity of a Cdc42 GTPase comprising, administering an effective amount of an active agent, an effective amount of a compound which specifically and/or selectively modulates the activity of a Cdc42 GTPase, or combination thereof. The activity of Cdc42 which is modulated can include: GTP binding, GDP binding, GEF binding, GTPase activity, integrin binding, coupling or binding of Cdc42 to receptor or effector-like molecules (such as integrins, growth factor receptors, tyrosine kinases, PI-3K, PIP-5K, etc.). Increasing, reducing, antagonizing, or promoting Cdc42 can modulate the activity. The modulation of Cdc42 can be measured by assay for GTP hydrolysis, binding to GEF, etc. An effective amount is any amount which, when administered, modulates the Cdc42 activity. The activity can be modulated in a cell, a tissue, a whole organism, in situ, in vitro (test tube, a solid support, etc.), in vivo, or in any desired environment. In some embodiments, the effective amount of a Cdc42-specific inhibitor is one that restores Cdc42 activity to a normal level in the subject. In some embodiments, the effective amount of a Cdc42-specific inhibitor is one that reverses tublin apolarity in a cell, inhibits Cdc42 activity in a blood precursor cell, such as a hematopoietic cell, progenitor cell, or a stem cell. In some embodiments, the effective amount of the Cdc42-specific inhibitor does not mobilize a blood precursor cell.

Other assays for Cdc42-mediated signal transduction can be accomplished according to procedures known in the art, e.g., as described in U.S. Pat. Nos. 5,141,851; 5,420,334; 5,436,128; and 5,482,954, all of which are incorporated herein by reference in their entirety where permitted. In addition, peptides that inhibit the interaction, e.g., binding, between an active agent and a G-protein, such as Cdc42, can be identified.

Methods for detecting inhibition of Cdc42 activity are known in the art, as exemplified by the Active Cdc42 pull-down and detection kit available from Thermo Fisher Scientific Inc. (Rockford, Ill.), as described in the Example section below, and by the incorporated materials of Asnaghi et al., Oncogene (2010) 29:2760-2771. Detecting inhibition may include comparing the inhibitory properties of a compound being tested to the inhibitory properties of one or more reference compounds. Such a reference compound can be, for example, CASIN or other compounds described herein.

By modulating, it is meant that addition of the agent affects the activity or binding. The binding or activity modulation can be affected in various ways, including inhibiting, blocking, preventing, increasing, enhancing, or promoting it. The binding or activity effect does not have to be achieved in a specific way, e.g., it can be competitive, noncompetitive, allosteric, sterically hindered, via cross-linking between the agent and the GEF or GTPase, etc. The agent can act on either the active agent or GTPase. The agent can be an agonist, an antagonist, or a partial agonist or antagonist. The presence or amount of binding can be determined in various ways, e.g., by assaying for an activity promoted or inhibited by the active agent, such as guanine nucleotide exchange, GTP hydrolysis, oncogenic transformation, etc. Such assays are described above and below, and are also known in the art. The agent can be obtained and/or prepared from a variety of sources, including natural and synthetic. It can comprise, e.g., amino acids, lipids, carbohydrates, organic molecules, nucleic acids, inorganic molecules, or mixtures thereof.

Detecting modulation can be performed in vitro or in vivo as will be understood in the art. Examples of in vitro and in vivo methods are provided herein. The results from evaluating the inhibitory properties of the compounds provided herein can be reported in terms understood in the art including, for example, $IC_{50}$, $EC_{50}$, $K_i$, or other standard terms known in the art. Thus, the evaluation provided herein can include evaluating the results where evaluating the results includes determining the inhibitory properties of the compound(s) being tested. In some instances evaluating the results also includes comparing the inhibitory properties of a compound being tested to the inhibitory properties of one or more reference compounds. Such a reference compound can be, for example, CASIN or other compounds described herein.

Small Molecules

Small molecule inhibitors can be used to specifically inhibit and/or modulate Cdc42 as disclosed herein. Any type of small molecule inhibitor which is known to one of skill in the art may be used. Many methods are known to identify small molecule inhibitors and commercial laboratories are available to screen for small molecule inhibitors. For example, chemicals can be obtained from the compound collection at Merck® Research Laboratories (Rahway, N.J.) or a like company. The compounds can be screened for inhibition of a Cdc42 by automated robotic screening in a 96-well plate format. For example, the compounds can be dissolved at an initial concentration of about 50 QM in DMSO and dispensed into the 96-well plate. The 96-well plate assay may contain an appropriate number of units of Cdc42 and target (a substrate). Compounds that cause greater than a 50% inhibition of Cdc42 activity can be further diluted and tested to establish the concentration necessary for a 50% inhibition of activity. In some embodiments, the screen will include Cdc42 protein and one or more of its binding proteins and candidate inhibitors. The inhibitory effect of screened compound to disrupt Cdc42 target binding can be monitored using, for example, an ELISA-type test with Cdc42 or the target immobilized on the surface and residual binding can be detected, for example, using antibodies of Cdc42 target (binding)-molecule conjugated to a reporter (e.g., alkaline phosphate). Binding assays can also be performed using surface plasmon resonance (SPR) based interaction screening including Cdc42 and it's binding target and inhibitor or any other assay screening protein interactions (eg. yeast two hybrid systems, immunoprecipitation, immunocapture experiments coupled to enymatic or FACS detection etc.). In some embodiments, the candidate Cdc42 inhibitor can be tested for its ability to inhibit Cdc42 GTPase activity using assays known in the art. In other embodiments, the Cdc42 inhibitor can be tested for its ability to reduce the quantity of GTP-bound Cdc42, for example, relative to the quantity GDP-bound Cdc42, using assays known in the art.

In any of the embodiments described herein, said Cdc42-specific inhibitor, said inhibitor of Cdc42, said inhibitor of GTPase Cdc42, said GTPase Cdc42 inhibitor, said agent capable of inhibiting GTPase Cdc42, or said agent that specifically inhibits Cdc42 comprises a compound of formula (I):

(I)

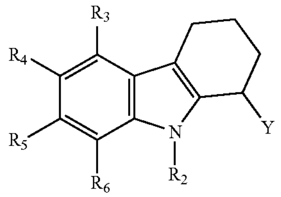

as a single enantiomer, a mixture of enantiomers, pharmaceutically acceptable salt, a solvate, or polymorph thereof, wherein:

Y is selected from the group consisting of $—OR_7$, $—NR_8R_9$, and $—NNR_8R_9$;

$R_7$ is selected from the group consisting of $C_{1-6}$ alkyl, $—(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $—(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro are each optionally substituted with one or more substituents each independently selected from the group consisting of halo, —CN, —OH, $C_{1-6}$ alkoxyl, heteroaryl, $R_{19}$, and —$OR_{20}$;

$R_8$ and $R_9$ are each separately a hydrogen or $R_{20}$; or $R_8$ and $R_9$ are optionally taken together with the nitrogen to which they are attached to form indolinyl, pyrrolidinyl, piperidinyl, piperazinyl, or morpholinyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro; or $R_8$ and $R_2$ come together to be $C_{1-3}$ alkyl linking together as a ring;

each $R_{20}$ is separately selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of $R_{21}$ and $R_{22}$, each $R_{21}$ is separately selected from the group consisting of halo, cyano, nitro, and hydroxy, each $R_{22}$ is separately selected from the group consisting of $C_{1-6}$ alkyl, $C_{1-6}$ alkoxy, —$(CH_2)_uC_{3-7}$cycloalkyl, $C_{2-6}$ alkenyl, hydroxy-$C_{1-6}$ alkyl, $R_{19}$, and $OR_{20}$, each optionally substituted with one or more substituents each independently selected from the group consisting of halo, cyano, nitro, hydroxy, $C_{1-6}$ alkyl, and $C_{1-6}$ alkoxy;

each u is independently 0, 1, 2, 3, or 4;

$R_2$ is a hydrogen, or selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, $C_{1-6}$ alkoxy substituted with up to 5 fluoro, and —$O(CH_2)_u$phenyl optionally substituted with one or more substituents each independently selected from the group consisting of halo, cyano, nitro, hydroxy, $C_{1-6}$ alkyl, and $C_{1-6}$ alkoxy; or $R_8$ and $R_2$ come together to be $C_{1-3}$ alkyl linking together as a ring;

$R_3$, $R_4$, $R_8$ and $R_6$ are each independently selected from the group consisting of hydrogen, halo, cyano, nitro, hydroxy, $C_{1-6}$ alkyl, —$(CH_2)_uC_{3-7}$cycloalkyl, —$O(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, —$(CH_2)_uC_{3-7}$cycloalkyl, —$O(CH_2)_uC_{3-7}$cycloalkyl, $C_{2-6}$ alkenyl, $C_{1-6}$ alkoxy, hydroxy-$C_{1-6}$ alkyl, and phenyl, each optionally substituted with one or more $R_{23}$, each $R_{23}$ is independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

each $R_{19}$ is independently aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

each $R_{20}$ is independently hydrogen or aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro; and wherein when Y is $NR_8R_9$ then $R_8$ and $R_2$ optionally come together to be $C_{1-3}$ alkyl linking together as a ring, with the proviso when $R_8$ comes together with $R_2$ to be $C_{1-3}$ alkyl linking together as a ring then $R_4$ is not substituted with hydroxyl.

In some embodiments, one, two or three of $R_3$, $R_4$, $R_8$ and $R_6$ are not hydrogen.

In some embodiments, $R_4$ is selected from the group consisting of $C_{1-6}$ alkyl, —$(CH_2)_uC_{3-7}$cycloalkyl, —$O(CH_2)_uC_{3-7}$cycloalkyl, $C_{2-6}$ alkenyl, $C_{1-6}$ alkoxy, phenyl, $C_{1-6}$ alkyl substituted with up to 5 fluoro, and $C_{1-6}$ alkoxy substituted with up to 5 fluoro, said $C_{1-6}$ alkyl, —$(CH_2)_uC_{3-7}$cycloalkyl, —$O(CH_2)_uC_{3-7}$ cycloalkyl, $C_{2-6}$ alkenyl, $C_{1-6}$ alkoxy, and phenyl, each optionally substituted with one or more substituents each independently selected from the group consisting of halo$C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro.

In some embodiments: Y is —$NR_8R_9$; $R_8$ is hydrogen; and $R_9$ is $C_{1-6}$ alkyl optionally substituted with one or more substituents each independently selected from the group consisting of hydroxy, $R_{19}$ and —$OR_{20}$; each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

In some embodiments: each $R_{19}$ is independently phenyl optionally substituted with one or more substituents each independently selected from the group consisting of halo, $C_{1-6}$ alkyl, and $C_{1-6}$ alkoxy; and each $R_{20}$ is independently phenyl optionally substituted with one or more substituents each independently selected from the group consisting of halo, $C_{1-6}$ alkyl, and $C_{1-6}$ alkoxy.

In some embodiments, $R_2$ and $R_8$ are hydrogen.

In some embodiments, Y is —$NR_8R_9$ and $R_8$ and $R_2$ come together to be $C_{1-3}$ alkyl linking together as a ring.

In some embodiments, $R_9$ is hydrogen.

In some embodiments, $R_9$ is $C_{1-6}$ alkyl optionally substituted with one or more substituents each independently selected from the group consisting of hydroxy, $R_{19}$ or —$OR_{20}$;

each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

In some embodiments, $R_9$ is hydrogen or $C_{1-6}$ alkyl, optionally substituted with one or more substituents each independently selected from the group consisting of hydroxyl, $R_{19}$ and $—OR_{20}$;

each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

In some embodiments, $R_4$ is selected from the group consisting of $C_{1-6}$ alkyl, $—(CH_2)_uC_{3-7}$cycloalkyl, $—O(CH_2)_uC_{3-7}$cycloalkyl, $C_{2-6}$ alkenyl, $C_{1-6}$ alkoxy, phenyl, $C_{1-6}$ alkyl substituted with up to 5 fluoro, and $C_{1-6}$ alkoxy substituted with up to 5 fluoro, said $C_{1-6}$ alkyl, $—(CH_2)_uC_{3-7}$cycloalkyl, $—O(CH_2)_uC_{3-7}$cycloalkyl, $C_{2-6}$ alkenyl, $C_{1-6}$ alkoxy, and phenyl, each optionally substituted with one or more $R_{23}$, each $R_{23}$ is independently selected from the group consisting of halo, $C_{1-6}$ alkyl, $—(CH_2)_u C_{3-7}$cycloalkyl, $C_{2-6}$ alkenyl, $C_{1-6}$ alkoxy, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, $C_{1-6}$ alkyl, $—(CH_2)_uC_{3-7}$cycloalkyl, $C_{2-6}$ alkenyl, $C_{1-6}$ alkoxy, $C_{1-6}$ alkyl substituted with up to 5 fluoro, and $C_{1-6}$ alkoxy substituted with up to 5 fluoro.

In some embodiments, $R_4$ is selected from the group consisting of $C_{1-6}$ alkyl, $C_{3-7}$cycloalkyl, $—OC_{3-7}$cycloalkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, $C_{1-6}$ alkyl, $C_{1-6}$ alkoxy, $C_{1-6}$ alkyl substituted with up to 5 fluoro, and $C_{1-6}$ alkoxy substituted with up to 5 fluoro.

In some embodiments, Y may be $—NR_8R_9$ and $R_8$ and $R_2$ come together to be $C_{1-3}$ alkyl linking together as a ring.

In some embodiments, $R_2$ is a hydrogen or selected from the group consisting of $C_{1-6}$ alkyl, $C_{3-7}$ cycloalkyl, and phenyl, said $C_{1-6}$ alkyl optionally substituted with one or more halo.

In some embodiments, $R_2$ is a hydrogen.

In some embodiments, $R_9$ is hydrogen, or $C_{1-6}$ alkyl, optionally substituted with one or more substituents each independently selected from the group consisting of hydroxyl, $R_{19}$ and $—OR_{20}$;

each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

In some embodiments, the compound of formula (I) is selected from the group consisting of:

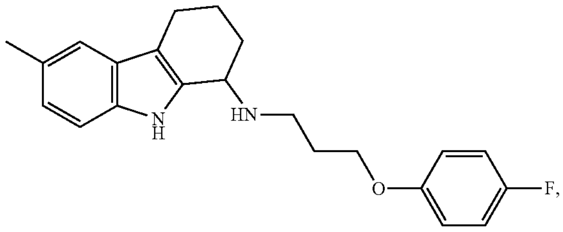
,

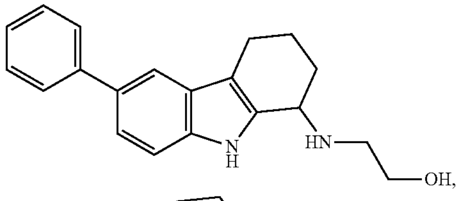
,

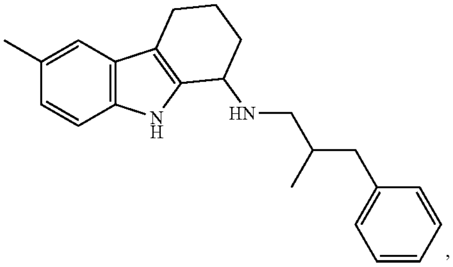
,

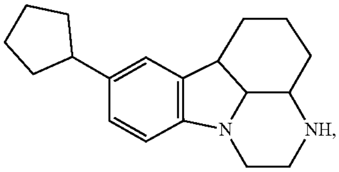
and

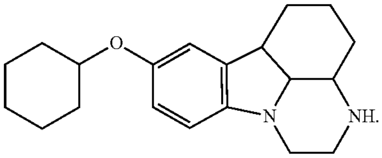
.

In some embodiments, the compound of formula (I) is CASIN:

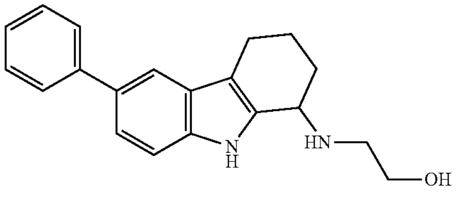 [SMILES: OCCNC1CCCc2c1[nH]c1ccc(-c3ccccc3)cc21]

or a pharmaceutically acceptable salt thereof.

The term "ester" refers to a chemical moiety with formula $—(R)_n—COOR'$, where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula $—(R)_n—C(O)NHR'$ or $—(R)_n—NHC(O)R'$, where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, 3rd Ed., John Wiley & Sons, New York, N.Y., 1999, which is incorporated herein in its entirety.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, Protective Groups in Organic Synthesis, 3. Ed. John Wiley & Sons, 1999, and in J. F. W. McOmie, Protective Groups in Organic Chemistry Plenum Press, 1973, both of which are hereby incorporated by reference. The protecting group moiety may be chosen in such a way, that they are stable to the reaction conditions applied and readily removed at a convenient stage using methodology known from the art. A non-limiting list of protecting groups include benzyl; substituted benzyl; alkylcarbonyls (e.g., t-butoxycarbonyl (BOC)); arylalkylcarbonyls (e.g., benzyloxycarbonyl, benzoyl); substituted methyl ether (e.g. methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g. benzoate ester); carbonates (e.g. methoxymethylcarbonate); sulfonates (e.g. tosylate, mesylate); acyclic ketal (e.g. dimethyl acetal); cyclic ketals (e.g., 1,3-dioxane or 1,3-dioxolanes); acyclic acetal; cyclic acetal; acyclic hemiacetal; cyclic hemiacetal; and cyclic dithioketals (e.g., 1,3-dithiane or 1,3-dithiolane).

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds of the invention may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

The substituent "R" appearing by itself and without a number designation refers to a substituent selected from the group consisting of hydrogen, alkyl, cycloalkyl, aryl, heteroaryl (bonded through a ring carbon) and heteroalicyclic (bonded through a ring carbon).

An "O-carboxy" group refers to a $RC(=O)O—$ group, where R is as defined herein.

A "C-carboxy" group refers to a $—C(=O)OR$ groups where R is as defined herein.

An "acetyl" group refers to a $—C(=O)CH_3$, group.

A "trihalomethanesulfonyl" group refers to a $X_3CS(=O)_2—$ group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a $—S(=O)—R$ group, with R as defined herein.

A "S-sulfonamido" group refers to a —S(═O)$_2$NR, group, with R as defined herein.

A "N-sulfonamido" group refers to a RS(═O)$_2$NH— group with R as defined herein.

A "trihalomethanesulfonarnido" group refers to a $X_3$CS(═O)$_2$NR— group with X and R as defined herein.

An "O-carbamyl" group refers to a —OC(═O)—N(R)$_2$, group with R as defined herein.

An "N-carbamyl" group refers to a ROC(═O)NH— group, with R as defined herein.

An "O-thiocarbamyl" group refers to a —OC(═S)—N(R)$_2$, group with R as defined herein.

An "N-thiocarbamyl" group refers to an ROC(═S)NH— group, with R as defined herein.

A "C-amido" group refers to a —C(═O)—N(R)$_2$ group with R as defined herein.

An "N-amido" group refers to a RC(═O)NH— group, with R as defined herein.

The term "perhaloalkyl" refers to an alkyl group where all of the hydrogen atoms are replaced by halogen atoms.

The term "acylalkyl" refers to a RC(═O)R'— group, with R as defined herein, and R' being a diradical alkylene group. Examples of acylalkyl, without limitation, may include $CH_3C$(═O)$CH_2$—, $CH_3C$(═O)$CH_2CH_2$—, $CH_3CH_2C$(═O)$CH_2CH_2$—, $CH_3C$(═O)$CH_2CH_2CH_2$—, and the like.

Unless otherwise indicated, when a substituent is deemed to be "optionally substituted," it is meant that the substituent is a group that may be substituted with one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

In the present context, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

As used herein, "heterocyclyl" means a cyclic ring system comprising at least one heteroatom in the ring system backbone. The heteroatoms are independently selected from oxygen, sulfur, and nitrogen. Heterocyclyls may include multiple fused rings. Heterocyclyls may have any degree of saturation provided that at least one ring in the ring system is not aromatic. Heterocyclyls may be substituted or unsubstituted, and are attached to other groups via any available valence, preferably any available carbon or nitrogen. Preferred monocyclic heterocycles are of 5 or 6 members. In six membered monocyclic heterocycles, the heteroatom(s) are selected from one up to three of oxygen, sulfur, and nitrogen, and wherein when the heterocycle is five membered, preferably it has one or two heteroatoms selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. The attachment point of a heterocycle radical can be at the position of a nitrogen heteroatom or via a carbon atom of the heterocycle.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

As used herein, the term "heteroaryl" means an aromatic radical having one or more heteroatom(s) (e.g., oxygen, sulfur, or nitrogen) in the ring backbone and may include a single ring (e.g., pyridine) or multiple condensed rings (e.g., quinoline). Heteroaryl groups can carry one or more substituents, each independently selected from halo, hydroxy, amino, cyano, nitro, cycloalkyl, haloalkyl, aryl, heterocyclyl, mercapto, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, and trifluoromethyl. Representative examples of heteroaryl groups include, but are not limited to, optionally substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents can be halo, hydroxy, cyano, O—$C_{1-6}$-alkyl, $C_{1-6}$-alkyl, hydroxy-$C_{1-6}$-alkyl, and amino-$C_{1-6}$-alkyl.

Antisense Molecules

In some embodiments, the Cdc42-specific inhibitor can be an antisense molecule. The term "antisense" (AS) or "antisense fragment" refers to a polynucleotide fragment (comprising either deoxyribonucleotides, ribonucleotides or a mixture of both) having inhibitory antisense activity, which causes a decrease in the expression of the endogenous genomic copy of the corresponding gene. An AS polynucleotide refers to a polynucleotide which comprises consecutive nucleotides having a sequence of sufficient length and homology to a sequence present within the sequence of the target gene to permit hybridization of the AS to the gene. Many reviews have covered the main aspects of antisense (AS) technology and its enormous therapeutic potential (see, for example, Aboul-Fadl T., Curr Med. Chem. 2005; 12(19): 2193-214; Crooke S T, Curr Mol. Med. 2004 August; 4(5):465-87; Crooke S T, Annu Rev Med. 2004; 55:61-95; Vacek M et al., Cell Mol Life Sci. 2003 May; 60(5):825-33; Cho-Chung Y S, Arch Pharm Res. 2003 March; 26(3):183-91; Moreira J N et al., Rev Recent Clin Trials 2006 September; 1(3):217-35). There are further reviews on the chemical (Crooke, 1995; Uhlmann et al, 1990), cellular (Wagner, 1994) and therapeutic (Hanania, et al, 1995; Scanlon, et al, 1995; Gewirtz, 1993) aspects of this technology. Antisense intervention in the expression of specific genes can be achieved by the use of synthetic AS oligonucleotide sequences (see, e.g., Lefebvre-d'Hellencourt et al, 1995; Agrawal, 1996; LevLehman et al, 1997).

AS oligonucleotide sequences may be short sequences of DNA, typically a 15-mer to a 30-mer but may be as small as a 7-mer (Wagner et al, 1996), designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996 Semin Oncol. 23(1):78-87). In that case, RNase H will cleave the RNA component of the duplex and can potentially release the AS to further hybridize with additional molecules of the target RNA. An additional mode of action results from the interaction of AS with genomic DNA to form a triple helix, which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al., 1996). For example, the computer program OLIGO® (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analogue substitutions do not substantially affect function.

Phosphorothioate antisense oligonucleotides do not normally show significant toxicity at concentrations that are effective and exhibit sufficient pharmacodynamic half-lives in animals (Agarwal et al., 1996) and are nuclease resistant. Antisense induced loss-of-function phenotypes related with cellular development were shown for the glial fibrillary acidic protein (GFAP), for the establishment of tectal plate formation in chick (Galileo et al., 1991) and for the N-myc protein, responsible for the maintenance of cellular heterogeneity in neuroectodermal cultures (ephithelial vs. neuroblastic cells, which differ in their colony forming abilities, tumorigenicity and adherence) (Rosolen et al., 1990; Whitesell et al, 1991). Antisense oligonucleotide inhibition of basic fibroblast growth factor (bFgF), having mitogenic and angiogenic properties, suppressed 80% of growth in glioma cells (Morrison, 1991) in a saturable and specific manner. Being hydrophobic, antisense oligonucleotides interact well with phospholipid membranes (Akhter et al., 1991). Following their interaction with the cellular plasma membrane, they are actively (or passively) transported into living cells (Loke et al., 1989), in a saturable mechanism predicted to involve specific receptors (Yakubov et al., 1989).

siRNA

In other embodiments, the Cdc42-specific inhibitor can be a "small interfering RNA" (siRNA). siRNA refers to an RNA molecule which decreases or silences (prevents) the expression of a gene/mRNA (e.g., Cdc42) of its endogenous cellular counterpart. The term is understood to encompass "RNA interference" (RNAi). RNA interference (RNAi) refers to the process of sequence-specific post transcriptional gene silencing in mammals mediated by small interfering RNAs (siRNAs, e.g., short hairpin RNAs (shRNAs)) (Fire et al, 1998, Nature 391, 806). The corresponding process in plants is commonly referred to as specific post transcriptional gene silencing or RNA silencing and is also referred to as quelling in fungi. The RNA interference response may feature an endonuclease complex containing an siRNA, commonly referred to as an RNA-induced silencing complex (RISC), which mediates cleavage of single-stranded RNA having sequence complementary to the antisense strand of the siRNA duplex. Cleavage of the target RNA may take place in the middle of the region complementary to the antisense strand of the siRNA duplex (Elbashir et al 2001, Genes Dev., 15, 188). For recent information on these terms and proposed mechanisms, see Bernstein E., Denli A M., Hannon G J: The rest is silence. RNA. 2001 November; 7(11):1509-21; and Nishikura K.: A short primer on RNAi: RNA-directed RNA polymerase acts as a key catalyst. Cell. 2001 Nov. 16; 107(4):415-8.

RNAi is an efficient method for the inactivation of genes (Nature Reviews, 2002, v. 3, p. 737-47; Nature, 2002, v. 418, p. 244-51). As a method, it is based on the ability of dsRNA species to enter a specific protein complex, where it is then targeted to the complementary cellular RNA and specifically degrades it. In more detail, dsRNAs are digested into short (17-29 bp) inhibitory RNAs (siRNAs) by type III RNAses (DICER, Drosha, etc) (Nature, 2001, v. 409, p. 363-6; Nature, 2003, 425, p. 415-9). These fragments and complementary mRNA are recognized by the specific RISC protein complex. The whole process is culminated by endonuclease cleavage of target mRNA (Nature Reviews, 2002, v. 3, p. 737-47; Curr Opin Mol. Ther. 2003 June; 5(3):217-24).

For disclosure on how to design and prepare siRNA to known genes see, for example, Chalk A M, Wahlestedt C, Sonnhammer E L. 2004 Jun. 18; 319(1):264-74; Sioud M, Leirdal M., Methods Mol. Biol. 2004; 252:457-69; Levenkova N, Gu Q, Rux J J. 2004 Feb. 12; 20(3):430-2; and Ui-Tei K, Naito Y, Takahashi F, Haraguchi T, Ohki-Hamazaki H, Juni A, Ueda R, Saigo K., Nucleic Acids Res. 2004 Feb. 9; 32(3):936-48. See also PCT publications WO 2004/015107 (Atugen) and WO 02/44321 (Tuschl et al), and also Chiu Y L, Rana T M. RNA 2003 September; 9(9):1034-48 and U.S. Pat. Nos. 5,898,031 and 6,107,094 (Crooke) for production of modified/more stable siRNAs.

DNA-based vectors capable of generating siRNA within cells have been developed. The method generally involves transcription of short hairpin RNAs that are efficiently processed to form siRNAs within cells. (see, e.g., Paddison et al. PNAS 2002, 99:1443-1448; Paddison et al. Genes & Dev 2002, 16:948-958; Sui et al. PNAS 2002, 8:5515-5520; and Brummelkamp et al. Science 2002, 296:550-553). These reports describe methods to generate siRNAs capable of specifically targeting numerous endogenously and exogenously expressed genes.

For methods related to the delivery of siRNAs, see, for example, Shen et al (FEBS letters 539: 111-114 (2003)), Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details, see, for example, Tolentino et al., Retina 24(1) February 2004 pp 132-138.

In some embodiments the oligoribonucleotide according to embodiments disclosed herein comprises modified siRNA. In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid, and the second strand comprises ribonucleotide sequence at least partially complementary to the first strand and wherein said first strand and/or said second strand comprises a plurality of groups of modified ribonucleotides having a modification at the 2'-position of the sugar moiety whereby within each strand each group of modified ribonucleotides is flanked on one or both sides by a group of flanking ribonucleotides whereby each ribonucleotide forming the group of flanking ribonucleotides is selected from an unmodified ribonucleotide or a ribonucleotide having a modification different from the modification of the groups of modified ribonucleotides.

Ribozymes

In some embodiments, the Cdc42-specific inhibitor can be a ribozyme. The term "ribozyme" refers to an RNA molecule that possesses RNA catalytic ability and cleaves a specific site in a target RNA. In accordance with the embodiments disclosed herein, ribozymes which cleave mRNA (e.g., Cdc42 mRNA) may be utilized as inhibitors. This may be necessary in cases where antisense therapy is limited by stoichiometric considerations (Sarver et al., 1990, Gene Regulation and Aids, pp. 305-325). Ribozymes can then be used that will target the a gene associated with a bone marrow disease. The number of RNA molecules that are cleaved by a ribozyme is greater than the number predicted by stochiochemistry. (Hampel and Tritz, 1989; Uhlenbeck, 1987).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). In general the ribozyme has a length of from about 30-100 nucleotides. Delivery of ribozymes is similar to that of AS fragments and/or siRNA molecules.

The term "nucleic acids," as used herein, may be DNA or RNA or modified versions thereof. Nucleic acids may also include modified nucleotides that permit correct read through by a polymerase and do not alter expression of a polypeptide encoded by that nucleic acid. The terms "nucleic acid" and "oligonucleotide" are used interchangeably to refer to a molecule comprising multiple nucleotides. As used herein, the terms refer to oligoribonucleotides as well as oligodeoxyribonucleotides. The terms shall also include polynucleosides (e.g., a polynucleotide minus the phosphate) and any other organic base containing polymer. Nucleic acids include vectors, e.g., plasmids, as well as oligonucleotides. Nucleic acid molecules can be obtained from existing nucleic acid sources, but are preferably synthetic (e.g., produced by oligonucleotide synthesis).

Polynucleotides to be used according to embodiments disclosed herein may undergo modifications so as to possess improved therapeutic properties. Modifications or analogs of nucleotides can be introduced to improve the therapeutic properties of polynucleotides. Improved properties include increased nuclease resistance and/or increased ability to permeate cell membranes. Nuclease resistance, where needed, is provided by any method known in the art that does not interfere with biological activity of the AS polynucleotide, siRNA, cDNA and/or ribozymes as needed for the method of use and delivery (Iyer et al., 1990; Eckstein, 1985; Spitzer and Eckstein, 1988; Woolf et al., 1990; Shaw et al., 1991). Modifications that can be made to oligonucleotides in order to enhance nuclease resistance include modifying the phosphorous or oxygen heteroatom in the phosphate backbone. These include preparing methyl phosphonates, phosphorothioates, phosphorodithioates and morpholino oligomers. In one embodiment it is provided by having phosphorothioate bonds linking between the four to six 3'-terminus nucleotide bases. Alternatively, phosphorothioate bonds link all the nucleotide bases. Other modifications known in the art may be used where the biological activity is retained, but the stability to nucleases is substantially increased.

All analogues of, or modifications to, a polynucleotide may be employed with the embodiments disclosed herein, provided that said analogue or modification does not substantially affect the function of the polynucleotide. The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of polynucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones, as well as LNA ("locked nucleic acid").

Embodiments disclosed herein also include nucleic acids (e.g., siRNA) that can have the following degrees of homology or identity to a Cdc42-specific inhibitory nucleic acid: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a range bounded by any two of the aforementioned percentages. Candidate Cdc42-specific inhibitory nucleic acids having greater than or equal to 35% homology or identity can be identified by methods known in the art and can be subsequently examined using functional assays, for example, the assays described herein and those known in the art.

The term "homology" refers to the percent of identity between two polynucleotide or two polypeptide moieties. The correspondence between the sequence from one moiety to another can be determined by techniques known in the art. For example, homology can be determined by a direct comparison of the sequence information between two polynucleotide or polypeptide molecules by aligning the sequence information and using readily available computer programs. Alternatively, homology can be determined by hybridization of polynucleotides under conditions, which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

Preparation of Peptides and Polypeptides

In some embodiments, the Cdc42-specific inhibitor can be a polypeptide (e.g., a dominant negative peptide, an antibody, or an affibody). Polypeptides may be produced, for example, via several methods known in the art (e.g., synthetically or via recombinant methods).

The terms "polypeptide," "peptide," and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide," and "protein" include glycoproteins, as well as non-glycoproteins. Polypeptide products can be biochemically synthesized such as by employing standard solid phase techniques. Such methods include but are not limited to exclusive solid phase synthesis, partial solid phase synthesis methods, fragment condensation, classical solution synthesis. These methods are preferably used when the peptide is relatively short (e.g., 10 kDa) and/or when it cannot be produced by recombinant techniques (e.g., not encoded by a nucleic acid sequence) and therefore involves different chemistry. Solid phase polypeptide synthesis procedures are well known in the art and further described by John Morrow Stewart and Janis Dillaha Young, Solid Phase Peptide Syntheses (2nd Ed., Pierce Chemical Company, 1984). Synthetic polypeptides can optionally be purified by preparative high performance liquid chromatography [Creighton T. (1983) Proteins, structures and molecular principles. WH Freeman and Co. N.Y.], after which their composition can be confirmed via amino acid sequencing. In cases where large amounts of a polypeptide are desired, it can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In some embodiments, the method of making the polypeptides or fragments thereof is to clone a polynucleotide comprising the cDNA of the gene into an expression vector and culture the cell harboring the vector so as to express the encoded polypeptide, and then purify the resulting polypeptide, all performed using methods known in the art as described in, for example, Marshak et al., "Strategies for Protein Purification and Characterization. A laboratory course manual." CSHL Press (1996). (in addition, see, e.g., Bibl Haematol. 1965; 23:1165-74 Appl Microbiol. 1967 July; 15(4):851-6; Can J. Biochem. 1968 May; 46(5):441-4; Biochemistry. 1968 July; 7(7):2574-80; Arch Biochem Biophys. 1968 Sep. 10; 126(3):746-72; Biochem Biophys Res Commun. 1970 Feb. 20; 38(4):825-30).).

The expression vector can include a promoter for controlling transcription of the heterologous material and can be either a constitutive or inducible promoter to allow selective transcription. Enhancers that can be required to obtain necessary transcription levels can optionally be included. The expression vehicle can also include a selection gene.

Vectors can be introduced into cells or tissues by any one of a variety of methods known within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al. (1986).

Preparation of Anti-Cdc42 Antibodies

Antibodies that bind to Cdc42 or a fragment derived therefrom may be prepared using an intact polypeptide or fragments containing smaller polypeptides as the immunizing antigen. For example, it may be desirable to produce antibodies that specifically bind to the N- or C-terminal or any other suitable domains of Cdc42. The polypeptide used to immunize an animal can be derived from translated cDNA or chemical synthesis and can be conjugated to a carrier protein, if desired. Such commonly used carriers which are chemically coupled to the polypeptide include keyhole limpet hemocyanin (KLH), thyroglobulin, bovine serum albumin (BSA) and tetanus toxoid. The coupled polypeptide is then used to immunize the animal.

If desired, polyclonal or monoclonal antibodies can be further purified, for example by binding to and elution from a matrix to which the polypeptide or a peptide to which the antibodies were raised is bound. Those skilled in the art know various techniques common in immunology for purification and/or concentration of polyclonal as well as monoclonal antibodies (Coligan et al, Unit 9, Current Protocols in Immunology, Wiley Interscience, 1994).

Methods for making antibodies of all types, including fragments, are known in the art (See for example, Harlow and Lane, Antibodies: A Laboratory Manual, Cold Spring Harbor Laboratory, New York (1988)). Methods of immunization, including all necessary steps of preparing the immunogen in a suitable adjuvant, determining antibody binding, isolation of antibodies, methods for obtaining monoclonal antibodies, and humanization of monoclonal antibodies are all known to the skilled artisan The antibodies may be humanized antibodies or human antibodies. Antibodies can be humanized using a variety of techniques known in the art including CDR-grafting (EP239,400: PCT publication WO0.91/09967; U.S. Pat. Nos. 5,225,539; 5,530,101; and 5,585,089, veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,332).

The monoclonal antibodies as defined include antibodies derived from one species (such as murine, rabbit, goat, rat, human, etc.) as well as antibodies derived from two (or more) species, such as chimeric and humanized antibodies.

Completely human antibodies are particularly desirable for therapeutic treatment of human patients. Human antibodies can be made by a variety of methods known in the art including phage display methods using antibody libraries derived from human immunoglobulin sequences. See also U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, each of which is incorporated herein by reference in its entirety.

Additional information regarding all types of antibodies, including humanized antibodies, human antibodies and antibody fragments can be found in WO 01/05998, which is incorporated herein by reference in its entirety.

Neutralizing antibodies can be prepared by the methods discussed above, possibly with an additional step of screening for neutralizing activity by, for example, a survival assay.

Embodiments disclosed herein also relate to the preparation and use of affibodies, binding proteins of non-Ig origin developed by combinatorial protein engineering principles, as described, for example, in Nygren P A 2008 FEBS Journal 275:2668-2676.

The polypeptides employed in embodiments disclosed herein may also be modified, optionally chemically modified, in order to improve their therapeutic activity. "Chemically modified"—when referring to the polypeptides, refers to a polypeptide where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristylation, pegylation, prenylation, phosphorylation, ubiqutination, or any similar process.

Additional possible polypeptide modifications (such as those resulting from nucleic acid sequence alteration) include substitutions, deletions, and insertions.

A "conservative substitution" refers to the substitution of an amino acid in one class by an amino acid of the same class, where a class is defined by common physicochemical amino acid side chain properties and high substitution frequencies in homologous polypeptides found in nature, as determined, for example, by a standard Dayhoff frequency exchange matrix or BLOSUM matrix.

A "non-conservative substitution" refers to the substitution of an amino acid in one class with an amino acid from another class; for example, substitution of an Ala, a class II residue, with a class III residue such as Asp, Asn, Glu, or Gln.

A "deletion" refers to a change in either nucleotide or amino acid sequence in which one or more nucleotides or amino acid residues, respectively, are absent.

An "insertion" or "addition" refers to a change in a nucleotide or amino acid sequence which has resulted in the addition of one or more nucleotides or amino acid residues, respectively, as compared to the naturally occurring sequence.

A "substitution" refers to the replacement of one or more nucleotides or amino acids by different nucleotides or amino acids, respectively. As regards amino acid sequences the substitution may be conservative or non-conservative.

Embodiments disclosed herein also include polypeptides (e.g., dominant negative polypeptides or antibodies) that can have the following degrees of homology or identity to a Cdc42-specific inhibitory polypeptide: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a range bounded by any two of the aforementioned percentages. Candidate Cdc42-specific inhibitory polypeptides having greater than or equal to 35% homology or identity can be identified by methods known in the art and can be subsequently examined using functional assays, for example, the assays described herein and those known in the art.

Pharmaceutical Compositions and Administration

Also provided herein are pharmaceutical compositions for the methods provided herein. In some embodiments, the pharmaceutical compositions comprise a Cdc42-specific inhibitor and a pharmaceutically acceptable carrier.

Compounds, or mixtures of compounds described herein, can be synthetic, naturally-occurring, or a combination thereof. Compounds, or mixtures of compounds described herein can comprise amino acids, nucleotides, hydrocarbons, lipids, polysaccharides, etc. Compounds, or mixtures of compounds described herein preferably comprise a Cdc42-specific inhibitor (e.g., CASIN). Compounds, or mixtures of compounds described herein, can be formulated into pharmaceutical composition comprising a pharmaceutically acceptable carrier and other excipients as apparent to the skilled worker. Such composition can additionally contain effective amounts of other compounds, especially for the treatment of conditions, diseases, and/or disorders described herein.

Some embodiments comprise the administration of a pharmaceutically effective quantity of active agent or its pharmaceutically acceptable salts or esters, active agent analogs or their pharmaceutically acceptable salts or esters, or a combination thereof.

The compositions and preparations described preferably contain at least 0.1% of active agent. The percentage of the compositions and preparations can, of course, be varied, and can contain between about 2% and 60% of the weight of the amount administered. Preferably, the percentage of the compositions and preparations can contain between about 2, 5, 10, or 15% and 30, 35, 40, 45, 50, 55, or 60% of the weight of the amount administered. The amount of active compounds in such pharmaceutically useful compositions and preparations is such that a suitable dosage will be obtained.

The active agent can form salts, which are also within the scope of the preferred embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (e.g., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

The active agents which contain a basic moiety, such as, but not limited to an amine or a pyridine or imidazole ring, can form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The active agents which contain an acidic moiety, such as, but not limited to a carboxylic acid, can form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups can be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the preferred embodiments are also contemplated herein. The term "prodrug", as employed herein, denotes a compound which, upon administration to a subject, undergoes chemical conversion by metabolic or chemical processes to yield a compound of the active agent, and/or a salt and/or solvate thereof. Solvates of the active agent are preferably hydrates.

Active agent, and salts thereof, can exist in their tautomeric form (for example, as an amide or imino ether). All such tautomeric forms are contemplated herein as part of the preferred embodiments.

All stereoisomers of the present compounds, such as those, for example, which can exist due to asymmetric carbons on any of the substituents, including enantiomeric forms (which can exist even in the absence of asymmetric carbons) and diastereomeric forms, are contemplated and within the scope of the preferred embodiments. Individual stereoisomers of the compounds of the preferred embodiments can, for example, be substantially free of other isomers, or can be admixed, for example, as racemates or with all other or other selected, stereoisomers. The chiral centers of the preferred embodiments can have the S or R configuration as defined by the IUPAC 1974 Recommendations.

When the compounds according to the preferred embodiments are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts can be prepared by reacting the active agent with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents can be used. Organic bases like lysine, arginine, diethanolamine, choline, guandine and their derivatives etc. can also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents can also be used.

The compounds can be formulated in various forms, including solid and liquid forms, such as tablets, gel, syrup, powder, aerosol, creams, lotions, tinctures, foams, etc.

The compositions of the preferred embodiments can contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds are administered will vary according to the dosage form, mode of administration, the condition being treated and particulars of the patient being treated. Accordingly, optimal therapeutic concentrations will be best determined at the time and place through routine experimentation.

The compounds according to the preferred embodiments can also be used enterally. Orally, the compounds according to the preferred embodiments are suitable administered at the rate of 100 μg to 100 mg per day per kg of body weight. Preferably, orally, the compounds according to the preferred embodiments are suitable administered at the rate of about 100, 150, 200, 250, 300, 350, 400, 450, or 500 μg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; a preferred method of administration consists in using a suitable form containing from 1 mg to about 500 mg of active substance. Preferably, a method of administration consists in using a suitable form containing from about 1, 2, 5, 10, 25, or 50 mg to about 100, 200, 300, 400, 500 mg of active substance.

The compounds according to the preferred embodiments can also be administered parenterally in the form of solutions or suspensions for intravenous or intramuscular perfusions or injections. In that case, the compounds according to the preferred embodiments are generally administered at the rate of about 10 μg to 10 mg per day per kg of body weight; a preferred method of administration consists of using solutions or suspensions containing approximately from 0.01 mg to 1 mg of active substance per ml. Preferably, the compounds according to the preferred embodiments are generally administered at the rate of about 10, 20, 30, 40, 50, 60, 70, 80, 90, or 100 μg to 1, 2, 3, 4, 5, 6, 7, 8, 9, or 10 mg per day per kg of body weight; a preferred method of administration consists of using solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml.

The active compounds and/or pharmaceutical compositions of the embodiments disclosed herein can be administered according to various routes, typically by injection or oral administration, including local or systemic administration(s). Furthermore, repeated administrations can be performed, if needed.

For ex vivo administration, the active agent can be administered by any standard method that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the active agent is encapsulated, or rectal administration, particularly when the active agent is in suppository form.

It is contemplated that such target cells can be located within a subject or human patient, in which case a safe and effective amount of the active agent, in pharmacologically acceptable form, would be administered to the patient. Generally speaking, it is contemplated that useful pharmaceutical compositions of the preferred embodiments will include the selected active compound derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the subject under such circumstances will depend upon the intended application and will be apparent to those of skill in the art in light of the examples which follow.

Any composition chosen should be of low or non-toxicity to the cell. Toxicity for any given compound can vary with the concentration of compound used. It is also beneficial if the compound chosen is metabolized or eliminated by the body and if this metabolism or elimination is done in a manner that will not be harmfully toxic.

The examples are illustrative of the types of compounds to be used in the method claimed herein; the list is not exhaustive. Derivatives of the above compounds that fit the criteria of the claims are preferably also be considered when choosing an active compound.

The compound is preferably administered such that a therapeutically effective concentration of the compound is in contact with the affected cells of the body. The dose administered to a subject, particularly a human, in the context of the preferred embodiments is preferably sufficient to effect a therapeutic response in the subject over a reasonable period of time. The dose will be determined by the strength of the particular compound employed and the condition of the subject, as well as the body weight of the subject to be treated. The existence, nature, and extent of any adverse side effects that might accompany the administration of a particular compound also will determine the size of the dose and the particular route of administration employed with a particular patient. In general, the compounds of the preferred embodiments are therapeutically effective at low doses. The generally useful dose range is from about 0.001 mM, or less, to about 100 mM, or more. Preferably, the effective dose range is from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds will be generally administered in low doses.

The compound can be administered in a pharmaceutically acceptable carrier. Pharmaceutically acceptable carriers are well-known to those who are skilled in the art. The choice of carrier will be determined in part by the particular compound, as well as by the particular method used to administer the composition. Accordingly, there is a wide variety of suitable formulations of the pharmaceutical composition of the preferred embodiments.

The compounds can be administered orally, topically, parenterally, by inhalation or spray, vaginally, rectally or sublingually in dosage unit formulations. The term “administration by injection” includes but is not limited to: intravenous, intraarticular, intramuscular, subcutaneous and parenteral injections, as well as use of infusion techniques. Dermal administration can include topical application or transdermal administration. One or more compounds can be present in association with one or more non-toxic pharmaceutically acceptable carriers and if desired other active ingredients.

Compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Compounds of the preferred embodiments can also be administrated transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

In some embodiments the composition can comprise, for example a topical formulation. In some embodiments, the topical formulation is a non-transdermal composition, formulated so as to not penetrate beyond the dermal layer. Non-transdermal formulations are known in the art, and include matrical or micellar solutions, bandages, wound dressings, aerosol sprays, foams, non-transdermal topical patches, tinctures, topical administrative agents and the like.

Pharmaceutical compositions of the preferred embodiments can also be in the form of oil-in-water emulsions. The oil phase can be a vegetable oil, for example olive oil or arachis oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

For all regimens of use disclosed herein for active agent, the daily oral dosage regimen will preferably be from about 0.01 to about 200 mg/Kg of total body weight. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. Preferably, the daily dosage for administration by injection, including intravenous, intramuscular, subcutaneous and parenteral injections, and use of infusion techniques will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily vaginal dosage regime will preferably be from 0.01 to 200 mg/Kg of total body weight. The daily topical dosage regimen will preferably be from 0.01 to 200 mg administered between one to four times daily. The concentration for vaginal dosage and topical dosage will preferably be that required to maintain a daily dose is of from 0.1 to 200 mg/Kg. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily inhalation dosage regimen will preferably be from 0.01 to 10 mg/Kg of total body weight. Preferably, the daily inhalation dosage regimen will preferably be from about 0.01, 0.05, 0.1, 0.5, to about 1, 2, 3, 4, 5, or 10, mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

The active compounds can be incorporated into pharmaceutical compositions suitable for administration to a subject, e.g., a human. Such compositions typically comprise the nucleic acid molecule, protein, modulator, or antibody and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the preferred embodiments. Supplementary active compounds can also be incorporated into the compositions. A pharmaceutical composition of the preferred embodiments is formulated to be compatible with its intended route of administration. Examples of routes of administration include parenteral, e.g., intravenous, intradermal, subcutaneous, oral (e.g., inhalation), transdermal, non-transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid, buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In some embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes) can also be used as pharmaceutically acceptable carriers. These can be prepared according to methods known to those skilled in the art.

It is especially advantageous to formulate oral or parenteral compositions in dosage unit form for ease of administration and uniformity of dosage. “Dosage unit form” as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

As used herein, the terms “effective amount” or “therapeutically effective amount” means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the preferred embodiments, a therapeutically effective amount of one, two, or more of the active agents of the preferred embodiments is administered to a subject. The active agents of the preferred embodiments can be administered in accordance with the method of the preferred embodiments either alone of in combination with other known therapies. When co-administered with one or more other therapies, the active agents of the preferred embodiments can be administered either simultaneously with the other treatment(s), or sequentially. If administered sequentially, the attending physician will decide on the appropriate sequence of administering the active agents of the preferred embodiments in combination with the other therapy.

Generally, a therapeutically effective amount of active agent (i.e., an effective dosage) ranges from about 0.001 to 5000 mg/kg body weight, more preferably about 0.01 to 1000 mg/kg body weight, more preferably about 0.01 to 500 mg/kg body weight, more preferably about 0.01 to 250 mg/kg body weight, more preferably about 0.01 to 100 mg/kg body weight, more preferably about 0.001 to 60 mg/kg body weight, more preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors can influence the dosage required to effectively treat a subject, including but not limited to the severity of the disease or disorder, previous treatments, the general health and/or age of the subject, and other diseases present. Moreover, treatment of a subject with a therapeutically effective amount can include a single treatment or, preferably, can include a series of treatments. In a preferred example, a subject is treated in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage used for treatment can increase or decrease over the course of a particular treatment. Changes in dosage can result and become apparent from the results of diagnostic assays as described herein.

The preferred embodiments encompass one or more additional agents that modulate expression or activity of Cdc42 GTPase. An agent can, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In one embodiment, the additional agent can be a prenylation inhibitor, such as disclosed by U.S. Pat. Nos. 6,649,638, 5,420,245; 5,574,025; 5,523,430; 5,602,098;

5,631,401; 5,705,686; 5,238,922; 5,470,832; and 6,191,147, all of which are incorporated herein by reference in their entirety.

In another embodiment, the additional agent comprises one or more inhibitor of farnesyl protein transferase (FPTase), prenyl-protein transferase or geranylgeranyl-protein transferase as described in U.S. Pat. Nos. 6,572,850; 6,458,783; 6,423,751; 6,387,926; 6,242,433; 6,191,147; 6,166,067; 6,156,746; 6,083,979; 6,011,029; 5,929,077; 5,928,924; 5,843,941; 5,786,193; 5,629,302; 5,618,964; 5,574,025; 5,567,841; 5,523,430; 5,510,510; 5,470,832; 5,447,922, 6,596,735; 6,586,461; 6,586,447; 6,579,887; 6,576,639; 6,545,020; 6,539,309; 6,535,820; 6,528,523; 6,511,800; 6,500,841; 6,495,564; 6,492,381; 6,458,935; 6,451,812; 6,441,017; 6,440,989; 6,440,974; 6,432,959; 6,426,352; 6,410,541; 6,403,581; 6,399,615; 6,387,948; 6,387,905; 6,387,903; 6,376,496; 6,372,747; 6,362,188; 6,358,968; 6,329,376; 6,316,462; 6,294,552; 6,277,854; 6,268,394; 6,265,382; 6,262,110; 6,258,824; 6,248,756; 6,242,458; 6,239,140; 6,228,865; 6,228,856; 6,225,322; 6,218,401; 6,214,828; 6,214,827; 6,211,193; 6,194,438, which are specifically incorporated herein by reference in their entirety.

A "farnesyl protein transferase inhibitor" or "FPT inhibitor" or "FTI" is defined herein as a compound which: (i) potently inhibits FPT (but generally not geranylgeranyl protein transferase I) and (ii) blocks intracellular farnesylation of ras. FPT catalyzes the addition of an isoprenyl lipid moiety onto a cysteine residue present near the carboxy-terminus of the Ras protein. This is the first step in a post-translational processing pathway that is essential for both Ras membrane-association and Ras-induced oncogenic transformation. A number of FPT inhibitors have been reported, including a variety of peptidomimetic inhibitors as well as other small molecule inhibitors.

Farnesyl transferase inhibitors generally fall into two classes: analogs of farnesyl diphosphate; and protein substrates for farnesyl transferase. Farnesyl transferase inhibitors have been described in U.S. Pat. Nos. 5,756,528, 5,141,851, 5,817,678, 5,830,868, 5,834,434, and 5,773,455, all of which are incorporated herein by reference in their entirety. Among the farnesyl transferase inhibitors shown to be effective for inhibiting the transfer of the farnesyl moiety to Ras-related proteins are L-739,749 (a peptidomimetic analog of the C-A-A-X sequence), L-744,832 (a peptidomimetic analog of the C-A-A-X sequence), SCH 44342 (1-(4-pyridylacetyl)-4-(8-chloro-5,6 dihydro-IIH benzo [5,6] cyclohepta [1,2-b]pyridin-11-yhdene)piperidine), BZA-5B (a benzodiazepine peptidomimetic), FTI-276 (a C-A-A-X peptidomimetic), and B1086 (a C-A-A-X peptidomimetic). Administration of farnesyl transferase inhibitors (FTIs) is accomplished by standard methods known to those of skill in the art, most preferably by administration of tablets containing the FTI, and is expected to fall approximately within a range of about 0.1 mg/kg of body to weight to about 20 mg/kg of body weight per day.

In another embodiment, the additional agent comprises one or more inhibitor of geranylgeranyl-protein transferase (GGT) as have been described in U.S. Pat. No. 5,470,832 (Gibbs & Graham), which is incorporated herein by reference in its entirety. These compounds can be administered to an individual in dosage amounts of between 0.5 mg/kg of body weight to about 20 mg/kg of body weight. Alternatively, one or more inhibitors of isoprenylation, including farnesyl transferase (FT) inhibitors and/or geranylgeranyl transferase inhibitors (GGT) are administered to a patient.

In another embodiment, the additional agent comprises one or more toxins such as toxins A and B from *C. difficile* and *C. sordellii* lethal toxin (LT). In addition, Rae 1 and Rac2 can be inhibited when Rho is specifically ADP ribosylated by C3 enzyme, which is one of the botulinum toxins, and Staphylococcal toxin EDIN (Narumiya, S. and Morii, S., Cell Signal, 5, 9-19, 1993; Sekine, A. et al., J. Biol. Chem., 264, 8602-8605, 1989, all of which are incorporated herein by reference in their entirety).

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the preferred embodiments. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses can be determined using the assays described herein. When one or more of these small molecules is to be administered to a subject (e.g., a human) in order to modulate expression or activity of a polypeptide or nucleic acid of the preferred embodiments, a physician, veterinarian, or researcher can, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Suitable dosage ranges for the active compound can vary according to these considerations, but in general, the compounds are administered in the range of about 0.1 μg/kg-5 mg/kg of body weight; preferably the range is about 1 μg/kg-300 μg/kg of body weight; more preferably about 10 μg/kg-100 μg/kg of body weight. For a typical 70-kg human subject, thus, the dosage range is from about 0.7 μg-350 mg; preferably about 700 μg-21 mg; most preferably about 700 μg-7 mg. Dosages can be higher when the compounds are administered orally or transdermally as compared to, for example, i.v. administration. The compounds can be administered as a single bolus dose, a dose over time, as in i.v. or transdermal administration, or in multiple dosages.

The amount of active compound to be administered can vary according to the discretion of the skilled artisan. The amount of active compound to be administered to the recipient is within the ranges described herein. However, the administration of such amounts will vary according to the standards set forth by clinicians.

The dosage regimen for rejuvenation of blood precursor cells, dermal epithelial precursor cells or intestinal epithelial precursor cells or weight control with the active compounds is based on a variety of factors, including the type of injury, the age, weight, sex, medical condition of the individual, the severity of the condition, the route of administration, and the particular compound employed. Thus, the dosage regimen can vary widely, but can be determined routinely by a physician using standard methods. Dosage levels of the order of between 0.1 ng/kg and 10 mg/kg body weight of the active compounds per body weight are useful for all methods of use disclosed herein.

The treatment regime will also vary depending on the condition being treated, based on a variety of factors, including the type of injury, the age, weight, sex, medical condition of the individual, the severity of the condition, the route of administration, and the particular compound employed.

In a preferred embodiment, the active compound is administered subcutaneously. A suitable subcutaneous dose of the active compound is preferably between about 0.1 ng/kg and about 10 mg/kg administered twice daily for a time sufficient to increase rejuvenation of blood precursor cells, dermal epithelial precursor cells or intestinal epithelial precursor cells. This dosage regimen maximizes the therapeutic benefits of the treatments while minimizing the amount of agent needed. Such an application minimizes costs as well as possible deleterious side effects.

For subcutaneous administration, the active ingredient can comprise from 0.0001% to 10% w/w, e.g. from 1% to 2% by weight of the formulation, although it can comprise as much as 10% w/w, but preferably not more than 5% w/w, and more preferably from 0.1% to 1% of the formulation. In a most preferred embodiment, subcutaneous administration of between about 1 to 1000 μg/kg/day of the active compounds is initiated at between one week before to one week after administration of a cancer therapy (e.g., a chemotherapeutic agent).

In all of these embodiments, the compounds can be administered prior to, simultaneously with, or subsequent to any other therapeutic exposure.

The active compounds can be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intratendinous, intraspinal, intracranial, intrathoracic, infusion techniques or intraperitoneally. In some embodiments, the active compounds are administered as a depot comprising a bio-compatible matrix formulated for continuous delivery of the agent in vivo. In some embodiments, the depot is formulated to degrade over time, thereby releasing the agent in a continuous or near-continuous manner. In some embodiments, the depot is formulated for release of the agent over the range of about 1 day to about 1, 2, 3, 4, 5, 6 months or more. In some embodiments, the depot can be an injectable depot for local administration. In some embodiments, the injectable depot is formulated for subcutaneous, intravenous, intraarterial, intramuscular, intrasternal, intratendinous, intraspinal, intracranial, intrathoracic, infusion techniques or intraperitoneallysubcutaneous, intravenous, intraarterial, intramuscular, intrasternal, intratendinous, intraspinal, intracranial, intrathoracic, infusion techniques or intraperitoneal injection. In some embodiments, the injectable depot is formulated for local injection at or near the stroma of the intestinal tract.

The active compounds can be made up in a solid form (including granules, powders or suppositories) or in a liquid form (e.g., solutions, suspensions, or emulsions). The compounds can be applied in a variety of solutions. Suitable solutions for use in accordance with the preferred embodiments are sterile, dissolve sufficient amounts of the peptide, and are not harmful for the proposed application. In this regard, the compounds disclosed herein are very stable but are hydrolyzed by strong acids and bases. The compounds are soluble in organic solvents and in aqueous solutions at pH 5-8.

The active compounds can be subjected to conventional pharmaceutical operations such as sterilization and/or can contain conventional adjuvants, such as preservatives, stabilizers, wetting agents, emulsifiers, buffers etc.

For administration, the active compounds are ordinarily combined with one or more adjuvants appropriate for the indicated route of administration. The compounds can be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds disclosed herein can be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent can include time delay material, such as glyceryl monostearate or glyceryl distearate alone or with a wax, or other materials well known in the art.

In some embodiments, the pharmaceutical composition comprises a Cdc42-specific inhibitor in a dosage formulated in an amount that is less than or equivalent to the amount that is sufficient to reduce GTP-bound Cdc42 levels in an aged precursor cell to the about the levels of GTP-bound Cdc42 in a normal, non-aged precursor cell. In some embodiments, the pharmaceutical composition comprises a Cdc42-specific inhibitor in a dosage formulated in an amount that is less than the amount that is sufficient to mobilize hematopoietic stem cells and progenitor cells from bone marrow into peripheral blood.

Additional Administration and Regimens

Some details regarding the administration of the Cdc422-specific inhibitor are provided supra. Additional information regarding administration and regimens for treatment are provided herein.

In some embodiments, only a single administration of the Cdc42-specific inhibitor is necessary for treating a subject. As discussed supra, this can be a factor determined by subject specific characteristics, such as age, health, or Cdc42 activity. Often, however, a subject may need more than one administration of the Cdc42-specific inhibitor to obtain the desired therapeutic result. Thus, in some embodiments, the administering of the Cdc42-specific inhibitor to said subject occurs once and in other embodiments, the administering of the Cdc42-specific inhibitor occurs more than once. Administering of the Cdc42-specific inhibitor can occur as often as needed for therapeutic efficacy, e.g. in some embodiments administering occurs 1 time, 2 times, 3 times, 4 times, 5 times, 6 times, 7 times, 8 times, 9 times, 10 times, 1-10 times, 1-9 times, 1-8 times, 1-7 times, 1-6 times, 1-5 times, 1-4 times, 1-3 times, 2-10 times, 2-9 times, 2-8 times, 2-7 times, 2-6 times, 2-5 times, 2-4 times, 2-3 times, 3-10 times, 3-9 times, 3-8 times, 3-7 times, 3-6 times, 3-5 times, 3-4 times, 4-10 times, 4-9 times, 4-8 times, 4-7 times, 4-6 times, 4-5 times, 5-10 times, 5-9 times, 5-8 times, 5-7 times, 5-6 times, 6-10 times, 6-9 times, 6-8 times, 6-7 times, 7-10 times, 7-9 times, 7-8 times, 8-10 times, 8-9 times, 9-10 times, about any of the aforementioned times of administration (e.g., about 3 times or about 1-3 times), or at least any of the aforementioned times of administration (e.g., at least 3 times, at least about 3 times, or at least about 1-3 times).

When more than one administration of a Cdc42-specific inhibitor is given to a subject, each administration may be of the same Cdc42-specific inhibitor or the administrations may be of different Cdc42-specific inhibitors. For example, a sample from the subject may be taken and screened to determine the best Cdc42-specific inhibitor at a given time of administration (e.g., a subject may respond better to a difference Cdc42-specific inhibitor as treatment progresses). Doses of the Cdc42-specific inhibitor may be adjusted during the course of treatment, resulting in a subject receiving the same or different doses of the same or different Cdc42-specific inhibitor during the course of treating the subject. Thus, in some embodiments, principles of personalized medicine are utilized to determine the Cdc42-specific inhibitor to be administered to a subject.

Administering the Cdc42-specific inhibitor to the subject in need of treatment may occur as a regimen. In some embodiments, the administering occurs as an everyday regimen occurring on 1 day, 2 days, 3 days, 4 days, 5 days, 6 days, 7 days, 8 days, 10 days, 11 days, 12 days, 13 days, 14 days, or a range bounded by any of the aforementioned days (e.g., 1-5 days or 3-7 days), or about any of the aforementioned days (e.g., about 2 days, about 1-5 days, or about 3-7 days). In some embodiments, the administering occurs as a non-consecutive day regimen. In some embodiments, the administering occurs on non-consecutive days for 1 day, 2 days, 3 days, 4 days, 5 days, 6 days, 7 days, 8 days, 10 days, 11 days, 12 days, 13 days, 14 days, 1 week, 2 weeks, 3 weeks, 1 month, 2 months, 3 months, 6 months, 9 months, 1 year, 5 years, 10 years, for the remaining life of the subject, or a range bounded by any of the aforementioned days, weeks, or months, or about any of the aforementioned days, weeks, or months.

A subject may require more than one administration or even more than one regimen of administration as outlined above. Accordingly, in some embodiments the everyday regimen or non-consecutive day regimen is repeated every day, every week, every month, every 6 months, every 9 months, every 12 months, every 2 years, every 5 years, a range bounded by any of the aforementioned time periods (e.g., every day to every week or every month to every 12 months), or about any of the aforementioned time periods (e.g., about every day to every week or about every month to every 12 months).

In some embodiments, a subject's Cdc42 activity is determined prior to the first administration, or prior to any subsequent administration, of a Cdc42-specific inhibitor (e.g., determining activity before a first administration but not before a second administration or determining activity before a first administration and before a second administration or determining activity before a first administration and not before a second administration but determining activity before a third administration). It may be beneficial, in some embodiments, to determine the subject's Cdc42 activity prior to each administration of a Cdc42-specific inhibitor (e.g., determining activity before a first administration and before a second administration or determining activity before a first administration and before a second administration and before a third administration). It may be beneficial for a physician to utilize the information gleaned from determining the subject's Cdc42 activity to prepare a patient-specific regimen or afford patient-specific treatment. Thus, in some embodiments, the regimen or administration of the Cdc42-specific inhibitor is determined, or administration is repeated, based upon the Cdc42 activity in the subject.

A threshold for Cdc42 activity may be utilized in order to decide an appropriate regimen or administration of Cdc42-specific inhibitor(s). In some embodiments, the regimen or administering of the Cdc42-specific inhibitor is repeated when the Cdc42 activity in the subject is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190% or 200%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), or about 25%, about 30%, about 40%, about 50%, about 55%, about 60%, about 70%, about 80%, about 90%, about 100%, about 105%, about 110%, about 115%, about 120%, or about 125% of the Cdc42 activity in the subject prior to first administering the Cdc42-specific inhibitor to said subject.

In addition to relying on a subject's Cdc42 activity to determine the regimen or administration of a Cdc42-specific inhibitor, or as an alternative to such reliance, the regimen or administration may be determined by the ratio of Cdc42-GTP to total Cdc42 levels in the subject. In some embodiments, the ratio of Cdc42-GTP to total Cdc42 levels in the subject is 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 prior to administering, about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 prior to administering, greater than 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 prior to administering, or greater than about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 prior to administering. In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%; at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%; at least 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-

80%, 60%-70%, 70%-100%, 70%-90%, 70%-80%, 80%-100%, 80%-90%; or at least 10%, 20%, 30%, 40%, 50%, 60%, 70%, 80%, 90% of blood precursor cells in the subject comprise the aforementioned ratio(s) of Cdc42-GTP to total Cdc42 levels prior to administration of a Cdc42-specific inhibitor. In some embodiments, the ratio of Cdc42-GTP to total Cdc42 levels in a subject's blood precursor cells is reduced after administration of a Cdc42-specific inhibitor. In some embodiments, the ratio of Cdc42-GTP to total Cdc42 levels in said blood precursor cells is less than 1.0, 1.1, 1.2, 1.3, 1.4, or 1.5 after said administering or less than about 1.0, 1.1, 1.2, 1.3, 1.4, or 1.5 after administration of a Cdc42-specific inhibitor. In some embodiments, the ratio of Cdc42-GTP to total Cdc42 levels in the blood precursor cells is at least 0.8, 0.9, 1.0, 1.1, 1.2 or greater or at least about 0.8, 0.9, 1.0, 1.1, 1.2 or greater after administration of a Cdc42-specific inhibitor.

Some subjects may benefit from repeated administration of a Cdc42-specific inhibitor for the remainder of the subject's life in order to maintain the above mentioned levels and ratios of CDC42 activity. Other subjects may benefit from repeated administration of a Cdc42-specific inhibitor during the course of a medical treatment plan in order to maintain the above mentioned levels and ratios of CDC42 activity. However, some subjects may not require continuing exposure to a Cdc42-specific inhibitor in order to maintain the above mentioned levels and ratios of CDC42 activity. Accordingly, in some embodiments, the subject is administered a Cdc42-specific inhibitor for the remainder of the subject's life in order to maintain the above mentioned levels and ratios of CDC42 activity. In other embodiments, the subject is administered a Cdc42-specific inhibitor during the course of a medical treatment plan in order to maintain the above mentioned levels and ratios of CDC42 activity. In still other embodiments, a subject is discontinued exposure to a Cdc42-specific inhibitor at the end of a course of medical treatment. In some embodiments, a subject is discontinued exposure to a Cdc42-specific inhibitor and the Cdc42-specific inhibitor-mediated change in said subject is maintained after discontinuing exposure.

In some embodiments, the subject is selected for treatment with a Cdc42-specific inhibitor on the basis of one or more of the subject's circulating cytokine levels. In some embodiments, one or more of a subject's circulating cytokine level is determined prior to the first administration, or prior to any subsequent administration, of a Cdc42-specific inhibitor (e.g., determining activity before a first administration but not before a second administration or determining activity before a first administration and before a second administration or determining activity before a first administration and not before a second administration but determining activity before a third administration). In some embodiments, the circulating cytokine level that is determined is interferon γ, interleukin 1α, interleukin 1β, or interleukin 9, and any combination thereof. In some embodiments, one or more of the subject's circulating cytokine level is used to select the subject for treatment with a Cdc42-specific inhibitor. It may be beneficial, in some embodiments, to determine one or more of a subject's circulating cytokine level prior to each administration of a Cdc42-specific inhibitor (e.g., determining circulating cytokine levels before a first administration and before a second administration or determining circulating cytokine levels before a first administration and before a second administration and before a third administration). It may be beneficial for a physician to utilize the information gleaned from determining the subject's one or more circulating cytokine level to prepare a patient-specific regimen or afford patient-specific treatment. Thus, in some embodiments, the regimen or administration of the Cdc42-specific inhibitor is determined, or administration is repeated, based upon one or more of a circulating cytokine level in the subject.

In some embodiments, one or more of a subject's circulating inflammatory cytokine level is determined prior to the first administration, or prior to any subsequent administration, of a Cdc42-specific inhibitor (e.g., determining activity before a first administration but not before a second administration or determining activity before a first administration and before a second administration or determining activity before a first administration and not before a second administration but determining activity before a third administration). In some embodiments, the circulating inflammatory cytokine level that is determined is interferon γ, interleukin 1α, or interleukin 1β, and any combination thereof. In some embodiments, one or more of the subject's circulating inflammatory cytokine level is used to select the subject for treatment with a Cdc42-specific inhibitor. It may be beneficial, in some embodiments, to determine one or more of a subject's circulating inflammatory cytokine level prior to each administration of a Cdc42-specific inhibitor (e.g., determining circulating inflammatory cytokine levels before a first administration and before a second administration or determining circulating cytokine levels before a first administration and before a second administration and before a third administration). It may be beneficial for a physician to utilize the information gleaned from determining the subject's one or more circulating inflammatory cytokine level to prepare a patient-specific regimen or afford patient-specific treatment. Thus, in some embodiments, the regimen or administration of the Cdc42-specific inhibitor is determined, or administration is repeated, based upon one or more of a circulating inflammatory cytokine level in the subject.

A threshold for circulating cytokine levels or circulating inflammatory cytokine levels may be utilized in order to identify a subject for treatment or to decide an appropriate regimen or administration of Cdc42-specific inhibitor(s). In some embodiments, the subject is selected for treatment with a Cdc42-specific inhibitor when one or more of the determined circulating cytokine levels or circulating inflammatory cytokine levels in the subject is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, or about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), or about 25%, about 30%, about 40%, about 50%, about 55%, about 60%, about 70%, about 80%, about 90%, about 100%, about 105%, about 110%, about 115%, about 120%, or about 125% of the circulating cytokine levels or circulating inflammatory cytokine levels in a control population. In some embodiments, the control population is predicated on age. In some embodiments, the control population is of an age that is 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 years old, or a range bounded by any of the aforementioned ages (e.g., an age that is equal to 18-20, 25-35, 50-80, 50-70, 50-60, 55-75, 55-75, 55-70, 55-65, 60-70, 52-71, 60-79, or 73-78 years old or an age that is older than 18-20, 25-35, 50-80, 50-70, 50-60, 55-75, 55-75, 55-70, 55-65, 60-70, 52-71, 60-79, or 73-78 years old). In some embodiments, the circulating cytokine level that is determined is interferon γ, interleukin 1α, interleukin 1β, or interleukin 9, and any combination thereof.

In some embodiments, the regimen or administering of the Cdc42-specific inhibitor is repeated when one or more of the determined circulating cytokine levels or circulating inflammatory cytokine levels in the subject is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), or about 25%, about 30%, about 40%, about 50%, about 55%, about 60%, about 70%, about 80%, about 90%, about 100%, about 105%, about 110%, about 115%, about 120%, or about 125% of the circulating cytokine levels or circulating inflammatory cytokine levels in a control population. In some embodiments, the control population is predicated on age. In some embodiments, the control population is of an age that is 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 years old, or a range bounded by any of the aforementioned ages (e.g., an age that is equal to 18-20, 25-35, 50-80, 50-70, 50-60, 55-75, 55-75, 55-70, 55-65, 60-70, 52-71, 60-79, or 73-78 years old or an age that is older than 18-20, 25-35, 50-80, 50-70, 50-60, 55-75, 55-75, 55-70, 55-65, 60-70, 52-71, 60-79, or 73-78 years old).

In some embodiments, the regimen or administering of the Cdc42-specific inhibitor is repeated when one or more of the determined circulating cytokine levels or circulating inflammatory cytokine levels in the subject is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), or about 25%, about 30%, about 40%, about 50%, about 55%, about 60%, about 70%, about 80%, about 90%, about 100%, about 105%, about 110%, about 115%, about 120%, or about 125% of the circulating cytokine levels or circulating inflammatory cytokine levels in the subject prior to first administering the Cdc42-specific inhibitor to said subject. In some embodiments, the circulating cytokine level that is determined is interferon γ, interleukin 1α, interleukin 1β, or interleukin 9, and any combination thereof.

In some embodiments, the effective amount of Cdc42-specific inhibitor decreases or reduces the level of one or more circulating cytokine levels in the subject. In some embodiments, the decrease or reduction in one or more circulating cytokine levels or one or more circulating inflammatory cytokine levels may be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), relative to the circulating cytokine levels or circulating inflammatory cytokine levels in the subject prior to first administering the Cdc42-specific inhibitor to said subject. In some embodiments, the circulating cytokine level that is determined is interferon γ, interleukin 1α, or interleukin 1β, and any combination thereof.

In some embodiments, the effective amount of Cdc42-specific inhibitor decreases or reduces the level of one or more circulating inflammatory cytokine levels in the subject. In some embodiments, the decrease or reduction in one or more circulating cytokine levels or one or more circulating inflammatory cytokine levels may be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), relative to the circulating cytokine levels or circulating inflammatory cytokine levels in a control population, upon administration of an effective amount of the Cdc42-specific inhibitor. In some embodiments, the control population is predicated on age. In some embodiments, the control population is of an age that is 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 years old, or a range bounded by any of the aforementioned ages (e.g., an age that is equal to 18-20, 25-35, 50-80, 50-70, 50-60, 55-75, 55-75, 55-70, 55-65, 60-70, 52-71, 60-79, or 73-78 years old or an age that is older than 18-20, 25-35, 50-80, 50-70, 50-60, 55-75, 55-75, 55-70, 55-65, 60-70, 52-71, 60-79, or 73-78 years old). In some embodiments, the circulating cytokine level that is determined is interferon γ, interleukin 1α, or interleukin 1β, and any combination thereof.

In some embodiments, the effective amount of Cdc42-specific inhibitor increases or elevates the level of one or more circulating cytokine levels in the subject. In some embodiments, there is an increase or elevation in one or more circulating cytokine levels that is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), relative to the circulating cytokine levels or circulating inflammatory cytokine levels in the subject prior to first administering the Cdc42-specific inhibitor to said subject, upon administration of an effective amount of the Cdc42-specific inhibitor. In some embodiments, the circulating cytokine level that is increased or elevated is interleukin 9.

In some embodiments, there is an increase or elevation in one or more circulating cytokine levels that is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), relative to the circulating cytokine levels or circulating inflammatory cytokine levels in a control population upon administration of an effective amount of the Cdc42-specific inhibitor. In some embodiments, the control population is predicated on age. In some embodiments, the control population is of an age that is 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 years old, or a range bounded by any of the aforementioned ages (e.g., an age that is equal to 18-20, 25-35, 50-80, 50-70, 50-60, 55-75, 55-75, 55-70, 55-65, 60-70, 52-71, 60-79, or 73-78 years old or an age that is older than 18-20, 25-35, 50-80, 50-70, 50-60, 55-75, 55-75, 55-70, 55-65, 60-70, 52-71, 60-79, or 73-78 years old. In some embodiments, the circulating cytokine level that is increased or elevated is interleukin 9.

In addition to relying on one or more combinations of a circulating cytokine level to select a subject or to determine the regimen or administration of a Cdc42-specific inhibitor, in some embodiments the subject, regimen, or administration is determined by a ratio of two or more circulating cytokine levels in the subject. In some embodiments, the circulating cytokine is one or more of interferon γ, interleukin 1α, interleukin 1β, and/or interleukin 9. In some embodiments, the ratio is one or more of interferon γ, interleukin 1α, or interleukin 1β to interleukin 9. In some embodiments, the ratio of circulating cytokine level in the subject is 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 prior to administering, about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 prior to administering, greater than 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 prior to administering, or greater than about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 prior to administering. In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%; at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%; at least 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%; or at least 10%, 20%, 30%, 40%, 50%, 60%, 70%, 80%, 90% of blood precursor cells in the subject comprise the aforementioned ratio(s) of circulating cytokine levels prior to administration of a Cdc42-specific inhibitor. In some embodiments, the ratio of circulating cytokine levels in a subject's blood precursor cells is reduced after administration of a Cdc42-specific inhibitor. In some embodiments, the ratio of circulating cytokine levels levels in said blood precursor cells is less than 1.0, 1.1, 1.2, 1.3, 1.4, or 1.5 after said administering or less than about 1.0, 1.1, 1.2, 1.3, 1.4, or 1.5 after administration of a Cdc42-specific inhibitor. In some embodiments, the ratio of circulating cytokine levels in the blood precursor cells is at least 0.8, 0.9, 1.0, 1.1, 1.2 or greater or at least about 0.8, 0.9, 1.0, 1.1, 1.2 or greater after administration of a Cdc42-specific inhibitor.

In some embodiments, the subject is selected for treatment with a Cdc42-specific inhibitor on the basis of the methylation status of one or more CpG sites. CpG sites or CG sites are regions of DNA where a cytosine nucleotide is followed by a guanine nucleotide in the linear sequence of bases along its 5'→3' direction. Cytosines in CpG dinucleotides can be methylated by DNA methyltransferases to form 5-methylcytosines. Methylating the cytosine within a gene can change its expression and is relevant to epigenetics and gene regulation. In some embodiments, methylation of cytosine within a CpG site is used to select a subject for treatment with a Cdc42-specific inhibitor. Age also has a strong effect on DNA methylation levels of cytosine within CpG sites, thus one can define a highly accurate biological clock (referred to as epigenetic clock or DNA methylation age) for a subject. In some embodiments, an "epigenetic clock" is used to select a subject for treatment with a Cdc42-specific inhibitor.

In some embodiments, the CpG site is within one or more of the Prima1, Hsf4, and Kcns1 genes, including combinations thereof. In some embodiments the methylation status of one or more of CpG sites within the Prima1, Hsf4, and Kcns1 genes, including combinations thereof, is determined prior to the first administration, or prior to any subsequent administration, of a Cdc42-specific inhibitor (e.g., determining levels before a first administration but not before a second administration or determining levels before a first administration and before a second administration or determining levels before a first administration and not before a second administration but determining levels before a third administration). In some embodiments, the methylation status of one or more of CpG sites within the Prima1, Hsf4, and Kcns1 genes, including combinations thereof, is used to select the subject for treatment with a Cdc42-specific inhibitor. It may be beneficial, in some embodiments, to determine the methylation status of one or more of CpG sites within the Prima1, Hsf4, and Kcns1 genes, including combinations thereof, prior to each administration of a Cdc42-specific inhibitor (e.g., determining cytosine methylation levels before a first administration and before a second administration or determining cytosine methylation levels before a first administration and before a second administration and before a third administration). It may be beneficial for a physician to utilize the information gleaned from determining the methylation status of one or more of CpG sites within the Prima1, Hsf4, and Kcns1 genes, including combinations thereof, to prepare a patient-specific regimen or afford patient-specific treatment. Thus, in some embodiments, the regimen or administration of the Cdc42-specific inhibitor is determined, or administration is repeated, based upon the methylation status of one or more of CpG sites within the subject's Prima1, Hsf4, and Kcns1 genes, including combinations thereof.

A threshold for the methylation status of one or more of CpG sites may be utilized in order to identify a subject for treatment or to decide an appropriate regimen or administration of Cdc42-specific inhibitor(s). In some embodiments, the methylation status of one or more of CpG sites within the subject's Prima1, Hsf4, and Kcns1 genes, including combinations thereof, is utilized in order to identify a subject for treatment or to decide an appropriate regimen or administration of Cdc42-specific inhibitor(s). In some embodiments, the subject is selected for treatment with a Cdc42-specific inhibitor when the methylation status of one or more of CpG sites in the subject is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, or about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), or about 25%, about 30%, about 40%, about 50%, about 55%, about 60%, about 70%, about 80%, about 90%, about 100%, about 105%, about 110%, about 115%, about 120%, or about 125% of the methylation status of one or more of CpG sites relative to a control population. In some embodiments, the one or more CpG sites is within the Prima1, Hsf4, and Kcns1 genes, including combinations thereof. In some embodiments, the referred to methylation status is the methylation of cytosine. In some embodiments, the control population is predicated on age. In some embodiments, the control population is of an age that is 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 years old, or a range bounded by any of the aforementioned ages (e.g., an age that is equal to 18-20, 25-35, 50-80, 50-70, 50-60, 55-75, 55-75, 55-70, 55-65, 60-70, 52-71, 60-79, or 73-78 years old or an age that is older than 18-20, 25-35, 50-80, 50-70, 50-60, 55-75, 55-75, 55-70, 55-65, 60-70, 52-71, 60-79, or 73-78 years old).

In some embodiments, the regimen or administering of the Cdc42-specific inhibitor is repeated when the methylation status of one or more of CpG sites in the subject is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), or about 25%, about 30%, about 40%, about 50%, about 55%, about 60%, about 70%, about 80%, about 90%, about 100%, about 105%, about 110%, about 115%, about 120%, or about 125% of the methylation status of one or more of CpG sites relative to a control population. In some embodiments, the one or more CpG sites is within the Prima1, Hsf4, and Kcns1 genes, including combinations thereof. In some embodiments, the referred to methylation status is the methylation of cytosine. In some embodiments, the control population is predicated on age. In some embodiments, the control population is of an age that is 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 years old, or a range bounded by any of the aforementioned ages (e.g., an age that is equal to 18-20, 25-35, 50-80, 50-70, 50-60, 55-75, 55-75, 55-70, 55-65, 60-70, 52-71, 60-79, or 73-78 years old or an age that is older than 18-20, 25-35, 50-80, 50-70, 50-60, 55-75, 55-75, 55-70, 55-65, 60-70, 52-71, 60-79, or 73-78 years old).

In some embodiments, the regimen or administering of the Cdc42-specific inhibitor is repeated when the methylation status of one or more of CpG sites in the subject is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), or about 25%, about 30%, about 40%, about 50%, about 55%, about 60%, about 70%, about 80%, about 90%, about 100%, about 105%, about 110%, about 115%, about 120%, or about 125% of the methylation status of one or more of CpG sites in the subject prior to first administering the Cdc42-specific inhibitor to said subject. In some embodiments, the one or more CpG sites is within the Prima1, Hsf4, and Kcns1 genes, including combinations thereof. In some embodiments, the referred to methylation status is the methylation of cytosine.

In some embodiments, the effective amount of Cdc42-specific inhibitor decreases or reduces the methylation status of one or more of CpG sites in the subject. In some embodiments, the regimen or administering of an effective amount of the Cdc42-specific inhibitor decreases or reduces the methylation status of one or more of CpG sites in the subject by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), relative to the methylation status of one or more of CpG sites in the subject prior to first administering the Cdc42-specific inhibitor to said subject or prior to last administering the Cdc42-specific inhibitor to said subject. In some embodiments, the one or more CpG sites is within the Prima1, Hsf4, and Kcns1 genes, including combinations thereof. In some embodiments, the referred to methylation status is the methylation of cytosine.

In some embodiments, the regimen or administering of an effective amount of the Cdc42-specific inhibitor decreases or reduces the methylation status of one or more of CpG sites in the subject by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 160%, 170%, 180%, 190%, 200%, 225%, 250%, 300%, 350%, about any of the aforementioned percentages, or a range bounded by any of the aforementioned percentages (e.g., about 1%-30%, about 5%-25%, about 5%-20%, about 5%-15% or 1%-30%, 5%-25%, 5%-20%, 5%-15%), 1%-100%, 1%-90%, 1%-80%, 1%-70%, 1%-60%, 1%-50%, 1%-40%, 1%-30%, 1%-20%, 1%-10%, 10%-100%, 10%-90%, 10%-80%, 10%-70%, 10%-70%, 10%-60%, 10%-50%, 10%-40%, 10%-30%, 10%-20%, 20%-100%, 20%-90%, 20%-80%, 20%-70%, 20%-60%, 20%-50%, 20%-40%, 20%-30%, 30%-100%, 30%-90%, 30%-80%, 30%-70%, 30%-60%, 30%-50%, 30%-40%, 40%-100%, 40%-90%, 40%-80%, 40%-70%, 40%-60%, 40%-50%, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, about any of the aforementioned range of percentages (e.g., about 10%-70%, about 30%-60%, or about 50%-70%), relative to the methylation status of one or more of CpG sites in a control population. In some embodiments, the control population is predicated on age. In some embodiments, the control population is of an age that is 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 years old, or a range bounded by any of the aforementioned ages (e.g., an age that is equal to 18-20, 25-35, 50-80, 50-70, 50-60, 55-75, 55-75, 55-70, 55-65, 60-70, 52-71, 60-79, or 73-78 years old or an age that is older than 18-20, 25-35, 50-80, 50-70, 50-60, 55-75, 55-75, 55-70, 55-65, 60-70, 52-71, 60-79, or 73-78 years old. In some embodiments, the one or more CpG sites is within the Prima1, Hsf4, and Kcns1 genes, including combinations thereof. In some embodiments, the referred to methylation status is the methylation of cytosine.

Information regarding procedural or other details supplementary to those set forth herein, are described in cited references specifically incorporated herein by reference.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

The following examples provide illustrations of some of the embodiments described herein but are not intended to limit the invention.

GENERAL EXPERIMENTAL PROCEDURES

Unless otherwise indicated, the following general procedures were applied:

Mice. Mice included in the study were female C57BL/6 and were obtained from the internal divisional stock (derived from C57BL/6j mice obtained from both The Jackson Laboratory and NIA/Charles River as well as from C57BL/6JRj mice from Janvier). For the longevity study described herein, 40 mice were randomly selected at 70 weeks of age. Mice were weighed and bled before the beginning of the treatment (day 0) and at day 7 and 35. Mice that failed to recover from blood sampling and mice that died due to laboratory errors were excluded. Mice that needed to be euthanized because they were scored as "weak and about to die" according to our approved animal license protocol for evaluating mouse health status remained part of the dataset. Allocation to control or treated group was done randomly (20 mice each experimental group).

Median lifespan, 95% confidence intervals and survival analysis were calculated by Prism GraphPad v7.0c. Of note, the median lifespan of the control group matched data obtained for C57BL/6j mice in a large set of lifespan studies of diverse inbred mouse strains. Young C57BL/6 mice were 10-week old and were hosted in the same room and setting of the old mice. Animals were maintained according to the recommendations of the European Convention for the Protection of Vertebrate Animals used for Experimental and other Scientific Purposes (ETS 123). Animals were housed in groups of up to 4 animals per cage in Macrolon Type II (long) cages with bedding and paper nesting material. The animals had access to food (V1124-3, Ssniff®) and water ad libitum. Animals were kept at a day/night rhythm of 12/12 hours throughout the experiment. Mouse experiments were performed in compliance with the European and German Law for Welfare of Laboratory Animals and were approved by the Institutional Review Board of Ulm University as well as by the Regierungspraesidium Tuebingen, Baden-Wurttemberg pursuant to an approved protocol.

CASIN solution and IP treatment. CASIN was prepared fresh before injection by dissolving the drug directly in beta-cyclodextrin solution (Sigma #H5784). IP injections were performed in the morning, every 24 hours, for 4 consecutive days during week 75 of age of the mice. Control mice were injected with equal volume of the solvent. Serum for the cytokine array was prepared from the day 7 bleeding point. Serum for mass spectrometry analysis of CASIN levels was prepared by bleeding an equal (for sex, strain, origin and age) cohort of mice 3 hours, 24 hours, and 48 hours after the end of the treatment. The same stock of CASIN was used for the entire study. CASIN was provided as lyophilized powder.

Flow cytometry of Peripheral Blood (PB). PB cell immunostaining was performed according to standard procedures and samples were analyzed on a LSRII flow cytometer (BD Biosciences). For PB lineage analysis, the antibodies used were from eBioscience: anti-CD3ε (clone 145-2C11), anti-B220 (clone RA3-6B2), anti-Mac-1 (clone M1/70) and anti-Gr-1 (clone RC57BL/6-8C5). Lineage FACS analysis data were plotted as the percentage of B220+, CD3+ and Myeloid (Gr-1+, Mac-1+ and Gr-1+Mac-1+) cells among total white blood cells. WBC (white blood cell), RBC (red blood cell), Ly (lymphocytes), NE (neutrophils), and Mo (monocyte) counts were generated by using the hemocytometer Hemavet 950, DREW SCIENTIFIC Inc, (FL 33014), USA.

Liquid Chromatography-Mass Spectrometry (LC-MS/MS) measurements of CASIN pharmacokinetics in mouse serum. A LC/MS/MS ion chromatography protocol was employed to measure serum CASIN concentration ranging 0.1-10 μM by comparing serum CASIN from i.p. injected mice at varying times with a standard curve derived by in vitro spiking of mouse serum with defined doses of CASIN. An Autosampler maximum recovery vials with caps (Waters), an UPLC-MS system (Waters Quattro Premier XE mass spectrometry with ACQUITY UPLC system), an Acquity BEH C18 UPLC column (2.1×75 mm, 1.7 μm) (Waters), and an Acquity BEH C18 UPLC guard column (Waters) were used. For LC gradient, solvent A contained acetonitrile/water (5/95) with 2 mM ammonium acetate and solvent B contained acetonitrile/water (90/10). The gradient mobile phase switched from 60% solvent A to 57% solvent A over 2 min, to 50% solvent A at 2.1 min, to 46% solvent A over 9.9 min, and then, after changing to 30% at 12.1 min, to 1% solvent A over 5.9 min, then to 60% solvent A at 18.1 min and this was held for 2 min. Column temperature was kept at 25° C. The capillary voltage was 3 KV for electrospray negative (ES−) mode, cone voltage is 45 V, collision 30 V, desolvation temperature, 350° C.; desolvation gas flow is 600 L/h; source temperature was 120° C.; and MRM transition m/z is 305.1→244.

Cytokine array. Lumimex Method. Cytokine concentrations in the sample supernatants were determined by using Milliplex™ Multiplex kits (MilliporeSigma, Darmstadt, Germany) according to manufacturer's protocol. Briefly, in a 96 well black plate, 25 μL sample in duplicate was incubated with 25 μL antibody coated beads overnight at 4° C. on a plate shaker. Plates were then washed 2 times using BioTek 405 TS (BioTek, Winooski, Vt.) and 25 μL of secondary antibody was added and incubated at room temperature for 1 hour while shaking. Finally, 25 μL of streptavidin-RPE was added directly to the secondary antibody and incubated for 30 minutes at room temperature with shaking. Plates were then washed 2 more times and 150 μL of sheath fluid was added. Plates were shaken for 5 minutes and then read using luminex technology on the Milliplex Analyzer (MilliporeSigma, Darmstadt, Germany). Concentrations were calculated from standard curves using recombinant proteins and expressed in pg/ml.

Cdc42-GTPase effector domain pull-down assays. Relative levels of GTP-bound Cdc42 were determined by an effector pull-down assay. Briefly, lineage depleted BM cells ($10^6$) were lysed in a $Mg^{2+}$ lysis/wash buffer (Upstate cell signaling solutions) containing 10% glycerol, 25 mM sodium fluoride, 1 mM sodium orthovanadate and a protease inhibitor cocktail (Roche Diagnostics). Samples were incubated with PAK-1 binding domain/agarose beads and bound (activated) as well as unbound (non-activated) Cdc42 fractions were probed by immunoblotting with an anti-Cdc42 antibody (Millipore, rabbit polyclonal). Activated protein was normalized to total protein and/or 3-actin (Sigma) and the relative amount was quantified by densitometry.

Analysis of the epigenetic aging signature. CASIN (Xcessbio #M60040) was prepared freshly before injection by dissolving in DMSO to a concentration of 100 mM and then diluted in cyclodextrin solution (Sigma #H5784). IP injections of 25 mg/kg were done on 4 consecutive days in the morning starting at an age of 77-86 weeks. Control mice were injected with equal volume of the solvents. Mice were sacrificed 8-9 weeks after treatment and blood was collected by heart puncture. The analysis of DNA methylation levels was analyzed at three age-associated CG dinucleotides (CpGs) as described previously. Briefly, genomic DNA was isolated from blood samples, bisulfite converted, and DNA methylation was analyzed within the three genes (Prima1, Hsf4, Kcns1) by pyrosequencing. The DNA methylation results at these sites were integrated into a multivariable model for epigenetic age predictions in B6 mice and correlated with the chronological age. Chronological and biological age of CASIN treated and control mice was compared using an unpaired t-test. Since the data was not normally distributed, all data was potentiated to obtain normal distribution before the statistical analysis was performed.

Example 1

Figure 2E:
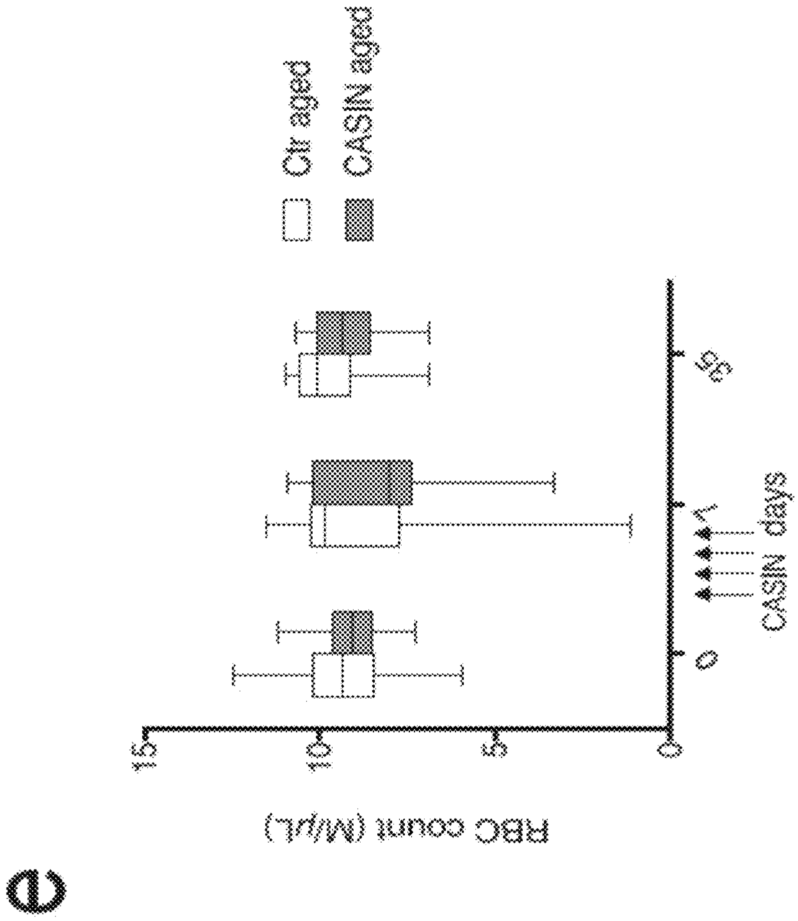
FIG. 2. (a) PK analysis of CASIN in mouse serum using LC/MS/MS ion chromatography of a 100 μL serum sample of a CASIN injected mouse; (b) Standard curve of CASIN in mouse serum by LC/MS/MS. CASIN was added to serum at 0, 0.5, 1.0, 5.0 μM concentrations and subsequently analyzed; (c) Weight in grams of the mice included in the lifespan study described in FIG. 1(*a*); (d-e) White blood cell (WBC) count and red blood cell count (RBC) of the mice included in the lifespan study described in FIG. 1(*a*); (f-h) Flow cytometry analysis of peripheral blood (PB) from mice of the lifespan study described in FIG. 1(*a*). Data are plotted as percentage of B220+, Cd3+ and Gr1+, Mac1+ and Gr1+Mac1+ cells among all white blood cells (WBCs); (i-k) Lymphocytes (Ly), Neutrophils (NE) and Monocyte (Mo) cell count from mice of the lifespan study described in FIG. 1(*a*). Data in FIGS. 2 (*c*) to (*k*) are depicted as box-plot showing min. to max values; n=18 for control (denoted "Ctr Aged" and represented by white boxes) and n=17 for animals treated with CASIN (denoted "CASIN aged" and represented by gray boxes). Days of analysis according to the scheme in FIG. 1*a*.

To determine that a short-term systemic treatment of aged animals with a Cdc42-specific inhibitor would regulate lifespan, CASIN was administered i.p. every 24 hours for 4 consecutive days to 75-week old female C57BL/6 mice (FIG. 1*a*). CASIN levels in serum were monitored via liquid chromatography-mass spectrometry (FIGS. 2*a* and 2*b*). A 50 mg/kg single dose resulted initially in a concentration of about 10 μM in serum (data not shown). Accordingly, a dosage of 25 mg/kg was selected, and mass spectrometry data from serum of old mice showed levels of CASIN 3 hours after injection in the expected range of 5 μM (FIG. 2*b*). The concentration of CASIN decreased over the 48 hour window of analysis, with approximately 2 μM concentration detected after 3 hours, approximately 1 μM detected after 2 hours, and approximately no CASIN remaining in serum at the end of the 48 hour window.

Figure 1C:
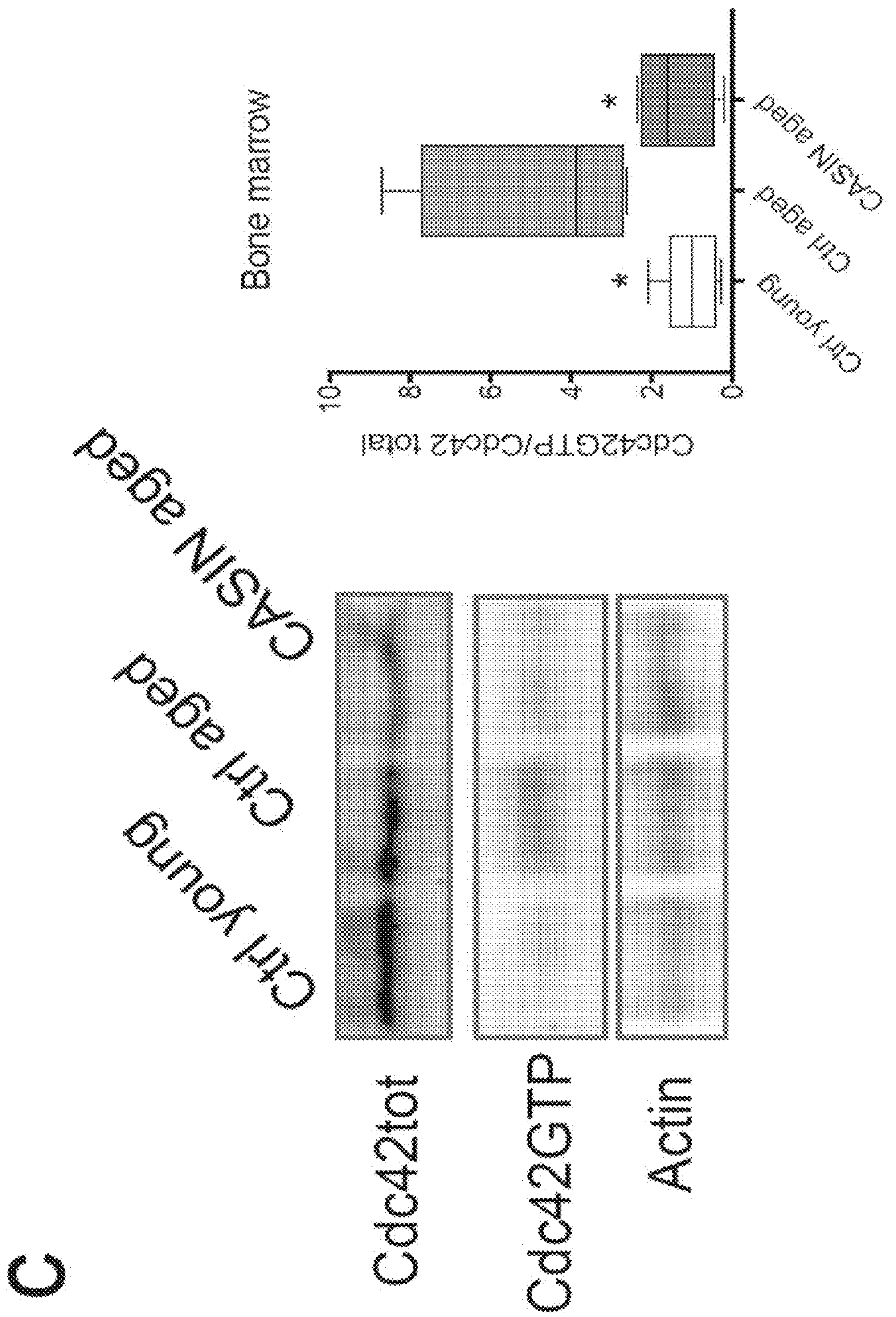

Four days of consecutive injections did not induce acute toxicity, and none of the treated mice died within 4 weeks after CASIN injections. Accordingly, chronic toxicity issues from the administration of inhibitor was unlikely. Quantification of Cdc42 activity 24 hours after the last injection on day 5 demonstrated a reduction of Cdc42-GTP in aged bone marrow cells to the level seen in young (FIG. 1*c*), confirming that CASIN is indeed reducing Cdc42 activity after a systemic in vivo treatment. As FIG. 1*c* indicates, CASIN treatment decreased Cdc42 activity by approximately half with no regard to the age of mouse. Furthermore, CASIN treatment reversed Cdc42 activity in the aged mice cohort to an approximate level of activity seen in the young mice control cohort. Thus, CASIN treatment generally reverted Cdc42 activity levels in aged mice to the level existing in mice approximately 60 weeks younger in age.

Figure 1D:
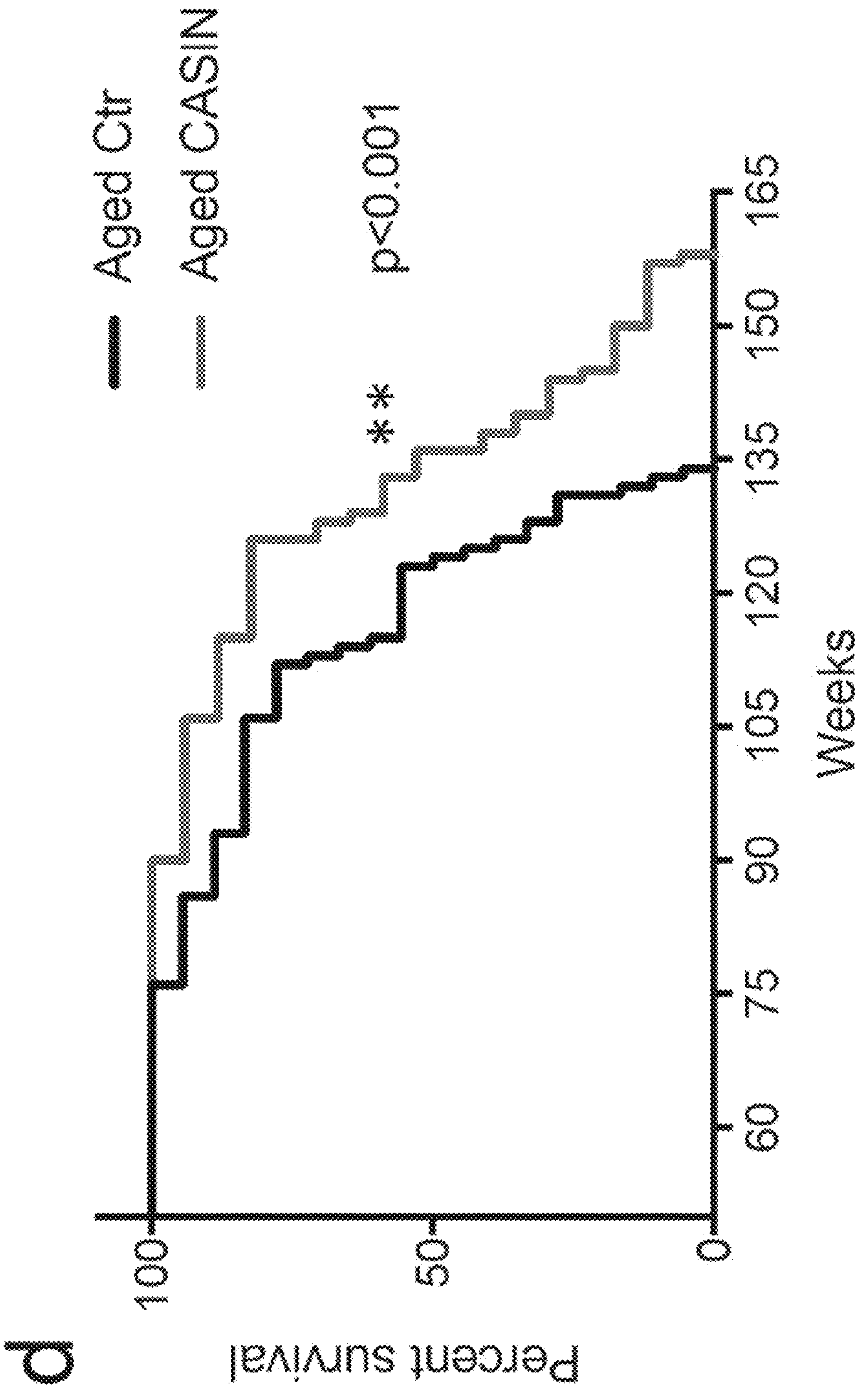

Notably, aged mice treated with CASIN for only 4 consecutive days showed extension of both their average and maximum lifespan (FIG. 1*d*). Accordingly, treatment with a Cdc42-specific inhibitor had a surprisingly effect on the increase in lifespan despite being cleared from the bloodstream shortly after discontinuance of drug treatment (e.g., a long-term influence by a short-term treatment), thereby illustrating durable benefits from drug treatment.

Figure 3:
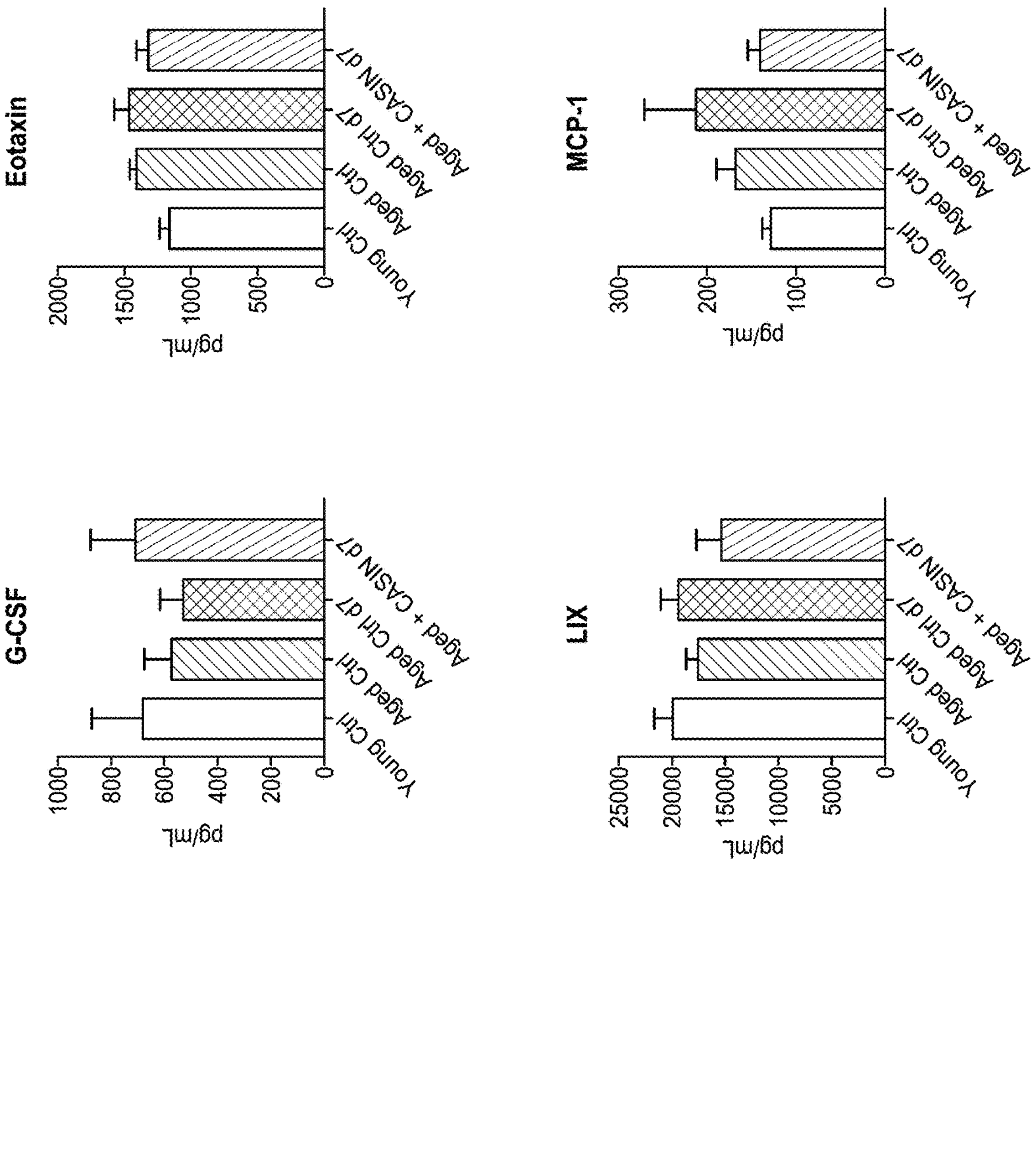
FIG. 3. Data from cytokine array analyses. Serum was collected from mice at day 0 (aged control) and day 7 (aged control and aged CASIN) according to the scheme illustrated in FIG. 1(*a*). Blood from young (10-week old) C57BL/6 female was used for the cytokine array young control sample. The number of experimental mice included was n=7 for young control ("Young Ctrl"), 27 for aged control day 0 ("Aged Ctrl"), 9 for aged control day 7 ("Aged Ctrl d7"), and 10 for aged CASIN day 7 ("Aged+CASIN d7"). The serum samples were loaded simultaneously for all cytokines probed and all experimental arms. Some samples did not generate a signal above the background due to technical reasons and were excluded from the statistical analysis. Bars represent mean+/−SEM. *$p<0.05$; **$p<0.01$ according to one-way ANOVA analysis and Tukey's multiple comparisons test.
Figure 3:
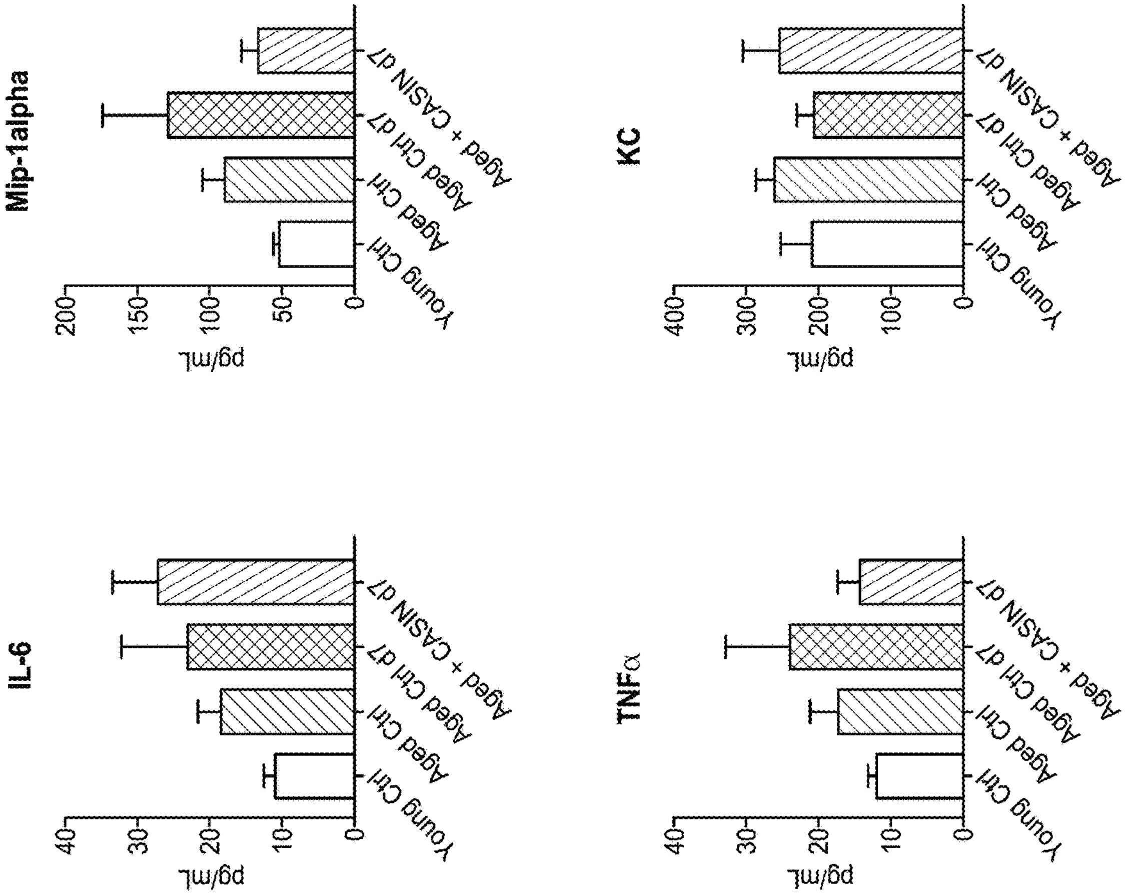
Figure 3:
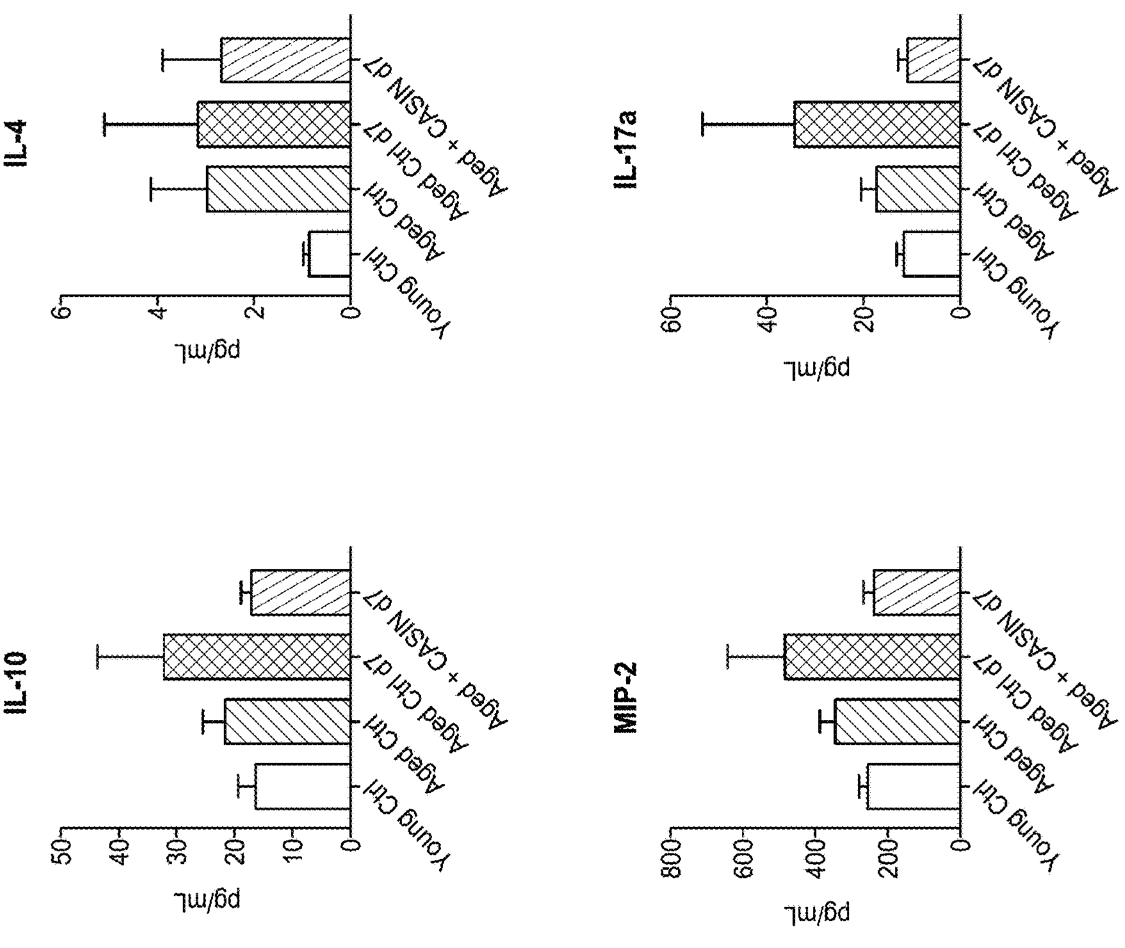
Figure 3:
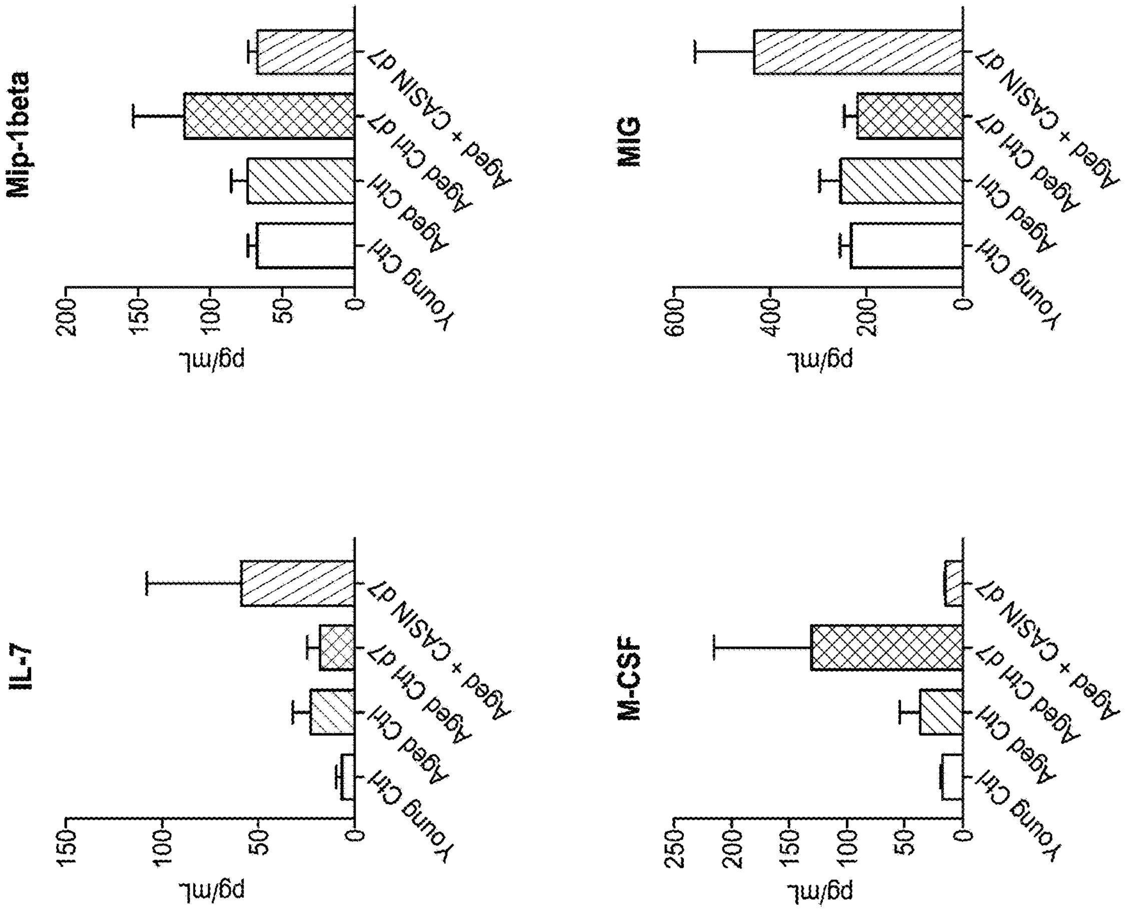
Figure 3:
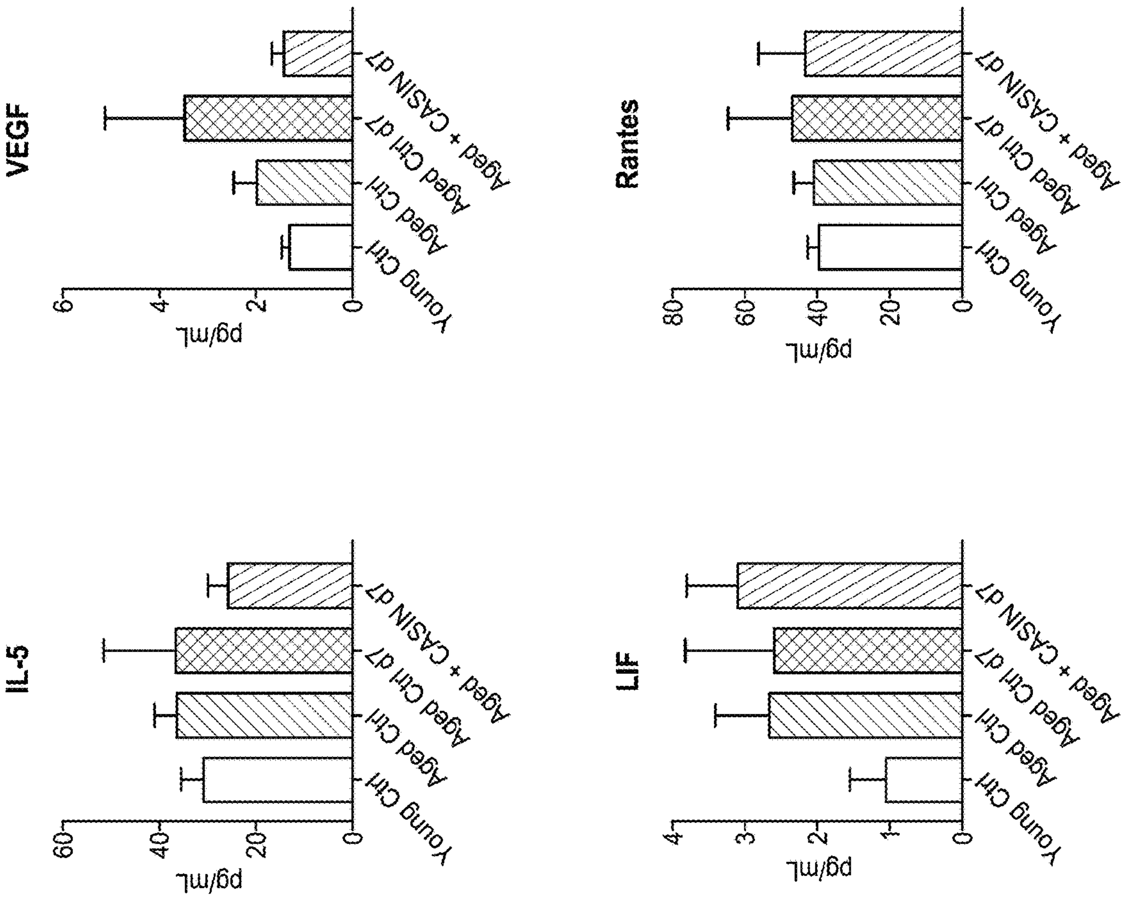
Figure 3:
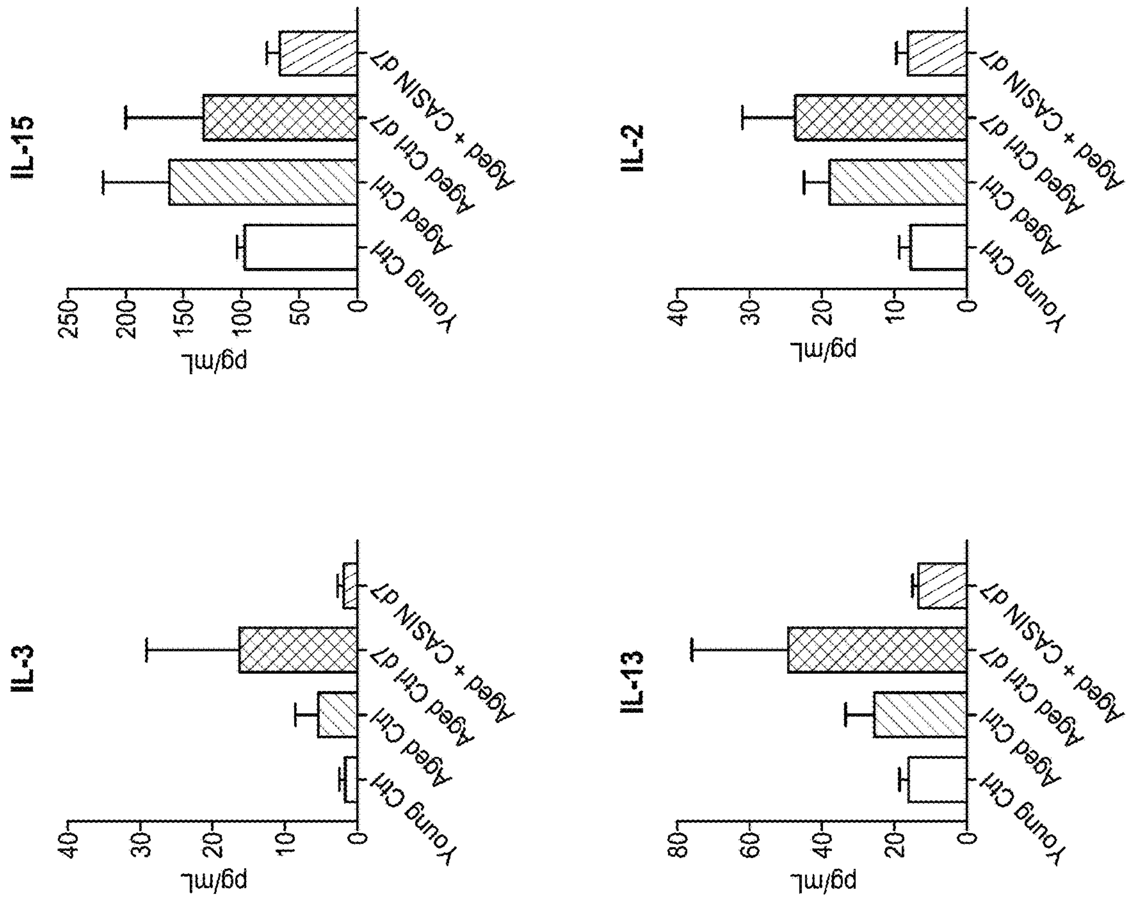
Figure 3:
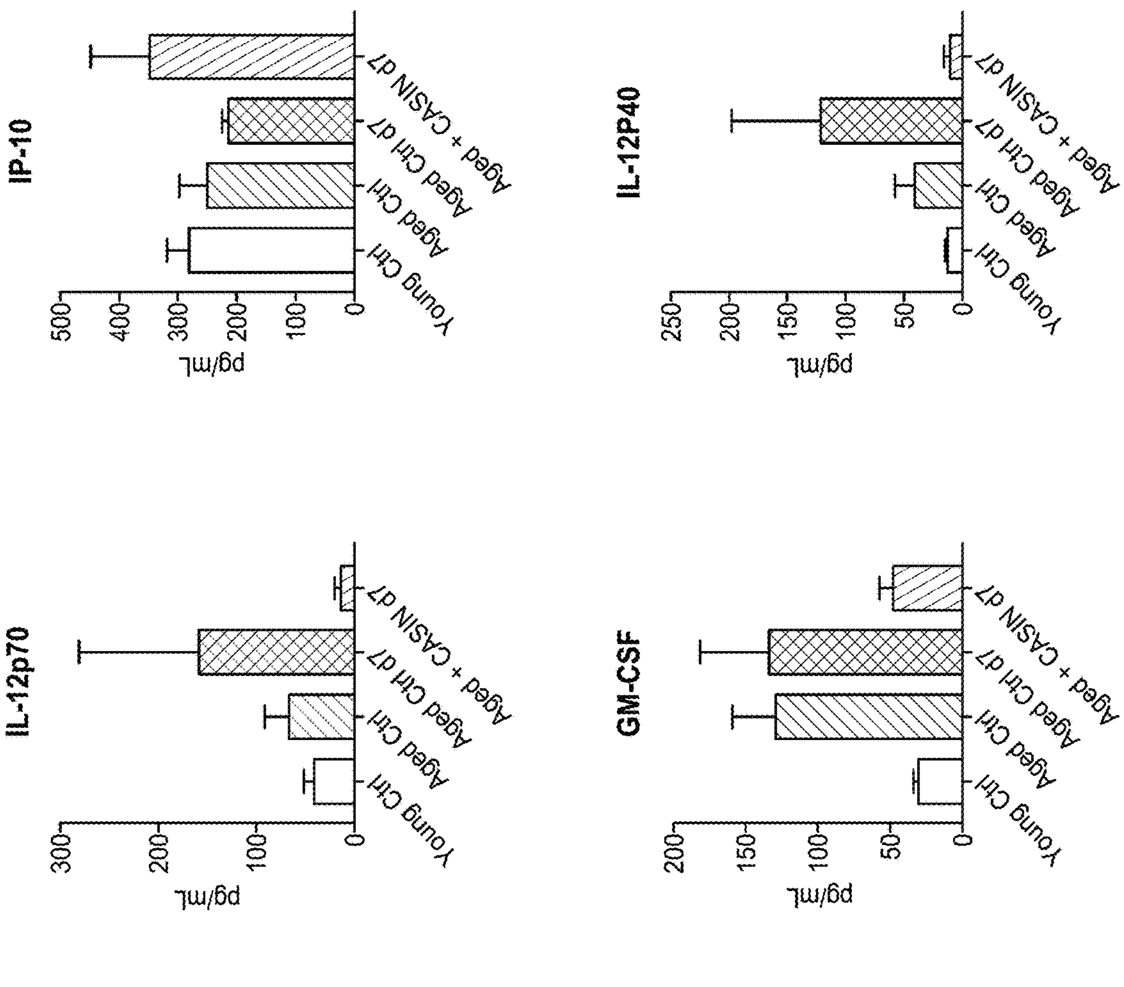
Figure 4:
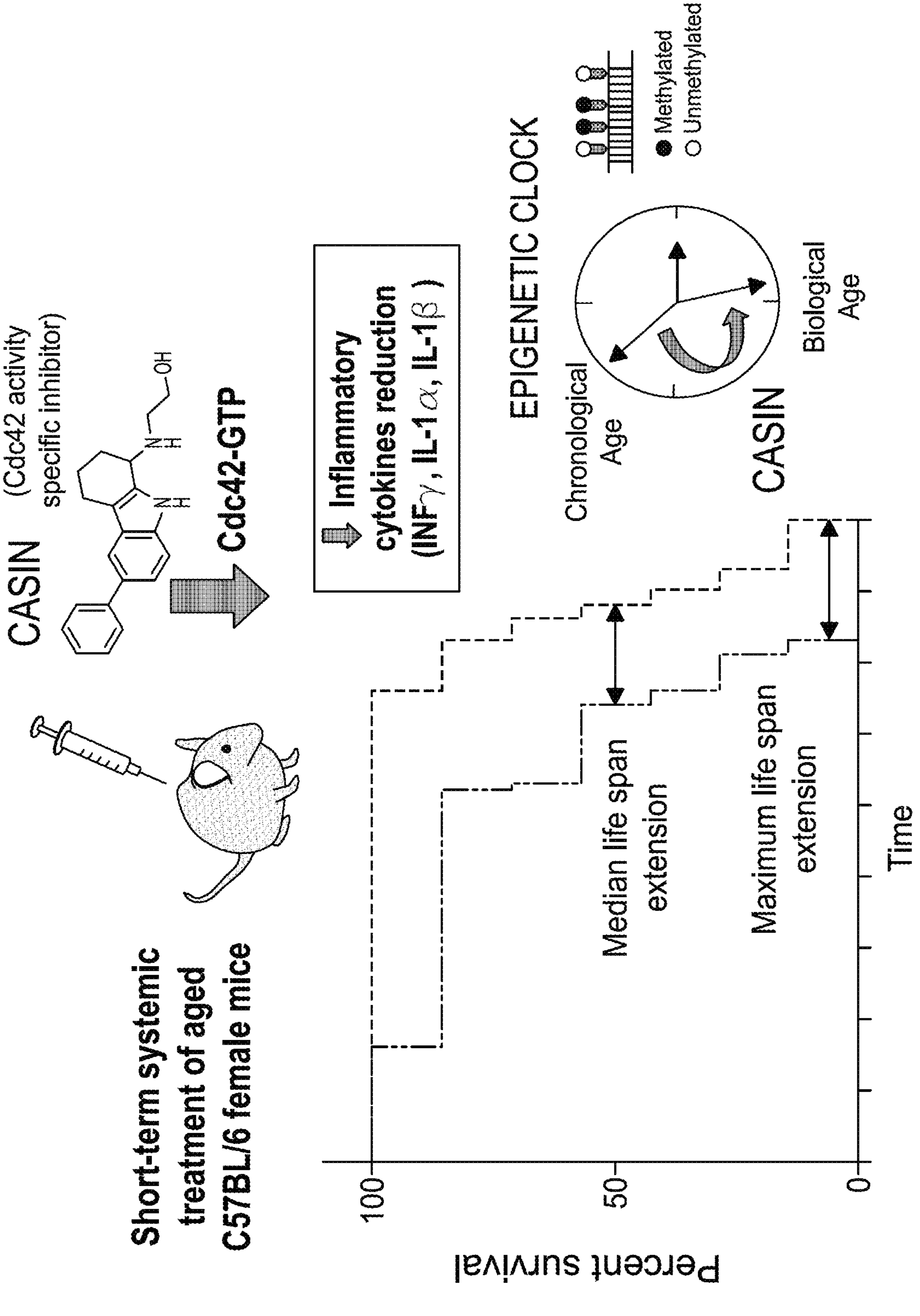
FIG. 4. Summary illustrating the short-term systemic treatment of elderly mice with a Cdc42-specific inhibitor (e.g., CASIN), and the extension of median and maximum life spans, reduction of inflammatory cytokines (e.g., INFγ, IL-1α, IL-1β), and dialing back (e.g., resetting) the epigenetic clock for DNA methylation levels as indicative of chronological age in comparison to biological age.

Also notable, the weight (FIG. 2*c*), the white blood cell count (WBC) (FIG. 2*d*), the red blood cell count (RBC) (FIG. 2*e*), and the frequency and count of myeloid and lymphoid cells in peripheral blood (PB) did not change in response to CASIN treatment, both short-term (e.g., day 7 after beginning of the treatment) and long-term (e.g., day 35 after beginning of the treatment) (FIGS. 2*f-k*). Cytokine array analyses were performed to investigate the extent to which aging-associated inflammatory cytokines in serum of aged mice were affected by CASIN treatment. Data showed a marked increase in the concentrations of INFγ, IL-1β and IL-1α on aging and the concentrations of these cytokines were similar to concentrations in young animals upon CASIN treatment of aged animals (FIGS. 1*e-g*). Accordingly, CASIN treatment reduced concentrations of these cytokines and, without being bound by any theory, this reduction of aging-associated inflammatory cytokines may contribute to the increase in lifespan observed in these animals. Interestingly, IL-9 was the only cytokine analyzed that increased in serum concentration after CASIN treatment (FIG. 1*h*). The concentrations of IL-6, IL-2, GM-CSF, LIF, IL-4, IL-7 showed a not significant trend to increase in aged mice and some (GM-CSF, IL-2) also showed a trend to be reduced by CASIN, while for a large number of cytokines their concentration was not altered either by aging or CASIN treatment (FIG. 3).

Figure 1I:
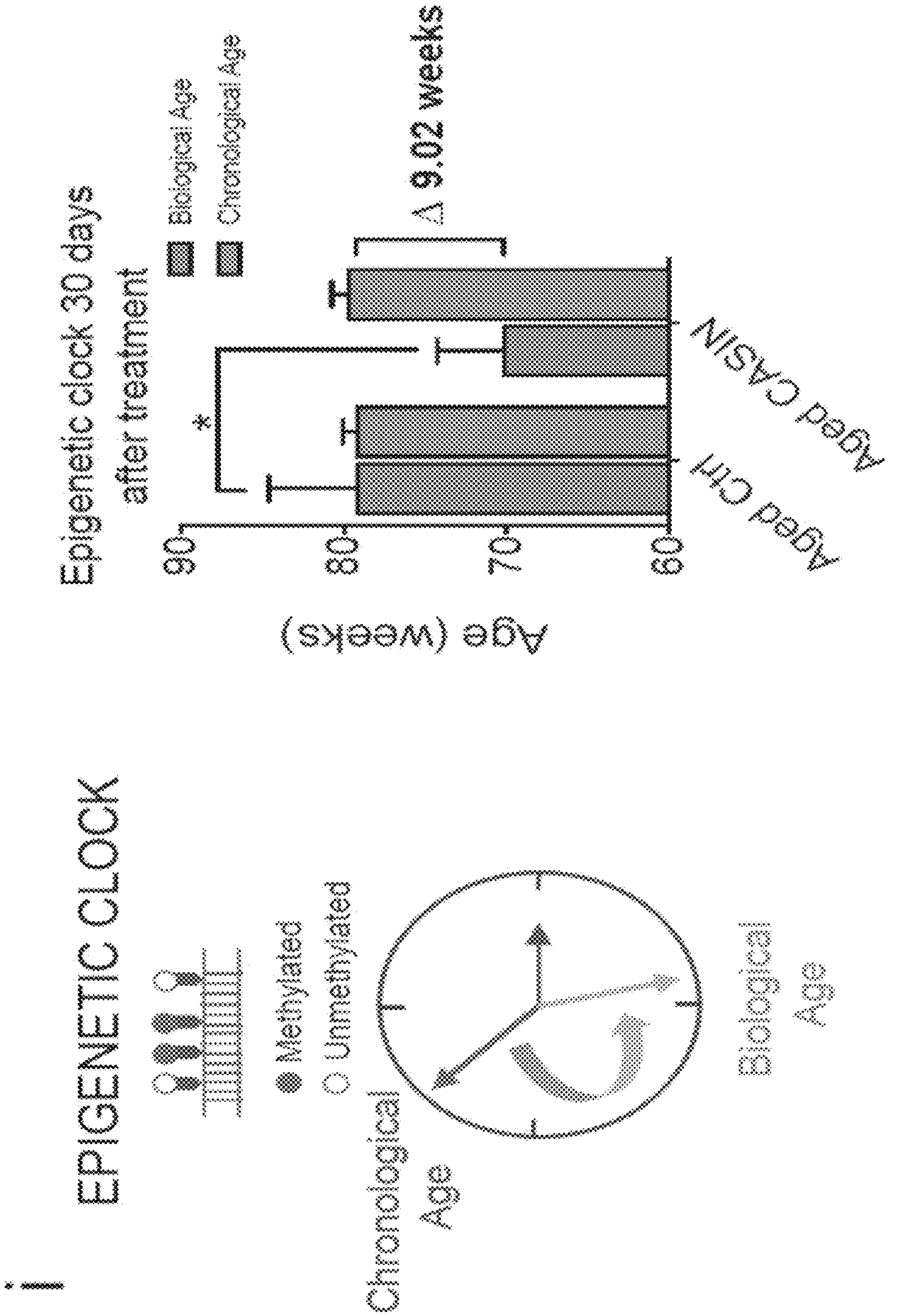

DNA methylation status of CpG (5'-C-phosphate-G-3') sites within the genes Prima1, Hsf4, and Kcns1 is a likely predictor of biological age of C57BL/6 mice. Therefore, DNA methylation profiling of these CpGs was investigated as a biological epigenetic clock. This C57BL/6-trained DNA methylation marker panel was applied to blood cells from aged animals treated with CASIN 9 weeks after treatment, and it was observed that epigenetic age predictions did not correlate anymore to the chronological age as in aged control animals. Instead, treatment with a Cdc42-specific inhibitor resulted in a biological age prediction that was on average 9 weeks younger than chronological age of the mice (FIG. 1*i*). Accordingly, mice treated with a Cdc42-specific inhibitor (e.g., CASIN) exhibit epigenetic changes that, without being bound by any theory, may influence the observed extended longevity of aged CASIN-treated mice.

Moreover, many age-related diseases, such as obesity, metabolic syndrome, diabetes, cardiovascular diseases, cancer, depression, and Alzheimer's disease, share an inflammatory pathogenesis; and the activation of inflammatory pathways appears to be involved in the pathophysiology of sarcopenia and frailty. Without being bound by any theory, elevated concentrations of interferon γ, as detected in these experiments may be a conserved hallmark of aging and might be functionally linked to lifespan. Similarly, both Interleukin 1α and Interleukin 1β have been associated with many aging-associated phenotypes and diseases. As for IL-9, which showed an increase in the concentration in serum after CASIN treatment, IL-9 is a pleiotropic cytokine mainly produced by T-helper 9 (Th9) cells and exerts documented effects on lymphocytes, mast cells, and resident lung cells. Without being bound by any theory, the data described herein suggests a role for elevated concentrations of these cytokines for the regulation of lifespan. The data further reveals that the methylation status of CpG sites within the genes Prima1, Hsf4, and Kcns1 in blood cells strongly correlate with biological age and serves as a validated biomarker of aging in C57BL/6 mice.

As noted above, the data herein demonstrates here that a reduction of Cdc42 activity in aged mice indeed extends lifespan. Notably, inhibition of Cdc42 activity by CASIN and inhibition of mTOR by rapamycin are the only reported pharmacological treatments that have significant effects on murine lifespan when given already quite late in life (75 weeks of age or more) and only temporary (only 4 days for CASIN; 90 days for rapamycin). This illustrates a mechanism of action for CDC42-specific inhibitors that is distinct from other pharmacological interventions for lifespan, which usually are either given earlier in life and/or are provided continuously for long time periods to achieve a significant effect.

Example 2

Figure 5:
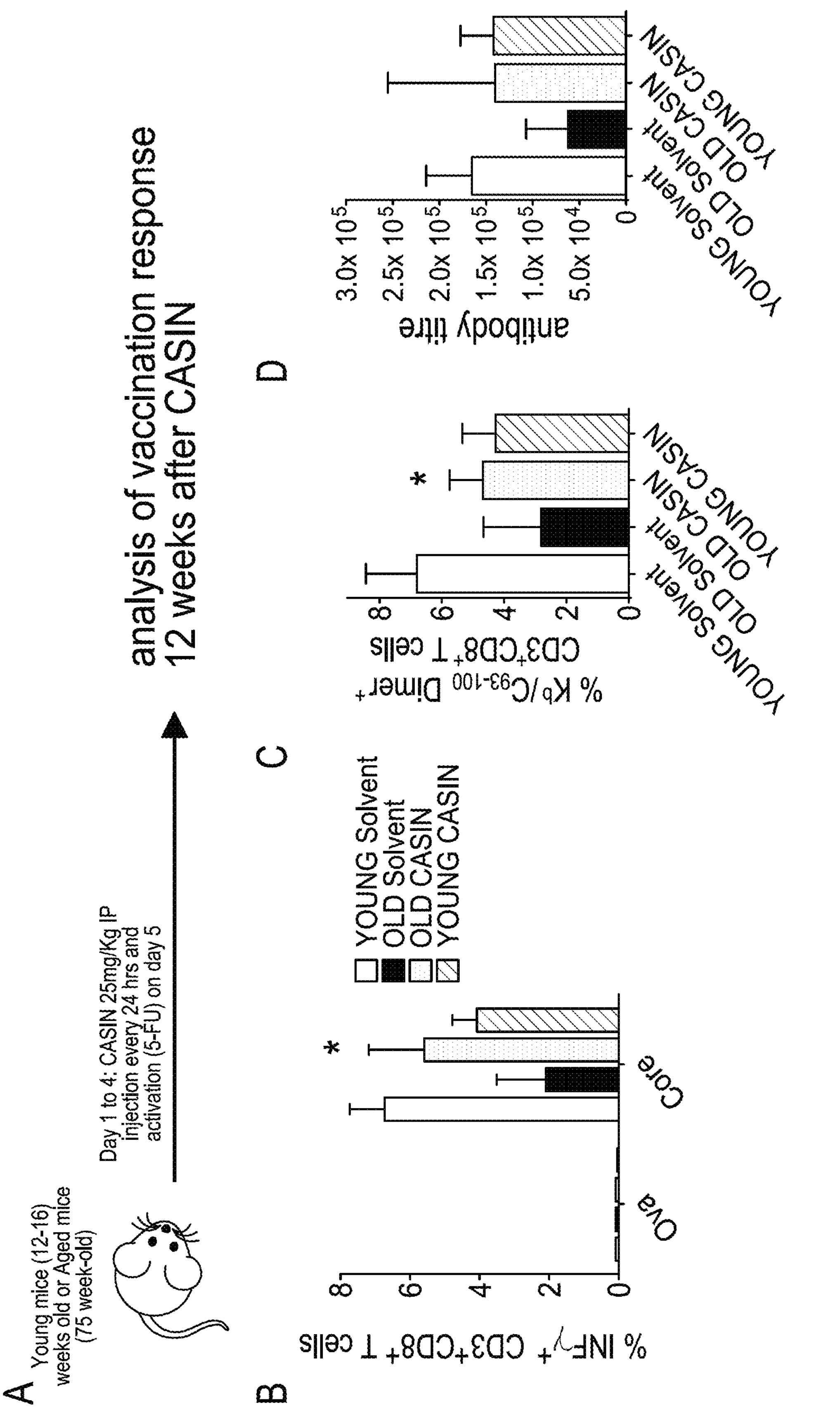
FIG. 5. (A) Scheme of an experimental set-up for analyzing vaccination response. (B) Quantification of interferon gamma positive $CD3^+CD8^+$ T-cells according to the protocol of FIG. 5(A); (C) Quantification of splenic $K^b/C_{93-100}$-dimer+$CD8^+$ T-cell frequencies determined by flow cytometry according to the protocol of FIGS. 3(A); and (D) Antibody titer after viral vaccination illustrating effects of age and Cdc42-specific inhibitor treatment according to the protocol of FIG. 3(A).

An experimental setup for vaccination response experiments is provided in FIG. 5(A). Briefly, 75 week-old C57BL/6 mice (referred to in the results as "Old") and 12-16 week old mice (referred to in the results as "young") were injected intraperitoneal ("IP") every 24 hours for four days with a Cdc42-specific inhibitor (e.g., CASIN) at a dosage of interest (e.g., 25 mg/kg) or with solvent as a control group (referred to in the results as "Solvent"). On the fifth day, mice were treated with 5-fluorouracil ("5-FU"). Two methods of vaccination were investigated.

For DNA vaccination: 12 weeks after transplantation, recipient mice were immunized with pCI/C DNA encoding the hepatitis B virus ("HBV") core antigen. FIG. 5(B) provides the results for DNA vaccination with the HBV core antigen 13 days after immunization along with an ovalbumin ("Ova") specific immune response. The frequency of interferon gamma positive $CD3^{+}CD8^{+}$ T-cells was analyzed, which is an established surrogate measurement for the success of DNA vaccination protocols. As FIG. 5(B) indicates, all mice exhibited an increase in the frequency of interferon gamma positive $CD3^{+}CD8^{+}$ T-cells after immunization with HBV core antigen. Aged mice treated with CASIN exhibited a statistically significant increase in immune response. n=at least 3 per experiment. * $p<0.05$ OLD Solvent vs. OLD CASIN. In FIG. 5(C), splenic $K^{b}/C_{93-100}$-dimer$^{+}$ $CD8^{+}$ T-cell frequencies were determined by flow cytometry 13 days post-immunization with the HBV core antigen. These T-cell frequencies are a direct measurement of antigen-specific T-cells. Aged mice treated with CASIN exhibited a statistically significant increase in antigen-specific T-cells. n=at least 3 per experiment. * $p<0.05$ OLD Solvent vs. OLD CASIN.

For viral vaccination, animals were immunized twice at an interval of 4 weeks with inactivated influenza virus (10 μg $H_3N2$+10 μL $Al(OH)_3$) i.m. 12 weeks post CASIN treatment. The antibody titer was determined in serum 21 days after the second vaccination using ELISA technology. n=at least 3 per experiment. These results are provided in FIG. 5(D), which highlights an increase in antibody titer for aged mice treated with CASIN relative to aged mice treated with solvent as the control cohort. The results suggest that aged mice treated with CASIN exhibited an antibody titer approximately equal to that seen in young mice, regardless of CASIN treatment within that cohort.

What is claimed is:

1. A method of treating age-related depression in an elderly human in need thereof comprising:

administering to the elderly human an effective amount of a Cdc42-specific inhibitor selected from the group consisting of:

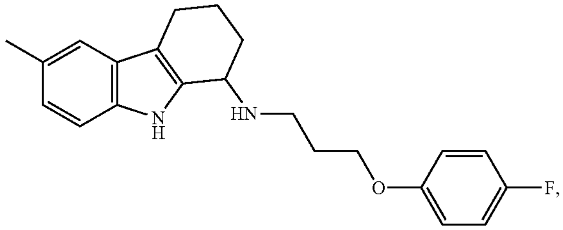
,

-continued

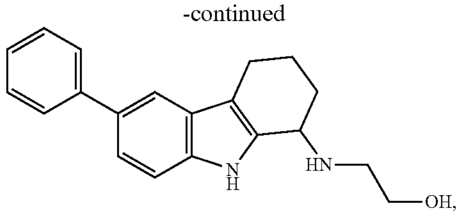

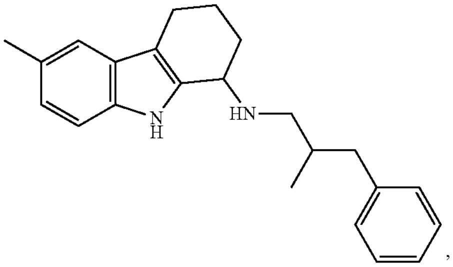

,

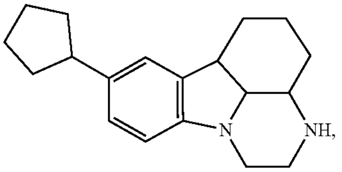

and

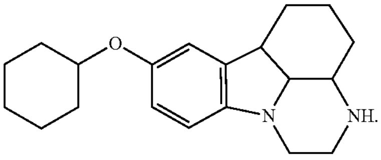

and combinations thereof.

2. The method of claim 1, wherein the administering of the Cdc42-specific inhibitor occurs more than once.

3. The method of claim 1, wherein the Cdc42 activity level in the elderly human is determined prior to administering the Cdc42-specific inhibitor.

4. The method of claim 1, wherein the Cdc42-specific inhibitor is:

(CASIN)

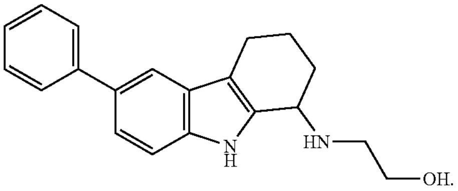

5. The method of claim 4, wherein the administered amount of CASIN is an amount sufficient to achieve a serum CASIN concentration of between about 0.1 to about 10 μM when measured about three hours following administration.

6. The method of claim 4, wherein the Cdc42 activity level in the elderly human is determined prior to administering the CASIN.

7. The method of claim 6, wherein the administered amount of CASIN is an amount sufficient to achieve a serum CASIN concentration of between about 0.1 to about 10 μM when measured about three hours following administration.

8. A method of treating age-related sarcopenia in an elderly human in need thereof comprising:

administering to the elderly human an effective amount of a Cdc42-specific inhibitor selected from the group consisting of:

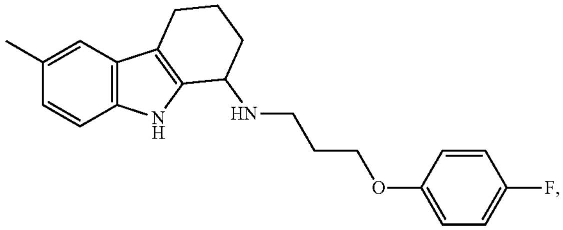

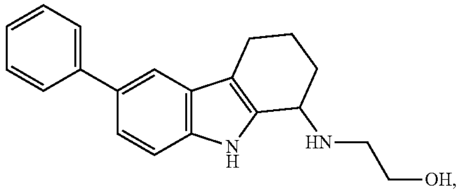

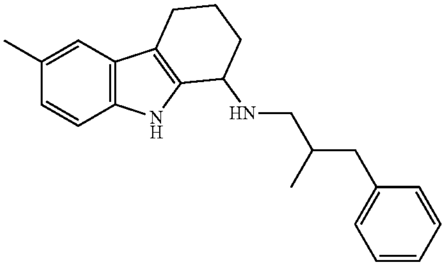

,

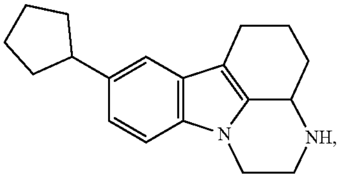

and

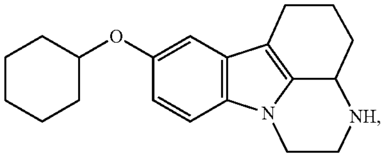

and combinations thereof.

9. The method of claim 8, wherein the administering of the Cdc42-specific inhibitor occurs more than once.

10. The method of claim 8, wherein the Cdc42 activity level in the elderly human is determined prior to administering the Cdc42-specific inhibitor.

11. The method of claim 8, wherein the Cdc42-specific inhibitor is:

(CASIN)

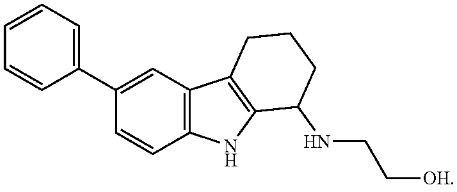

12. The method of claim 11, wherein the administered amount of CASIN is an amount sufficient to achieve a serum CASIN concentration of between about 0.1 to about 10 μM when measured about three hours following administration.

13. The method of claim 11, wherein the Cdc42 activity level in the elderly human is determined prior to administering the CASIN.

14. The method of claim 13, wherein the administered amount of CASIN is an amount sufficient to achieve a serum CASIN concentration of between about 0.1 to about 10 μM when measured about three hours following administration.

* * * * *